US012807592B2

(12) United States Patent
Hanselmann et al.

(10) Patent No.: US 12,807,592 B2
(45) Date of Patent: Nov. 24, 2026

(54) SYNTHESIS OF MAVORIXAFOR AND INTERMEDIATES THEREOF

(71) Applicant: X4 Pharmaceuticals, Inc., Boston, MA (US)

(72) Inventors: Roger Hanselmann, Boston, MA (US); Karel Marie Joseph Brands, Todi (IT)

(73) Assignee: X4 Pharmaceuticals, Inc., Boston, MA (US)

( * ) Notice: Subject to any disclaimer, the term of this patent is extended or adjusted under 35 U.S.C. 154(b) by 95 days.

(21) Appl. No.: 18/699,227

(22) PCT Filed: Oct. 7, 2022

(86) PCT No.: PCT/US2022/046094
§ 371 (c)(1),
(2) Date: Apr. 5, 2024

(87) PCT Pub. No.: WO2023/059903
PCT Pub. Date: Apr. 13, 2023

(65) Prior Publication Data

US 2025/0236604 A1 Jul. 24, 2025

Related U.S. Application Data

(60) Provisional application No. 63/262,225, filed on Oct. 7, 2021.

(51) Int. Cl.

| | |
|---|---|
| ***C07D 401/12*** | (2006.01) |
| ***C07C 303/14*** | (2006.01) |
| ***C07C 309/14*** | (2006.01) |
| ***C07D 215/06*** | (2006.01) |

(52) U.S. Cl.
CPC .......... *C07D 401/12* (2013.01); *C07C 303/14* (2013.01); *C07C 309/14* (2013.01); *C07D 215/06* (2013.01)

(58) Field of Classification Search
CPC .................................................... C07D 401/12
See application file for complete search history.

(56) References Cited

U.S. PATENT DOCUMENTS

| | | | |
|---|---|---|---|
| 4,933,447 | A | 6/1990 | Koono et al. |
| 5,021,409 | A | 6/1991 | Murrer et al. |
| 5,235,056 | A | 8/1993 | Cunkle et al. |
| 5,563,151 | A | 10/1996 | Bowles et al. |
| 5,582,823 | A | 12/1996 | Souza |
| 5,583,131 | A | 12/1996 | Bridger et al. |
| 5,698,546 | A | 12/1997 | Bridger et al. |
| 5,817,807 | A | 10/1998 | Bridger et al. |
| 5,932,749 | A | 8/1999 | Li et al. |
| 6,001,826 | A | 12/1999 | Murrer et al. |
| 6,245,799 | B1 | 6/2001 | Asselin et al. |
| 6,268,354 | B1 | 7/2001 | Nishimura et al. |
| 6,552,065 | B2 | 4/2003 | Remiszewski et al. |
| 6,635,278 | B1 | 10/2003 | Dahl et al. |
| 6,683,192 | B2 | 1/2004 | Baxter et al. |
| 6,734,194 | B2 | 5/2004 | End et al. |
| 6,794,379 | B2 | 9/2004 | Medina et al. |
| 6,825,351 | B2 | 11/2004 | McEachern et al. |
| 6,835,731 | B2 | 12/2004 | Bridger et al. |
| 6,864,265 | B2 | 3/2005 | Bridger et al. |
| 6,878,714 | B2 | 4/2005 | Askew et al. |
| 7,053,215 | B2 | 5/2006 | Medina et al. |
| 7,135,570 | B2 | 11/2006 | McEachern et al. |
| 7,169,750 | B2 | 1/2007 | Bridger et al. |
| 7,291,631 | B2 | 11/2007 | Bridger et al. |
| 7,332,605 | B2 | 2/2008 | Crawford et al. |
| 7,354,934 | B2 | 4/2008 | Bridger et al. |
| 7,390,799 | B2 | 6/2008 | Bruncko et al. |
| 7,452,994 | B2 | 11/2008 | McEachern et al. |
| 7,491,544 | B2 | 2/2009 | Canary et al. |
| 7,501,518 | B2 | 3/2009 | Chen et al. |
| 7,592,351 | B2 | 9/2009 | Sundermann et al. |
| 7,723,525 | B2 | 5/2010 | Crawford et al. |
| 7,863,293 | B2 | 1/2011 | Bridger et al. |
| 8,138,347 | B2 | 3/2012 | Knight et al. |
| 8,168,783 | B2 | 5/2012 | Kokubo et al. |
| 8,178,123 | B2 | 5/2012 | Pauletti et al. |
| 8,889,159 | B2 | 11/2014 | Cleary et al. |
| 8,906,682 | B2 | 12/2014 | June et al. |
| 9,119,790 | B2 | 9/2015 | Crowley et al. |
| 9,155,723 | B2 | 10/2015 | Jain et al. |
| 9,267,934 | B2 | 2/2016 | Singh et al. |
| 9,314,468 | B2 | 4/2016 | Clark et al. |
| 10,548,889 | B1 | 2/2020 | Brands |
| 10,610,527 | B2 | 4/2020 | Arbeit et al. |
| 10,953,003 | B2 | 3/2021 | Ragan et al. |

(Continued)

FOREIGN PATENT DOCUMENTS

| | | | |
|---|---|---|---|
| CN | 116789639 | A | 9/2023 |
| WO | WO1997009976 | A2 | 3/1997 |

(Continued)

OTHER PUBLICATIONS

"Common Terminology Criteria for Adverse Events (CTCAE), Version 4.0", U.S. Department of Health and Human Services, National Institutes of Health, National Cancer Institute, NIH Publication No. 09-5410, May 28, 2009, revised Jun. 2010, 96 pages.
"Nivolumab", DrugBank. Accession No. DB09035 (DB06132), Retrieved from: http://www.drugbank.ca/drugs/DB09035, Accessed on Nov. 29, 2018, pp. 1:14.
"Q3C—Tables and Lists, Guidance for Industry", U.S. Department of Health and Human Services, Food and Drug Administration, Center for Drug Evaluation and Research, Center for Biologics Evaluation and Research, https://www.fda.gov/downloads/Drugs/GuidanceComplianceRegulatoryInformation/Guidances/UCM073395.pdf, Aug. 2018, 10 pages.
"SciFinder®", Search Results, American Chemical Society (ACS), 2015, 39 pages.
"SciFinder®", Search Results, American Chemical Society (ACS), 2015, 9 pages.

(Continued)

*Primary Examiner* — Golam M Shameem
(74) *Attorney, Agent, or Firm* — Mintz Levin Cohn Ferris Glovsky and Popeo, P.C.

(57) ABSTRACT

The present invention relates to methods for synthesizing C-X-C receptor type 4 (CXCR4) inhibitor mavorixafor and to intermediates thereto.

11 Claims, No Drawings

(56) References Cited

U.S. PATENT DOCUMENTS

| | | | |
|---|---|---|---|
| 10,988,465 | B2 | 4/2021 | Bourque et al. |
| 11,045,461 | B2 | 6/2021 | Brands |
| 11,219,621 | B2 | 1/2022 | Arbeit et al. |
| 11,337,969 | B2 | 5/2022 | Arbeit |
| 11,357,742 | B2 | 6/2022 | Arbeit et al. |
| 11,672,793 | B2 | 6/2023 | Brands |
| 12,115,156 | B2 | 10/2024 | Brands |
| 12,285,424 | B2 | 4/2025 | Kelley et al. |
| 12,377,090 | B1 | 8/2025 | Kelley et al. |
| 2003/0220341 | A1 | 11/2003 | Bridger et al. |
| 2003/0232808 | A1 | 12/2003 | Kobayashi et al. |
| 2005/0209277 | A1 | 9/2005 | Crawford et al. |
| 2005/0227958 | A1 | 10/2005 | Wang et al. |
| 2007/0123538 | A1 | 5/2007 | Dunkle et al. |
| 2007/0167459 | A1 | 7/2007 | Habashita et al. |
| 2008/0045537 | A1 | 2/2008 | Gudmundsson et al. |
| 2008/0058353 | A1 | 3/2008 | Banks |
| 2008/0096861 | A1 | 4/2008 | Gudmundsson et al. |
| 2009/0203533 | A1 | 8/2009 | Munnes et al. |
| 2009/0247570 | A1 | 10/2009 | Mayer |
| 2009/0325877 | A1 | 12/2009 | Grunt et al. |
| 2010/0002272 | A1 | 1/2010 | Sato et al. |
| 2010/0022724 | A1 | 1/2010 | Jacobsen et al. |
| 2010/0028299 | A1 | 2/2010 | Einav et al. |
| 2010/0143301 | A1 | 6/2010 | Desai et al. |
| 2011/0206607 | A1 | 8/2011 | Olsson et al. |
| 2011/0293521 | A1 | 12/2011 | Hyde et al. |
| 2012/0041028 | A1 | 2/2012 | Cooper et al. |
| 2012/0141471 | A1 | 6/2012 | Salvino et al. |
| 2014/0275260 | A1 | 9/2014 | Kawale et al. |
| 2015/0004239 | A1 | 1/2015 | Cullen et al. |
| 2015/0301058 | A1 | 10/2015 | Schettini et al. |
| 2016/0089385 | A1 | 3/2016 | Sherman et al. |
| 2017/0090658 | A1 | 3/2017 | Park et al. |
| 2017/0137401 | A1 | 5/2017 | Cox et al. |
| 2017/0166591 | A1 | 6/2017 | Ojima et al. |
| 2017/0333436 | A1 | 11/2017 | Treon et al. |
| 2019/0030023 | A1 | 1/2019 | Arbeit et al. |
| 2019/0322671 | A1 | 10/2019 | Bourque et al. |
| 2020/0123150 | A1 | 4/2020 | Bourque et al. |
| 2020/0138804 | A1 | 5/2020 | Parasuraman et al. |
| 2021/0025895 | A1 | 1/2021 | Wang et al. |
| 2021/0127496 | A1 | 4/2021 | Tuominen et al. |
| 2021/0349099 | A1 | 11/2021 | Wang et al. |
| 2023/0346772 | A1 | 11/2023 | Kelley |
| 2025/0152575 | A1 | 5/2025 | Arbeit et al. |
| 2025/0228843 | A1 | 7/2025 | Brands |

FOREIGN PATENT DOCUMENTS

| | | | |
|---|---|---|---|
| WO | WO1999004794 | A1 | 2/1999 |
| WO | WO1999031264 | A1 | 6/1999 |
| WO | WO2000002870 | A1 | 1/2000 |
| WO | WO2000022599 | A1 | 4/2000 |
| WO | WO2000045814 | A1 | 8/2000 |
| WO | WO2000056729 | A1 | 9/2000 |
| WO | WO2001042241 | A1 | 6/2001 |
| WO | WO2002022600 | A2 | 3/2002 |
| WO | WO2002034745 | A1 | 5/2002 |
| WO | WO2002076948 | A1 | 10/2002 |
| WO | WO2003011277 | A2 | 2/2003 |
| WO | WO2003055876 | A1 | 7/2003 |
| WO | WO2003063794 | A2 | 8/2003 |
| WO | WO2004019973 | A1 | 3/2004 |
| WO | WO2004089925 | A1 | 10/2004 |
| WO | WO2004093817 | A2 | 11/2004 |
| WO | WO2004106328 | A1 | 12/2004 |
| WO | WO2004106493 | A2 | 12/2004 |
| WO | WO2005007623 | A2 | 1/2005 |
| WO | WO2005090308 | A1 | 9/2005 |
| WO | WO2005113554 | A2 | 12/2005 |
| WO | WO2006026703 | A2 | 3/2006 |
| WO | 2006039250 | A2 | 4/2006 |
| WO | WO2006036816 | A2 | 4/2006 |
| WO | WO2006078846 | A1 | 7/2006 |
| WO | WO2006096444 | A2 | 9/2006 |
| WO | WO2006122806 | A2 | 11/2006 |
| WO | WO2006138259 | A2 | 12/2006 |
| WO | WO2007008539 | A2 | 1/2007 |
| WO | WO2007016176 | A2 | 2/2007 |
| WO | WO2007022523 | A2 | 2/2007 |
| WO | WO2007027999 | A2 | 3/2007 |
| WO | WO2007044729 | A2 | 4/2007 |
| WO | WO2007053452 | A1 | 5/2007 |
| WO | WO2007070514 | A1 | 6/2007 |
| WO | WO2007084786 | A1 | 7/2007 |
| WO | WO2007087548 | A2 | 8/2007 |
| WO | WO2007087549 | A2 | 8/2007 |
| WO | WO2007129161 | A2 | 11/2007 |
| WO | WO2008039218 | A2 | 4/2008 |
| WO | WO2008109943 | A1 | 9/2008 |
| WO | WO2008118802 | A1 | 10/2008 |
| WO | WO2009026251 | A1 | 2/2009 |
| WO | WO-2009076408 | A2 | 6/2009 |
| WO | WO2009114512 | A1 | 9/2009 |
| WO | WO2009117710 | A2 | 9/2009 |
| WO | WO2011090760 | A1 | 7/2011 |
| WO | WO2011147026 | A2 | 12/2011 |
| WO | WO2012049277 | A1 | 4/2012 |
| WO | WO2012075362 | A2 | 6/2012 |
| WO | WO2012094703 | A1 | 7/2012 |
| WO | WO2015019284 | A2 | 2/2015 |
| WO | WO2015030853 | A1 | 3/2015 |
| WO | WO2015038887 | A1 | 3/2015 |
| WO | WO2015069770 | A1 | 5/2015 |
| WO | WO2015143012 | A1 | 9/2015 |
| WO | WO2015200341 | A1 | 12/2015 |
| WO | WO2016008976 | A1 | 1/2016 |
| WO | WO2016090434 | A1 | 6/2016 |
| WO | WO2016146261 | A1 | 9/2016 |
| WO | WO2016201425 | A1 | 12/2016 |
| WO | WO2017048702 | A1 | 3/2017 |
| WO | WO2017106328 | A1 | 6/2017 |
| WO | WO2017106332 | A1 | 6/2017 |
| WO | WO2017127811 | A1 | 7/2017 |
| WO | WO2017177230 | A1 | 10/2017 |
| WO | WO2017181073 | A1 | 10/2017 |
| WO | WO2017223229 | A1 | 12/2017 |
| WO | WO2017223239 | A1 | 12/2017 |
| WO | WO2017223243 | A1 | 12/2017 |
| WO | WO2018237158 | A1 | 12/2018 |
| WO | WO2019094392 | A1 | 5/2019 |
| WO | WO2019126106 | A1 | 6/2019 |
| WO | WO2019200223 | A1 | 10/2019 |
| WO | WO2020047410 | A1 | 3/2020 |
| WO | WO2023003862 | A1 | 1/2023 |
| WO | 2023059903 | A1 | 4/2023 |
| WO | WO2023172640 | A1 | 9/2023 |

OTHER PUBLICATIONS

Abi-Younes et al., "The Stromal Cell-Derived Factor-1 Chemokine Is a Potent Platelet Agonist Highly Expressed in Atherosclerotic Plaques", Circulation Research, Feb. 4, 2000, 86(2):131-138.

Acharyya et al., "A CXCL1 paracrine network links cancer chemoresistance and metastasis", Cell, Jul. 6, 2012, 150(1):165-178.

Aduro Biotech, Inc., "Safety and Efficacy of MIW815 (ADU-S100) +/- Ipilimumab in Patients with Advanced/Metastatic Solid Tumors or Lymphomas", ClinicalTrials.gov Identifier: NCT02675439, Retrieved from: https://clinicaltrials.gov/ct2/show/study/NCT02675439, Feb. 5, 2016, pp. 1-6.

Aeglea Biotherapeutics, "A Multiple Dose, Dose Escalation Trial of AEB1102 in Patients with Advanced Solid Tumors", ClinicalTrials.gov Identifier: NCT02561234, Retrieved on: https://clinicaltrials.gov/ct2/show/study/NCT02561234, Sep. 28, 2015, pp. 1-6.

Aeglea Biotherapeutics, "A Multiple Dose, Dose Escalation Trial of AEB1102 in Patients with AML or MDS", ClinicalTrials.gov Identifier: NCT02732184, Retrieved from: https://clinicaltrials.gov/ct2/show/study/NCT02732184, Apr. 8, 2016, pp. 1-6.

(56) References Cited

OTHER PUBLICATIONS

Agenus Inc., "AGEN-1884, an Anti-CTLA-4 Antibody, in Advanced Solid Cancers", ClinicalTrials.gov identifier: NCT02694822, Retrieved from: https://clinicaltrials.gov/ct2/show/study/NCT02694822, Mar. 1, 2016, pp. 1-7.
Aileron Therapeutics, "ALRN-6924 in Patients with Advanced Solid Tumors or Lymphomas", ClinicalTrials.gov identifier: NCT02264613, Retrieved from: https://clinicaltrials.gov/ct2/show/study/NCT02264613, Oct. 15, 2014, pp. 1-7.
Aileron Therapeutics, "Safety Study of ALRN-6924 in Patients with Acute Myeloid Leukemia or Advanced Myelodysplastic Syndrome", ClinicalTrials. gov identifier: NCT02909972, Retrieved from: https://clinicaltrials.gov/ct2/show/study/NCT02909972, Sep. 21, 2016, pp. 1-7.
Aiuti et al., "The Chemokine SDF-1 Is a Chemoattractant for Human CD34+ Hematopoietic Progenitor Cells and Provides a New Mechanism to Explain the Mobilization of CD34+ Progenitors to Peripheral Blood", Journal of Experimental Medicine, Jan. 6, 1997, 185(1):111-120.
ALX Oncology Inc., "A Study of ALX148 in Patients with Advanced Solid Tumors and Lymphoma", ClinicalTrials.gov identifier: NCT03013218, Retrieved from: https://clinicaltrials.gov/ct2/show/study/NCT03013218, Jan. 6, 2017, pp. 1-6.
Ami et al., "Lipase-catalyzed Kinetic Resolution of (+)-trans- and cis-2- Azidocycloalkanols", Bioscience, Biotechnology, and Biochemistry, 1999, 63(12):2150-2156.
An et al., "Solution Phase Combinatorial Chemistry. Discovery of 13- and 15- Membered Polyazapyridinocyclophane Libraries with Antibacterial Activity", Tetrahedron, 1998, 54(16):3999-4012.
Andtbacka et al., "X4P-001, an Orally Bioavailable CXCR4 Antagonist, Increase T Cell Infiltration in Human Metastatic Melanoma", The Society for Immunotherapy of Cancer Annual Meeting, National Harbor, Maryland, Nov. 8-12, 2017, 1 page.
Andtbacka et al., "X4P-001, an Orally Bioavailable CXCR4 Antagonist, Increases Immune Cell Infiltration and Tumor Inflammatory Status in the Microenvironment of Melanoma", The Society for Immunotherapy of Cancer Annual Meeting, Nov. 7-11, 2018, 3 pages.
AnorMed, "X4P-001 Product Page", Adis Insight, Retrieved from: https://adisinsight.springer.com/drugs/800017499, Mar. 20, 2019:1-5.
Arenberg et al., "The role of CXC chemokines in the regulation of angiogenesis in non-small cell lung cancer", Journal of Leukocyte Biology, Nov. 1997, 62(5):554-562.
Ayers et al., "IFN-gamma-related mRNA profile predicts clinical response to PD-1 blockade", The Journal of Clinical Investigation, Aug. 2017, 127(8):2930-2940.
Azijli et al., "New Developments in the Treatment of Metastatic Melanoma: Immune Checkpoint Inhibitors and Targeted Therapies", Anticancer Research, Apr. 2014, 34(4):1493-1505.
Baggiolini, "Chemokines and leukocyte traffic", Nature, Apr. 1998, 392(6676):565-568.
Balabanian et al., "Proper desensitization of CXCR4 is required for lymphocyte development and peripheral compartmentalization in mice", Blood, Jun. 14, 2012, 119(24):5722-5730.
Balabanian et al., "WHIM syndromes with different genetic anomalies are accounted for by impaired CXCR4 desensitization to CXCL 12", Blood, Mar. 15, 2005, 105(6):2449-2457.
Barniol-Xicota et al., "Direct reductive alkylation of amine hydrochlorides with aldehyde bisulfite adducts", Tetrahedron Letters, 2014, 55(15):2548-2550.
Bayer, "Phase I Study of BAY1436032 in IDH1-mutant Advanced Solid Tumors", ClinicalTrials. gov identifier: NCT02746081, Retrieved from: https://clinicaltrials.gov/ct2/show/study/NCT02746081, Apr. 21, 2016, pp. 1-8.
Berge et al., "Pharmaceutical Salts", Journal of Pharmaceutical Sciences, Jan. 1977, 66(1):1-19.
Blaak et al., "In vivo HIV-1 infection of CD45RA(+)CD4(+) T cells is established primarily by syncytium-inducing variants and correlates with the rate of CD4(+) T cell decline", Proceedings of the National Academy of Sciences of the United States of America, Feb. 1, 2000, 97(3):1269-1274.
Blanco et al., "The CXCR4 Antagonist AMD3100 Efficiently Inhibits Cell-Surface- Expressed Human Immunodeficiency Virus Type 1 Envelope-Induced Apoptosis", Antimicrobial Agents and Chemotherapy, Jan. 2000, 44(1):51-56.
Bleul et al., "B Lymphocyte Chemotaxis Regulated in Association with Microanatomic Localization, Differentiation State, and B Cell Receptor Engagement", Journal of Experimental Medicine, Mar. 2, 1998, 187(5):753-762.
Bohinjec, "Myelokathexis: Chronic Neutropenia with Hyperplastic Bone marrow and Hypersegmented Neutrophils in Two Siblings", Blut, Mar. 1981, 42(3):191-196.
Boutsikou et al., "Tumour necrosis factor, interferon-gamma and interleukins as predictive markers of antiprogrammed cell-death protein-1 treatment in advanced non-small cell lung cancer: a pragmatic approach in clinical practice", Therapeutic Advances in Medical Oncology, 2018, 10:1-8.
Bristol-Myers Squibb, "A Phase I Open Label Study of the Safety and Tolerability of Elotuzumab (BMS-901608) Administered in Combination with Either Lirilumab (BMS-986015) or Urelumab (BMS-663513) in Subjects with Multiple Myeloma", ClinicalTrials. gov identifier: NCT02252263, Retrieved from: https://clinicaltrials.gov/ct2/show/study/NCT02252263, Sep. 30, 2014, pp. 1-7.
Bristol-Myers Squibb, "An Investigational Immuno-Therapy Study of Experimental Medication BMS-986178 by Itself or in Combination with Nivolumab and/or Ipilimumab in Participants with Solid Cancers That Are Advanced or Have Spread", ClinicalTrials. gov identifier: NCT02737475, Retrieved from: https://clinicaltrials.gov/ct2/show/study/NCT02737475, Apr. 14, 2016, pp. 1-11.
Bristol-Myers Squibb, "An Investigational Immuno-Therapy Study of Experimental Medication BMS-986179 Given Alone and in Combination with Nivolumab", ClinicalTrials.gov identifier: NCT02754141, Retrieved from: https://clinicaltrials.gov/ct2/show/study/NCT02754141, Apr. 28, 2016, pp. 1-8.
Bristol-Myers Squibb, "An Investigational Immuno-Therapy Study to Determine the Safety and Effectiveness of Nivolumab and Daratumumab in Patients with Multiple Myeloma", ClinicalTrials. gov identifier: NCT01592370, Retrieved from: https://clinicaltrials.gov/ct2/show/study/NCT01592370, May 7, 2012, pp. 1-9.
Bristol-Myers Squibb, "An Investigational Immuno-Therapy Study to Evaluate the Safety and Effectiveness of Experimental Medication BMS-986207 by Itself and in Combination With Nivolumab in Solid Cancers That Are Advanced or Have Spread", ClinicalTrials. gov identifier: NCT02913313, Retrieved from: https://clinicaltrials.gov/ct2/show/study/NCT02913313, Sep. 23, 2016, pp. 1-9.
Bristol-Myers Squibb, "An Investigational Immuno-Therapy Study to Investigate the Safety and Effectiveness of Nivolumab, and Nivolumab Combination Therapy in Virus-associated Tumors (CheckMate358)", ClinicalTrials.gov identifier: NCT02488759, Retrieved from: https://clinicaltrials.gov/ct2/show/study/NCT02488759, Jul. 2, 2015, pp. 1-7.
Bristol-Myers Squibb, "Safety and Efficacy Study of Ulocuplumab and Nivolumab in Subjects with Solid Tumors (CXCessoR4)", ClinicalTrials.gov identifier: NCT02472977, Retrieved from: https://clinicaltrials.gov/ct2/show/study/NCT02472977, Jun. 16, 2015, pp. 1-7.
Broxmeyer et al., "Effects of in vivo treatment with PIXY321 (GM-CSF/IL-3 fusion protein) on proliferation kinetics of bone marrow and blood myeloid progenitor cells in patients with sarcoma", Experimental Hematology, Apr. 1995, 23(4):335-340.
Broxmeyer, "A Whim satisfactorily addressed", Blood, Apr. 10, 2014, 123(15):2286-2288.
Burger et al., "Chronic Lymphocytic Leukemia B Cells Express Functional CXCR4 Chemokine Receptors That Mediate Spontaneous Migration Beneath Bone Marrow Stromal Cells", Blood, Dec. 1, 1999, 94(11):3658-3667.
Canadian Cancer Trials Group, "Reolysin Combined with Docetaxel and Prednisone or Docetaxel and Prednisone Alone in Metastatic Castration Resistant Prostate Cancer", ClinicalTrials. gov identifier: NCT01619813, Retrieved from: https://clinicaltrials.gov/ct2/show/study/NCT01619813, Jun. 14, 2012, pp. 1-8.

(56) References Cited

OTHER PUBLICATIONS

Canadian Cancer Trials Group, "Reolysin in Combination with FOLFOX6 and Bevacizumab or FOLFOX6 and Bevacizumab Alone in Metastatic Colorectal Cancer", ClinicalTrials. gov identifier: NCT01622543, Retrieved from: https://clinicaltrials.gov/ct2/show/study/NCT01622543, Mar. 25, 2019, pp. 1-8.
Cao et al., "Effect of Low-Dose Ritonavir on the Pharmacokinetics of the CXCR4 Antagonist AMD070 in Healthy Volunteers", Antimicrobial Agents and Chemotherapy, May 2008, 52(5):1630-1634.
Catalano et al., "Synthesis of a novel tricyclic 1,2,3,4,4a,5,6,10b-octahydro-1,10- phenanthroline ring system and CXCR4 antagonists with potent activity against HIV-1", Bioorganic & Medicinal Chemistry Letters, Apr. 1, 2010, 20(7):2186-2190.
Celgene, "A Safety and Efficacy Study of Oral AG-120 Plus Subcutaneous Azacitidine and Oral AG-221 Plus Subcutaneous Azacitidine in Subjects with Newly Diagnosed.Acute Myeloid Leukemia (AML)", ClinicalTrials. gov identifier: NCT02677922, Retrieved from: https://clinicaltrials.gov/ct2/show/study/NCT02677922, Feb. 9, 2016, pp. 1-11.
Celgene, "A Study of CC-90002 in Subjects with Acute Myeloid Leukemia (AML) and High-risk Myelodysplastic Syndrome (MDS)", ClinicalTrials.gov identifier: NCT02641002, Retrieved from: https://clinicaltrials.gov/ct2/show/study/NCT02641002, Dec. 29, 2015, pp. 1-7.
Celgene, "An Efficacy and Safety Study of AG-221 (CC-90007) Versus Conventional Care Regimens in Older Subjects with Late Stage Acute Myeloid Leukemia Harboring an Isocitrate Dehydrogenase 2 Mutation (IDHENTIFY)", ClinicalTrials.gov identifier: NCT02577406, Retrieved from: https://clinicaltrials.gov/ct2/show/study/NCT02577406, Oct. 16, 2015, pp. 1-12.
Celldex Therapeutics, "A Dose Escalation and Cohort Expansion Study of Anti-CD27 (Varlilumab) and Anti-PD-1 (Nivolumab) in Advanced Refractory Solid Tumors", ClinicalTrials. gov identifier: NCT02335918, Retrieved from: https://clinicaltrials.gov/ct2/show/study/NCT02335918, Jan. 12, 2015, pp. 1-9.
Celldex Therapeutics, "A Study of CDX-1127 (Varlilumab) in Patients with Select Solid Tumor Types or Hematologic Cancers", ClinicalTrials. gov identifier: NCT01460134, Retrieved from: https://clinicaltrials.gov/ct2/show/study/NCT01460134, Oct. 26, 2011, pp. 1-9.
Centre Leon Berard, "Evaluation of Safety and Activity of an Anti-PDL 1 Antibody (DURVALUMAB) Combined With Csf-Ir Tki (Pexidartinib) in Patients with Metastatic/Advanced Pancreatic or Colorectal Cancers (MEDIPLEX)", ClinicalTrials. gov Identifier: NCT02777710, Retrieved from: https://clinicaltrials.gov/ct2/show/study/NCT02777710, May 19, 2016, pp. 1-10.
Chen et al., "CXCR4 Inhibition in Tumor Microenvironment Facilitates Anti- Programmed Death Receptor-1 Immunotherapy in Sorafenib-Treated Hepatocellular Carcinoma in Mice", Hepatology, May 2015, 61(5):1591-1602.
Choueiri et al., "Combination Therapy with the CXCR4 Inhibitor X4P-001 and Nivolumab Demonstrates Preliminary Anti-tumor Activity in RCC Patients that are Unresponsive to Nivolumab Alone", ESMO Congress, Oct. 19-23, 2018, 1 page.
Choueiri et al., "Systemic Therapy for Metastatic Renal-Cell Carcinoma", The New England Journal of Medicine, Jan. 26, 2017, 376(4):354-366.
Clark, "Rationale for targeted therapies and potential role of pazopanib in advanced renal cell carcinoma", Biologics: Targets and Therapy, Aug. 2010, 9(4):187-197.
Cohen et al., "Description and outcome of a cohort of 8 patients with WHIM syndrome from the French Severe Chronic Neutropenia Registry", Orphanet Journal of Rare Diseases, 2012, 7(71):1-14.
Cold Genesys, Inc., "Safety and Efficacy of CG0070 Oncolytic Virus Regimen for High Grade NMIBC After BCG Failure (BOND2)", ClinicalTrials.gov identifier: NCT02365818, Retrieved from: https://clinicaltrials.gov/ct2/show/study/NCT02365818, Feb. 19, 2015, pp. 1-9.
Comba et al., "Catalytic Aziridination of Styrene with Copper Complexes of Substituted 3,7-Diazabicyclo[3.3.1]nonanones", European Journal of Inorganic Chemistry, 2003, 2003(9):1711-1718.
Connolly et al., "Complexities of TGF-Beta Targeted Cancer Therapy", International Journal of Biological Sciences, 2012, 8(7):964-978.
Connor et al., "Human Immunodeficiency Virus Type 1 Variants with Increased Replicative Capacity Develop during the Asymptomatic Stage before Disease Progression", Journal of Virology, Jul. 1994, 68(7):4400-4408.
Courtney et al., "Optimizing Recent Advances in Metastatic Renal Cell Carcinoma", Current Oncology Reports, May 2009, 11(3):218-226.
Crawford et al., "AMD070, a CXCR4 Chemokine Receptor Antagonist: Practical Large-Scale Laboratory Synthesis", Organic Process Research & Development, 2008, 12(5):823-830.
Crump et al., "Solution structure and basis for functional activity of stromal cell-derived factor-1; dissociation of CXCR4 activation from binding and inhibition of HIV-1", The EMBO Journal, 1997, 16(23):6996-7007.
Dale et al., "An update on the diagnosis and treatment of chronic idiopathic neutropenia", Current Opinion in Hematology, Jan. 2017, 24(1):46-53.
Dale et al., "Effects of Granulocyte-Macrophage Colony-Stimulating Factor (GM-CSF) on Neutrophil Kinetics and Function in Normal Human Volunteers", American Journal of Hematology, 1998, 57(1):7-15.
Dale et al., "Results of a phase 2 trial of an oral CXCR4 antagonist, mavorixafor, for treatment of WHIM syndrome", Blood, Dec. 24, 2020, 136(26):2994-3003.
Dale et al., "The CXCR4 antagonist plerixafor is a potential therapy for myelokathexis, WHIM syndrome", Blood, Nov. 3, 2011, 118(18):4963-4966.
Dale et al., "The Severe Chronic Neutropenia International Registry: 10-Year Follow- up Report", Supportive Cancer Therapy, Jul. 2005, 3(4):220-31.
D'Alterio et al., "Inhibition of stromal CXCR4 impairs development of lung metastases", Cancer Immunology, Immunotherapy, 2012, 61(10):1713-1720.
Dana-Farber Cancer Institute, "LY3022855 With BRAF/MEK Inhibition in Patients with Melanoma", ClinicalTrials.gov identifier: NCT03101254, Retrieved from: https://clinicaltrials.gov/ct2/show/study/NCT03101254, Apr. 5, 2017, pp. 1-9.
Debnath et al., "Small Molecule Inhibitors of CXCR4", Theranostics, 2013, 3(1):47-75.
DePrimo et al., "Circulating protein biomarkers of pharmacodynamic activity of sunitinib in patients with metastatic renal cell carcinoma: modulation of VEGF and VEGF-related proteins", Journal of Translational Medicine, 2007, 5(32):1-11.
Doranz et al., "Chemokine Receptors as Fusion Cofactors for Human Immunodeficiency Virus Type 1 (HIV-1)", Immunologic Research, 1997, 16(1):15-28.
Dorwald, "IX: Side Reactions in Organic Synthesis: A Guide to Successful Synthesis Design", Wiley-VCH Verlag GmbH & Co. KGaA, 2005, pp. 1-16, 41.
Dotta et al., "Clinical and Genetic Features of Warts, Hypogammaglobulinemia, Infections and Myelokathexis (WHIM) syndrome", Current Molecular Medicine, 2011, 11(4):317-325.
Duda et al., "CXCL12 (SFG1alpha)-CXCR4/CXCR7 Pathway Inhibition: An Emerging Sensitizer for Anti-Cancer Therapies?", Clinical Cancer Research, Apr. 15, 2011, 17(8):2074-2080.
Dudley et al., "CD8+ enriched "young" tumor infiltrating lymphocytes can mediate regression of metastatic melanoma", Clinical Cancer Research, Dec. 15, 2010, 16(24):6122-6131.
Egberink et al., "Bicyclams, Selective Antagonists of the Human Chemokine Receptor CXCR4, Potently Inhibit Feline Immunodeficiency Virus Replication", Journal of Virology, Aug. 1999, 73(8):6346-6352.
Eli Lilly and Company, "A Study of LY3022855 in Combination with Durvalumab or Tremelimumab in Participants with Advanced Solid Tumors", ClinicalTrials.gov identifier: NCT02718911, Retrieved from: https://clinicaltrials.gov/ct2/show/study/NCT02718911, Mar. 24, 2016, pp. 1-7.

(56) References Cited

OTHER PUBLICATIONS

Eli Lilly and Company, "A Study of LY3321367 Alone or With LY3300054 in Participants with Advanced Relapsed/Refractory Solid Tumors", ClinicalTrials.gov identifier: NCT03099109, Retrieved from: https://clinicaltrials.gov/ct2/show/study/NCT03099109, Apr. 4, 2017, pp. 1-9.
EMD Serono Research & Development Institute, Inc., "MSB0011359C (M7824) in Metastatic or Locally Advanced Solid Tumors", ClinicalTrials.gov Identifier: NCT02517398, Retrieved from: https://clinicaltrials.gov/ct2/show/study/NCT02517398, Aug. 7, 2015, pp. 1-6.
Facciabene et al., "Tumour hypoxia promotes tolerance and angiogenesis via CCL28 and Treg cells", Nature, Jul. 14, 2011, 475(7355):226-230.
Fedyk et al., "Maturation decreases responsiveness of human bone marrow B lineage cells to stromal-derived factor 1 (SDF-1)", Journal of Leukocyte Biology, Oct. 1999, 66(4):667-673.
Feig et al., "Targeting CXCL 12 from FAP-expressing carcinoma-associated fibroblasts synergizes with anti-PD-L 1 immunotherapy in pancreatic cancer", PNAS, Dec. 10, 2013, 110(50):20212-20217.
Finke et al., "MDSC as a Mechanism of Tumor Escape from Sunitinib Mediated Anti- Angiogenic Therapy", International Immunopharmacology, Jul. 2011, 11(7):853-858.
Forty Seven, Inc., "CAMELLIA: Anti-CD47 Antibody Therapy in Haematological Malignancies", ClinicalTrials. gov Identifier: NCT02678338, Retrieved from: https://clinicaltrials.gov/ct2/show/study/NCT02678338, Feb. 9, 2016, pp. 1-6.
Forty Seven, Inc., "Trial of Hu5F9-G4 in Combination With Rituximab in Relapsed/Refractory B-cell Non-Hodgkin's Lymphoma", ClinicalTrials.gov identifier: NCT02953509, Retrieved from: https://clinicaltrials.gov/ct2/show/study/NCT02953509, Nov. 2, 2016, pp. 1-8.
Gacche, "Compensatory angiogenesis and tumor refractoriness", Oncogenesis, Jun. 1, 2015, 4(6):e153, pp. 1-8.
Gale et al., "Chemokines: extracellular messengers for all occasions? ", BioEssays, 1999, 21(1):17-28.
Galsky et al., "A phase I Trial of LY2510924, a CXCR4 Peptide Antagonist, in Patients with Advanced Cancer", Clinical Cancer Research, Jul. 1, 2014, 20(13):3581-3588.
Gao et al., "Intratumoral Balance of Regulatory and Cytotoxic T cells is Associated With Prognosis of Hepatocellular Carcinoma After Resection", Journal of Clinical Oncology, Jun. 20, 2007, 25(18):2586-2593.
Gassenmaier et al., "CXC Chemokine Receptor 4 is Essential for Maintenance of Renal Cell Carcinoma-Initiating Cells and Predicts Metastasis", Stem Cells, 2013, 31(8):1467-1476.
Genelux Corporation, "GL-ONC1 Oncolytic Immunotherapy in Patients With Recurrent or Refractory Ovarian Cancer", ClinicalTrials.gov identifier: NCT02759588, Retrieved from: https://clinicaltrials.gov/ct2/show/study/NCT02759588, May 3, 2016, pp. 1-8.
Genelux GmbH, "A Study of GL-ONC1, an Oncolytic Vaccinia Virus, in Patients With Advanced Peritoneal Carcinomatosis", ClinicalTrials.gov Identifier: NCT01443260, Retrieved from: https://clinicaltrials.gov/ct2/show/study/NCT01443260, Sep. 29, 2011, pp. 1-6.
Genzyme, a Sanofi Company, "Safety and Efficacy Study of GC1008 to Treat Renal Cell Carcinoma or Malignant Melanoma", ClinicalTrials.gov identifier: NCT00356460, Retrieved from: https://clinicaltrials.gov/ct2/show/study/NCT00356460, Jul. 26, 2006, pp. 1-10.
Gilead Sciences, "Study of Magrolimab (Hu5F9-G4) in Combination With Cetuximab in Participants With Solid Tumors and Advanced Colorectal Cancer", ClinicalTrials.gov Identifier: NCT02953782, Retrieved from: https://clinicaltrials.gov/ct2/show/study/NCT02953782, Nov. 3, 2016, pp. 1-17.
Glaspy et al., "Peripheral Blood Progenitor Cell Mobilization Using Stem Cell Factor in Combination With Filgrastim in Breast Cancer Patients", Blood, Oct. 15, 1997, 90(8):2939-2951.
Glaxosmithkline, "Dose Escalation and Expansion Study of GSK3359609 in Subjects With Selected Advanced Solid Tumors (INDUCE-1)", ClinicalTrials.gov identifier: NCT02723955, Retrieved from: https://clinicaltrials.gov/ct2/show/study/NCT02723955, Mar. 31, 2016, pp. 1-25.
Glaxosmithkline, "GSK3174998 Alone or With Pembrolizumab in Subjects With Advanced Solid Tumors (ENGAGE-1)", ClinicalTrials.gov: NCT02528357, Retrieved from: https://clinicaltrials.gov/ct2/show/study/NCT02528357, Aug. 19, 2015, pp. 1-11.
Gonzalo et al., "Critical involvement of the chemotactic axis CXCR4/stromal cell-derived factor-1 alpha in the inflammatory component of allergic airway disease", Journal of Immunology, 2000, 165(1):499-508.
Gudmundsson et al., Amine substituted N-(1H-benzimidazol-2ylmethyl)-5,6,7,8-tetrahydro-8-quino-linamines as CXCR4 antagonists with potent activity against HIV-Bioorganic & Medicinal Chemistry Letters, 2009, 19(17):5048-5052.
Gulino et al., "Altered leukocyte response to CXCL 12 in patients with warts hypogammaglobulinemia, infections, myelokathexis (WHIM) syndrome", Blood, Jul. 15, 2004, 104(2):444-452.
H. Lee Moffitt Cancer Center and Research Institute, "Combining PD-1 Blockade, CD137 Agonism and Adoptive Cell Therapy for Metastatic Melanoma", ClinicalTrials.gov identifier: NCT02652455, Retrieved from: https://clinicaltrials.gov/ct2/show/study/NCT02652455, Jan. 11, 2016, pp. 1-9.
Hainsworth et al., "A Randomized, Open-Label Phase 2 Study of the CXCR4 Inhibitor C107|LY2510924 in Combination with Sunitinib Versus Sunitinib Alone in Patients with Metastatic Renal Cell Carcinoma (RCC)", Targeted Oncology, 2016, 11(5):643-653.
Hamid et al., "Safety and Tumor Responses with Lambrolizumab (Anti-PD-1) in Melanoma", The New England Journal of Medicine, Jul. 11, 2013, 369(2):134-144.
Hendrix et al., "Pharmacokinetics and Safety of AMD-3100, a Novel Antagonist of the CXCR-4 Chemokine Receptor, in Human Volunteers", Antimicrobial Agents and Chemotherapy, Jun. 2000, 44(6):1667-1673.
Hendrix et al., "Safety, Pharmacokinetics, and Antiviral Activity of AMD3100, a Selective CXCR4 Receptor Inhibitor, in HIV-1 Infection", Journal of Acquired Immune Deficiency Syndromes, Oct. 1, 2004, 37(2):1253-1262.
Hernandez et al., "Mutations in the chemokine receptor gene CXCR4 are associated with WHIM syndrome, a combined immunodeficiency disease", Nature Genetics, May 2003, 34(1):70-74.
Hesselgesser et al., "CD4-independent association between HIV-1 gp120 and CXCR4: functional chemokine receptors are expressed in human neurons", Current Biology, 1997, 7(2):112-121.
Hesselgesser et al., "Neuronal apoptosis induced by HIV-1 gp120 and the chemokine SDF-1 alpha is mediated by the chemokine receptor CXCR4", Current Biology, 1998, 8(10):595-598.
Highfill et al., "Disruption of CXCR2-Mediated MDSC Tumor Trafficking Enhances Anti-PD1 Efficacy", Science Translational Medicine, May 21, 2014, 6(237):1-13.
Hughes et al., "HIF-2alpha downregulation in the absence of functional VHL is not sufficient for renal cell differentiation", Cancer Cell International, Jun. 28, 2007,7(13):1-11.
Husain et al., "Tumor-Derived Lactate Modifies Antitumor Immune Response: Effect on Myeloid-Derived Suppressor Cells and NK Cells", The Journal of Immunology, Aug. 1, 2013, 191(3):1486-1495.
Immutep Australia Pty. Ltd., "Phase 1 Study of IMP321 (Eftilagimod Alpha) Adjuvant to Anti-PD-1 Therapy in Unresectable or Metastatic Melanoma (TACTI-mel)", ClinicalTrials.gov identifier NCT02676869, https://clinicaltrials.gov/ct2/show/study/NCT02676869, First Posted: Feb. 8, 2016, 6 pages.
Immutep S.A., "IMP321 (Eftilagimod Alpha) as Adjunctive to a Standard Chemotherapy Paclitaxel Metastatic Breast Carcinoma", ClinicalTrials.gov Identifier: NCT02614833, Retrieved from: https://clinicaltrials.gov/ct2/show/study/NCT02614833, Nov. 25, 2015, pp. 1-9.
Immutep S.A., "IMP321 Plus First-line Paclitaxel in Metastatic Breast Carcinoma", ClinicalTrials.gov Identifier: NCT00349934, Retrieved from: https://clinicaltrials.gov/ct2/show/study/NCT00349934, Jul. 10, 2006, pp. 1-7.
Incyte Biosciences International Sarl, "An Open-Label, Dose-Escalation, Safety Study of INCAGN01876 in Subjects With Advanced or Metastatic Solid Tumors", ClinicalTrials.gov Identifier: NCT02697591, Retrieved from: https://clinicaltrials.oov/ct2/show/study/NCT02697591, Mar. 3, 2016, pp. 1-6.

(56) References Cited

OTHER PUBLICATIONS

Incyte Biosciences International Sarl, "Phase 1/2 Study Exploring the Safety, Tolerability, and Efficacy of INCAGN01876 Combined With Immune Therapies in Advanced or Metastatic Malignancies", ClinicalTrials.gov Identifier: NCT03126110, Retrieved from: https://clinicaltrials.gov/ct2/show/study/NCT03126110, Apr. 24, 2017, pp. 1-7.
Innate Pharma, "Combination Study of IPH2201 With Ibrutinib in Patients With Relapsed, Refractory or Previously Untreated Chronic Lymphocytic Leukemia", ClinicalTrials.gov identifier: NCT02557516, Retrieved from: https://clinicaltrials.gov/ct2/show/study/NCT02557516, Sep. 23, 2015, pp. 1-6.
Innate Pharma, "Efficacy Study of Anti-KIR Monoclonal Antibody as Maintenance Treatment in Acute Myeloid Leukemia (EFFIKIR) (EFFIKIR)", ClinicalTrials.gov identifier: NCT01687387, Retrieved from: https://clinicaltrials.gov/ct2/show/study/NCT01687387, Sep. 18, 2012, pp. 1-9.
Innate Pharma, "Study of IPH4102 in Patients With Relapsed/Refractory Cutaneous T- cell Lymphomas (CTCL)", ClinicalTrials.gov identifier: NCT02593045, Retrieved from: https://clinicaltrials.gov/ct2/show/study/NCT02593045, Oct. 30, 2015, pp. 1-6.
Innate Pharma, "Study of Monalizumab and Cetuximab in Patients With Recurrent or Metastatic Squamous Cell Carcinoma of the Head and Neck", ClinicalTrials.gov identifier: NCT02643550, Retrieved from: https://clinicaltrials.gov/ct2/show/study/NCT02643550, Dec. 31, 2015, pp. 1-9.
Innate Pharma, "Study on the Anti-tumor Activity, Safety and Pharmacology of IPH2101 in Patients With Smoldering Multiple Myeloma (KIRMONO)", ClinicalTrials.gov identifier: NCT01222286, Retrieved from: https://clinicaltrials.gov/ct2/show/study/NCT01222286, Oct. 18, 2010, pp. 1-7.
Innate Pharma, "Study on the Safety, Anti-tumor Activity and Pharmacology of IPH2101 Combined With Lenalidomide in Patients With Multiple Myeloma Experiencing a First or Second Relapse (KIRIMID)", ClinicalTrials.gov identifier: NCT01217203, Retrieved from: https://clinicaltrials.gov/ct2/show/study/NCT01217203, Oct. 8, 2010, pp. 1-7.
International Preliminary Report on Patentability received for PCT Application No. PCT/US2002/041407, completion on Jul. 17, 2003, 4 pages.
International Preliminary Report on Patentability received for PCT Application No. PCT/US2004/015977, completion on Apr. 1, 2006, 4 pages.
International Preliminary Report on Patentability received for PCT Application No. PCT/US2016/066634, completion on Jan. 26, 2017, 14 pages.
International Preliminary Report on Patentability received for PCT Application No. PCT/US2016/066639, mailed on Feb. 16, 2017, 10 pages.
International Preliminary Report on Patentability received for PCT Application No. PCT/US2016/068394, mailed on Mar. 3, 2017, 10 pages.
International Search Report and Written Opinion received for PCT Application No. PCT/US2017/014578, mailed on Apr. 4, 2017, 12 pages.
International Search Report and Written Opinion received for PCT Application No. PCT/US2017/026819, mailed on Jul. 21, 2017, 10 pages.
International Search Report and Written Opinion received for PCT Application No. PCT/US2018/038776, mailed on Nov. 20, 2018, 10 pages.
International Search Report and Written Opinion received for PCT Application No. PCT/US2018/059482, mailed on Jan. 17, 2019, 9 pages.
International Search Report and Written Opinion received for PCT Application No. PCT/US2018/066141, mailed on Mar. 8, 2019, 8 pages.
International Search Report and Written Opinion received for PCT Application No. PCT/US2019/027169, mailed on Jul. 3, 2019, 11 pages.
International Search Report and Written Opinion received for PCT Application No. PCT/US2019/049065, mailed on Nov. 15, 2019, 10 pages.
International Search Report and Written Opinion received for PCT Application No. PCT/US2020/066099, mailed on Mar. 23, 2021, 9 pages.
International Search Report and Written Opinion received for PCT Application No. PCT/US2021/021713, mailed on May 18, 2021, 11 pages.
International Search Report and Written Opinion received for PCT Application No. PCT/US2022/046094, mailed on Jan. 10, 2023, 10 pages.
International Search Report and Written Opinion received for PCT Application No. PCT/US2023/016451, mailed on Aug. 4, 2023, 15 pages.
International Search Report received for PCT Application No. PCT/US2002/029372, completion on Jul. 20, 2004, 3 pages.
International Search Report received for PCT Application No. PCT/US2004/011328, completion on Sep. 28, 2004, 1 page.
International Search Report received for PCT Application No. PCT/US2004/012627, completion on Nov. 10, 2004, 2 pages.
International Search Report received for PCT Application No. PCT/US2004/015977, completed on Jun. 22, 2005, 2 pages.
International Search Report received for PCT Application No. PCT/US2005/034491, dated Jan. 11, 2006, 1 page.
International Search Report received for PCT Application No. PCT/US2005/034950, dated May 10, 2006, 3 pages.
International Search Report received for PCT Application No. PCT/US2005/08268, completion on May 13, 2005, 3 pages.
Ishii et al., "Expression of Stromal Cell-Derived Factor-1/Pre-B Cell Growth-Stimulating Factor Receptor, CXC Chemokine Receptor 4, on CD34+ Human Bone Marrow Cells Is a Phenotypic Alteration for Committed Lymphoid Progenitors", The Journal of Immunology, 1999, 163(7):3612-3620.
Iwakura et al., "Abstract #1127: AMD-3100, a CXCR4 Antagonist, Augments Incorporation of Bone Marrow—Derived Endothelial Progenitor Cells into Sites of Myocardial Neovascularization", Poster Board #-Session: 293-I, Blood, Nov. 16, 2002, 100(11):293a-294a.
Jackson et al., "Regeneration of ischemic cardiac muscle and vascular endothelium by adult stem cells", The Journal of Clinical Investigation, Jun. 11, 2001, 107(11):1395-1402.
Jennerex Biotherapeutics, "A Study of Recombinant Vaccinia Virus to Treat Malignant Melanoma", ClinicalTrials.gov identifier: NCT00429312, Retrieved from: https://clinicaltrials.gov/ct2/show/study/NCT00429312, Jan. 31, 2007, pp. 1-7.
Jounce Therapeutics, Inc., "JTX-2011 Alone and in Combination With Anti-PD-1 or Anti-CTLA-4 in Subjects With Advanced and/or Refractory Solid Tumors (ICONIC)", ClinicalTrials.gov identifier: NCT02904226, Retrieved from: https://clinicaltrials.gov/ct2/show/study/NCT02904226, Sep. 16, 2016, pp. 1-11.
Kawai et al., "Enhanced function with decreased internalization of carboxy-terminus truncated CXCR4 responsible for WHIM syndrome", Experimental Hematology, Apr. 2005, 33(4):460-468.
Kawai et al., "WHIM syndrome myelokathexis reproduced in the NOD/SCID mouse xenotransplant model engrafted with healthy human stem cells transduced with C-terminus-truncated CXCR4", Blood, Jan. 1, 2007, 109(1):78-84.
Kawai et al., "WHIM Syndrome: Congenital Immune Deficiency Disease", Current Opinion in Hematology, Jan. 2009, 16(1):20-26.
Kim et al., "CXCR4 Signaling Regulates Metastasis of Chemoresistant Melanoma Cells by a Lymphatic Metastatic Niche", Cancer Research, Dec. 15, 2010, 70(24):10411-10421.
King et al., "Rapid mobilization of murine hematopoietic stem cells with enhanced engraftment properties and evaluation of hematopoietic progenitor cell mobilization in rhesus monkeys by a single injection of SB-251353, a specific truncated form of the human CXC chemokine GRO beta", Blood, Mar. 15, 2001, 97(6):1534-1542.
Kirkland et al., "Quantitation of Mafosfamide-Resistant Pre-Colony-Forming Units in Allogeneic Bone Marrow Transplantation: Relationship With Rate of Engraftment and Evidence for Long-Lasting Reduction in Stem Cell Numbers", Blood, May 1, 1996, 87(9):3963-3969.

(56) References Cited

OTHER PUBLICATIONS

Kocher et al., "Neovascularization of ischemic myocardium by human bone-marrow-derived angioblasts prevents cardiomyocyte apoptosis, reduces remodeling and improves cardiac function", Nature Medicine, Apr. 2001, 7(4):430-436.

Lagane et al., "CXCR4 dimerization and beta-arrestin-mediated signaling account for the enhanced chemotaxis to CXCL12 in WHIM syndrome", Blood, Jul. 1, 2008, 112(1):34-44.

Langan et al., "Liver Directed Therapy for Renal Cell Carcinoma", Journal of Cancer, 2012, 3:184-190.

Lapidot et al., "Current understanding of stem cell mobilization: The roles of chemokines, proteolytic enzymes, adhesion molecules, cytokines, and stromal cells", Experimental Hematology, 2002,30(9):973-981.

Lapidot et al., "The essential roles of the chemokine SDF-1 and its receptor CXCR4 in human stem cell homing and repopulation of transplanted immune-deficient NOD/SCID and NOD/SCID/B2m(null) mice", Leukemia, 2002, 16:1992-2003.

Lataillade et al., "Chemokine SDF-1 enhances circulating CD34(+) cell proliferation in synergy with cytokines: possible role in progenitor survival", Blood, Feb. 1, 2000, 95(3):756-768.

Leap Therapeutics, Inc., "Phase 1 Open-label Study of TRX518 Monotherapy and TRX518 in Combination With Gemcitabine, Pembrolizumab, or Nivolumab", ClinicalTrials.gov Identifier: NCT02628574, Retrieved from: https://clinicaltrials.gov/ct2/show/study/NCT02628574, Dec. 11, 2015, pp. 1-8.

Leap Therapeutics, Inc., "Trial of TRX518 (Anti-GITR mAb) in Stage III or IV Malignant Melanoma or Other Solid Tumors (TRX518-001)", ClinicalTrials.gov Identifier: NCT01239134, Retrieved from: https://clinicaltrials.gov/ct2/show/study/NCT01239134, Nov. 11, 2010, pp. 1-8.

Lee et al., "Coreceptor/chemokine receptor expression on human hematopoietic cells: biological implications for human immunodeficiency virus-type 1 infection", Blood, Feb. 15, 1999, 93(4):1145-1156.

Li et al., "Design, synthesis, and structure-activity-relationship of a novel series of CXCR4 antagonists", European Journal of Medicinal Chemistry, 2018, 149:30-44.

Liu et al., "Homozygous defect in HIV-1 coreceptor accounts for resistance of some multiply-exposed individuals to HIV-1 infection", Cell, Aug. 9, 1996, 86:367-377.

Lord et al., "Mobilization of Early Hematopoietic Progenitor Cells With BB-10010: A Genetically Engineered Variant of Human Macrophage Inflammatory Protein-1 alpha", Blood, Jun. 15, 1995,85(12):3412-3415.

Lu et al., "Direct N-Alkylation/Fluoroalkylation of Amines Using Carboxylic Acids via Transition-Metal-Free Catalysis", Advanced Synthesis & Catalysis, Oct. 2020, 362(19), 8 pages.

Ludwig Institute for Cancer Research, "A Phase 1/2 Study of Motolimod (VTX-2337) and MEDI4736 in Subjects With Recurrent, Platinum-Resistant Ovarian Cancer for Whom Pegylated Liposomal Doxorubicin (PLO) is Indicated", ClinicalTrials.gov Identifier: NCT02431559, Retrieved from: https://clinicaltrials.gov/ct2/show/study/NCT02431559, May 1, 2015, pp. 1-9.

Ludwig Institute for Cancer Research, "A Phase 1/2 Study to Investigate the Safety, Biologic and Anti-tumor Activity of ONCOS-102 in Combination With Durvalumab in Subjects With Advanced Peritoneal Malignancies", ClinicalTrials.gov Identifier: NCT02963831, Retrieved from: https://clinicaltrials.gov/ct2/show/study/NCT02963831, Nov. 15, 2016, pp. 1-8.

Lukacs et al., "AMD3100, a CxCR4 antagonist, attenuates allergic lung inflammation and airway hyperreactivity", American Journal of Pathology, Apr. 2002, 160(4):1353-1360.

Lycera Corp., "Study of LYC-55716 in Adult Subjects With Locally Advanced or Metastatic Cancer", ClinicalTrials.gov Identifier: NCT02929862, Retrieved from: https://clinicaltrials.gov/ct2/show/study/NCT02929862, Oct. 11, 2016, pp. 1-6.

M.D. Anderson Cancer Center, "Lirilumab and Azacitidine in Treating Patients With Refractory or Relapsed Acute Myeloid Leukemia", ClinicalTrials.gov Identifier: NCT02399917, Retrieved from: https://clinicaltrials.gov/ct2/show/study/NCT02399917, Mar. 26, 2015, pp. 1-8.

M.D. Anderson Cancer Center, "Lirilumab and Nivolumab With 5-Azacitidine in Patients With Myelodysplastic Syndromes (MOS)", ClinicalTrials.gov Identifier: NCT02599649, Retrieved from: https://clinicaltrials.gov/ct2/show/study/NCT02599649, Nov. 6, 2015, pp. 1-8.

M.D. Anderson Cancer Center, "Lirilumab With Rituximab for Relapsed, Refractory or High-risk Untreated Chronic Lymphocytic Leukemia (CLL) Patients", ClinicalTrials.gov Identifier: NCT02481297, Retrieved from: https://clinicaltrials.gov/ct2/show/study/NCT02481297, Jun. 25, 2015, pp. 1-7.

M.D. Anderson Cancer Center, "Nivolumab and HPV-16 Vaccination in Patients With HPV-16 Positive Incurable Solid Tumors", ClinicalTrials.gov Identifier: NCT02426892, Retrieved from: https://clinicaltrials.gov/ct2/show/NCT02426892, Apr. 27, 2015, pp. 1-8.

Ma et al., "The Chemokine Receptor CXCR4 is Required for the Retention of B Lineage and Granulocytic Precursors within the Bone Marrow Microenvironment", Immunity, Apr. 1999, 10:463-471.

Maciejewski-Duval et al., "Altered chemotactic response to CXCL12 in patients carrying GATA2 mutations", Journal of Leukocyte Biology, Jun. 2016, 99:1065-1076.

Maekawa et al., "Chemokine/Receptor Dynamics in the Regulation of Hematopoiesis", Internal Medicine, Feb. 2000, 39(2):90-100.

Matthys et al., "AMD3100, a Potent and Specific Antagonist of the Stromal Cell-Derived Factor-1 Chemokine Receptor CXCR4, Inhibits Autoimmune Joint Inflammation in IFN-gamma Receptor-Deficient Mice", The Journal of immunology, 2001, 167(8):4686-4692.

Maximilian Diehn, "SABR-ATAC: A Trial of TGF-beta Inhibition and Stereotactic Ablative Radiotherapy for Early Stage Non-small Cell Lung Cancer", ClinicalTrials.gov Identifier: NCT02581787, Retrieved from: https://clinicaltrials.gov/ct2/show/study/NCT02581787, Oct. 21, 2015, pp. 1-7.

McCormick et al., "Impaired Recruitment of Grk6 and beta-Arrestin 2 Causes Delayed Internalization and Desensitization of a WHIM Syndrome-Associated CXCR4 Mutant Receptor", PLoS One, Dec. 2009, 4(12)e8102:1-11.

McDermott et al., "A phase 1 clinical trial of long-term, low-dose treatment of WHIM syndrome with the CXCR4 antagonist plerixafor", Blood, Apr. 10, 2014, 123(15):2308-2316.

McDermott et al., "Safety and efficacy of the oral CXCR4 inhibitor X4P-001 + axitinib in advanced renal cell carcinoma patients: An analysis of subgroup responses by prior treatment", ESMO Conaress, Barcelona, Spain, Sep. 30, 2019, 1 page.

McDermott et al., "Severe congenital neutropenia resulting from G6PC3 deficiency with increased neutrophil CXCR4 expression and myelokathexis", Blood, Oct. 14, 2010, 116(15):2793-2802.

McDermott et al., "The CXCR4 antagonist plerixafor corrects panleukopenia in patients with WHIM syndrome", Blood, Nov. 3, 2011, 118(18):4957-4962.

McDermott, "WHIM Syndrome", National Organization for Rare Disorders, Retrieved from: https://rarediseases.org/rare-diseases/whim-syndrome, 2013, pp. 1-11.

MedImmune LLC, "A Phase 1 Study of MEDI0562 in Adult Subjects With Selected Advanced Solid Tumors", ClinicalTrials.gov Identifier: NCT02318394, Retrieved from: https://clinicaltrials.gov/ct2/show/study/NCT02318394, Dec. 17, 2014, pp. 1-10.

MedImmune LLC, "A Study in Adult Subjects With Select Advanced Solid Tumors", ClinicalTrials.gov Identifier: NCT02583165, Retrieved from: https://clinicaltrials.gov/ct2/show/study/NCT02583165, Oct. 22, 2015, pp. 1-7.

MedImmune LLC, "A Study to Evaluate MEDI0562 in Combination With Immune Therapeutic Agents in Adult Subjects With Advanced Solid Tumors", ClinicalTrials.gov Identifier: NCT02705482, Retrieved from: https://clinicaltrials.gov/ct2/show/study/NCT02705482, Mar. 10, 2016, pp. 1-10.

MedImmune LLC, "MEDI9447 Alone and in Combination With MEDI4736 in Adult Participants With Select Advanced Solid Tumors",

(56) References Cited

OTHER PUBLICATIONS

ClinicalTrials.gov Identifier: NCT02503774, Retrieved from: https://clinicaltrials.gov/ct2/show/study/NCT02503774, Jul. 21, 2015, 8 pages.
Merck KGaA, Darmstadt, Germany, "MSB0011359C (M7824) in Subjects With Metastatic or Locally Advanced Solid Tumors", ClinicalTrials.gov Identifier: NCT02699515, Retrieved from: https://clinicaltrials.gov/ct2/show/study/NCT02699515, Mar. 4, 2016, pp. 1-8.
Merck Sharp & Dohme Corp., "Study of MK-1454 Alone or in Combination With Pembrolizumab in Participants With Advanced/Metastatic Solid Tumors or Lymphomas (MK-1454-001)", ClinicalTrials.gov Identifier: NCT03010176, Retrieved from: https://clinicaltrials.gov/ct2/show/study/NCT03010176, Jan. 4, 2017, pp. 1-11.
Merck Sharp & Dohme Corp., "Study of MK-4166 and MK-4166 in Combination With Pembrolizumab (MK-3475) in Participants With Advanced Solid Tumors (MK-4166-001)", ClinicalTrials.gov Identifier: NCT02132754, Retrieved from: https://clinicaltrials.gov/ct2/show/study/NCT02132754, May 7, 2014, pp. 1-6.
Michael et al., "Exclusive and Persistent Use of the Entry Coreceptor CXCR4 by Human Immunodeficiency Virus Type 1 from a Subject Homozygous for CCR5 delta32", Journal of Virology, Jul. 1998, 72(7):6040-6047.
Miller et al., "Novel N-substituted benzimidazole CXCR4 antagonists as potential anti-HIV agents", Bioorganic and Medicinal Chemistry Letters, 2010, 20:2125-2128.
Miller et al., "Synthesis and SAR of novel isoquinoline CXCR4 antagonists with potent anti-HIV activity", Bioorganic and Medicinal Chemistry Letters, 2010, 20:3026-3030.
Moch et al., "miR-30c-2-3p and miR-30a-3p: New Pieces of the Jigsaw Puzzle in HIF2alpha Regulation", Cancer Discovery, Jan. 2014, 4(1):22-24.
Montane et al., "Prevention of murine autoimmune diabetes by CCL22-mediated Treg recruitment to the pancreatic islets", The Journal of Clinical Investigation, Aug. 2011, 121(8):3024-3028.
Morimoto et al., "Enhancement of the CXCL 12/CXCR4 axis due to acquisition of gemcitabine resistance in pancreatic cancer: effect of CXCR4 antagonists", BMC Cancer, May 12, 2016, 16(305):1-13.
Mosi et al., "The molecular pharmacology of AMD11070: an orally bioavailable CXCR4 HIV entry inhibitor", Biochemical Pharmacology, 2012, 83:472-479.
Moskovits et al., "p53 Attenuates Cancer Cell Migration and Invasion through Repression of SDF-1/CXCL 12 Expression in Stromal Fibroblasts", Cancer Research, Nov. 15, 2006, 66(22):10671-10676.
Motzer et al., "Nivolumab for Metastatic Renal Cell Carcinoma: Results of a Randomized Phase II Trial", Journal of Clinical Oncology, May 1, 2015,33(13):1430-1437.
Motzer et al., "Nivolumab versus Everolimus in Advanced Renal Cell Carcinoma", The New England Journal of Medicine, Nov. 5, 2015, 373(19):1803-1813.
Moyle et al., "Proof of Activity with AMD11070, an Orally Bioavailable Inhibitor of CXCR4-Tropic HIV Type 1", Clinical Infectious Diseases, Mar. 15, 2009, 48(6):798-805.
Murdoch et al., "Chemokine receptors and their role in inflammation and infectious diseases", Blood, May 15, 2000, 95(10):3032-3043.
Nagaraj et al., "Altered recognition of antigen is a novel mechanism of CD8+ T cell tolerance in cancer", Natural Medicine, Jul. 2007, 13(7):828-835.
Nagase et al., "Expression of CXCR4 in Eosinophils: Functional Analyses and Cytokine-Mediated Regulation", The Journal of Immunology, 2000, 164(11):5935-5943.
Nanki et al., "Cutting Edge: Stromal Cell-Derived Factor-1 Is a Costimulator for CD4+ T Cell Activation", The Journal of Immunology, 2000, 164:5010-5014.
Nash, "Allogeneic HSCT for autoimmune diseases: conventional conditioning regimens", Bone Marrow Transplantation, 2003, 32:S77-S80.
National Cancer Institute (NCI), "A Phase I Study of Intravenous Recombinant Human IL-15 in Adults With Refractory Metastatic Malignant Melanoma and Metastatic Renal Cell Cancer", ClinicalTrials.gov Identifier: NCT01021059, Retrieved from: https://clinicaltrials.gov/ct2/show/study/NCT01021059, Nov. 26, 2009, pp. 1-9.
National Cancer Institute (NCI), "Anti-ICOS Monoclonal Antibody MEDI-570 in Treating Patients With Relapsed or Refractory Peripheral T-cell Lymphoma Follicular Variant or Angioimmunoblastic T-cell Lymphoma", ClinicalTrials.gov Identifier: NCT02520791, Retrieved from: https://clinicaltrials.gov/ct2/show/study/NCT02520791, Aug. 13, 2015, pp. 1-13.
National Cancer Institute (NCI), "Nivolumab and Ipilimumab in Treating Patients With HIV Associated Relapsed or Refractory Classical Hodgkin Lymphoma or Solid Tumors That Are Metastatic or Cannot Be Removed by Surgery", ClinicalTrials.gov Identifier: NCT02408861, Retrieved from: https://clinicaltrials.gov/ct2/show/study/NCT02408861, Apr. 6, 2015, pp. 1-13.
National Cancer Institute (NCI), "Nivolumab in Treating Patients With HTLV-Associated T-Cell Leukemia/Lymphoma", ClinicalTrials.gov Identifier: NCT02631746, Retrieved from: https://clinicaltrials.gov/ct2/show/study/NCT02631746, Dec. 16, 2015, pp. 1-9.
National Cancer Institute (NCI), "Part 2 of Phase 1 Study of GC1008 to Treat Advanced Melanoma (Part 2 Will Only Accept and Treat Patients With Advanced Malignant Melanoma)", ClinicalTrials.gov Identifier: NCT00923169, Retrieved from: https://clinicaltrials.gov/ct2/show/study/NCT00923169, Jun. 18, 2009, pp. 1-8.
National Cancer Institute (NCI), "Subcutaneous Recombinant Human IL-15 (s.c. rhIL-15) and Alemtuzumab for People With Refractory or Relapsed Chronic and Acute Adult T-cell Leukemia (ATL)", ClinicalTrials.gov Identifier: NCT02689453, Retrieved from: https://clinicaltrials.gov/ct2/show/study/NCT02689453, Feb. 24, 2016, pp. 1-9.
National Cancer Institute (NCI), "Trametinib and Navitoclax in Treating Patients With Advanced or Metastatic Solid Tumors", ClinicalTrials.gov Identifier: NCT02079740, Retrieved from: https://clinicaltrials.gov/ct2/show/study/NCT02079740, Mar. 6, 2014, pp. 1-12.
National Cancer Institute (NCI), "Use of IL-15 After Chemotherapy and Lymphocyte Transfer in Metastatic Melanoma", ClinicalTrials.gov Identifier: NCT01369888, Retrieved from: https://clinicaltrials.gov/ct2/show/study/NCT01369888, Jun. 9, 2011, pp. 1-9.
Neumedicines Inc., "NM-IL-12 (rHuIL-12) In Relapsed/Refractory Diffuse Large B-Cell Lymphoma (DLBCL) Undergoing Salvage Chemotherapy", ClinicalTrials.gov Identifier: NCT02544724, Retrieved from: https://clinicaltrials.gov/study/NCT02544724, Sep. 9, 2015, pp. 1-8.
Neumedicines Inc., "NM-IL-12 in Cutaneous T-Cell Lymphoma (CTCL) Undergoing Total Skin Electron Beam Therapy (TSEBT)", ClinicalTrials.gov Identifier: NCT02542124, Retrieved from: https://clinicaltrials.gov/ct2/show/study/NCT02542124, Sep. 4, 2015, pp. 1-8.
Neves et al., "Ligand-guided optimization of CXCR4 homology models for virtual screening using a multiple chemotype approach", Journal of Computer-Aided Molecular Design, 2010, 24(12):1023-1033.
Nicholas Butowski, "A Study of Varlilumab and IMA950 Vaccine Plus Poly-ICLC in Patients With WHO Grade II Low-Grade Glioma (LGG)", ClinicalTrials.gov Identifier: NCT02924038, Retrieved from: https://clinicaltrials.gov/ct2/show/study/NCT02924038, Oct. 5, 2016, pp. 1-9.
Novartis Pharmaceuticals, "A Phase I/Ib Study of NIZ985 in Combination With PDR001 in Adults With Metastatic Cancers", ClinicalTrials.gov Identifier: NCT02452268, Retrieved from: https://clinicaltrials.gov/ct2/show/study/NCT02452268, May 22, 2015, pp. 1-7.
Novartis Pharmaceuticals, "Phase I/Ib Study of GWN323 Alone and in Combination With PDR001 in Patients With Advanced Malignancies and Lymphomas", ClinicalTrials.gov Identifier: NCT02740270, Retrieved from: https://clinicaltrials.gov/ct2/show/study/NCT02740270, Apr. 15, 2016, pp. 1-6.
Novartis Pharmaceuticals, "Phase I/Ib Study of NIS793 in Combination With PDR001 in Patients With Advanced Malignancies",

(56) References Cited

OTHER PUBLICATIONS

ClinicalTrials.gov Identifier: NCT02947165, Retrieved from: https://clinicaltrials.gov/ct2/show/study/NCT02947165, Oct. 27, 2016, pp. 1-9.
Novartis Pharmaceuticals, "Phase I/II Study of BLZ945 Single Agent or BLZ945 in Combination With PDR001 in Advanced Solid Tumors", ClinicalTrials.gov Identifier: NCT02829723, Retrieved from: https://clinicaltrials.gov/ct2/show/study/NCT02829723, Jul. 12, 2016, pp. 1-7.
Novartis Pharmaceuticals, "Safety and Efficacy of MBG453 as Single Agent and in Combination With PDR001 in Patients With Advanced Malignancies", ClinicalTrials.gov Identifier: NCT02608268, Retrieved from: https://clinicaltrials.gov/ct2/show/study/NCT02608268, Nov. 18, 2015, pp. 1-10.
Novartis Pharmaceuticals, "Study of the Safety and Efficacy of MIW815 With PDR001 in Patients With Advanced/Metastatic Solid Tumors or Lymphomas", ClinicalTrials.gov Identifier: NCT03172936, Retrieved from: https://clinicaltrials.gov/study/NCT03172936?term=NCT03172936&rank=1, Jun. 1, 2017, pp. 1-9.
Nyunt et al., "Pharmacokinetic effect of AMD070, an Oral CXCR4 antagonist, on CYP3A4 and CYP2D6 substrates midazolam and dextromethorphan in healthy volunteers", Journal of Acquired Immune Deficiency Syndromes, Apr. 15, 2008,47(5):559-565.
O'Boyle et al., "Inhibition of CXCR4-CXCL 12 chemotaxis in melanoma by AMD11070", British Journal of Cancer, 2013, 108:1634-1640.
Ohagen et al., "Apoptosis Induced by Infection of Primary Brain Cultures with Diverse Human Immunodeficiency Virus Type 1 Isolates: Evidence for a Role of the Envelope", Journal of Virology, Feb. 1999, 73(2):897-906.
Okazaki et al., "A rheostat for immune responses: the unique properties of PD-1 and their advantages for clinical application", Nature immunology, 2013, 14(12):1212-1218.
Oncolytics Biotech, "A Study of REOLYSIN® in Combination With Gemcitabine in Patients With Advanced Pancreatic Adenocarcinoma", ClinicalTrials.gov Identifier: NCT00998322, Retrieved from https://clinicaltrials.gov/ct2/show/study/NCT00998322, Oct. 20, 2009, pp. 1-6.
Oncolytics Biotech, "Efficacy Study of REOLYSIN® in Combination With Paclitaxel and Carboplatin in Platinum-Refractory Head and Neck Cancers", ClinicalTrials.gov Identifier: NCT01166542, https://clinicaltrials.gov/ct2/show/study/NCT01166542, Jul. 21, 2010, pp. 1-7.
Oncolytics Biotech, "Phase 2 Study of REOLYSIN® in Combination With Paclitaxel and Carboplatin for Non-Small Cell Lung Cancer With KRAS or EGFR Activation", ClinicalTrials.gov Identifier: NCT00861627, Retrieved from: https://clinicaltrials.gov/ct2/show/study/NCT00861627, Mar. 13, 2009, pp. 1-7.
OncoMed Pharmaceuticals, Inc., "A Study of OMP-313M32 in Subjects With Locally Advanced or Metastatic Solid Tumors", ClinicalTrials.gov Identifier: NCT03119428, Retrieved from https://clinicaltrials.gov/ct2/show/study/NCT03119428, Apr. 18, 2017, pp. 1-7.
Panka et al., "Abstract# 320: MDSC trafficking and function in RCC by CXCR4 in the presence of a VEGF-R antagonist is dependent on HIF-2(alpha) expression", European Journal of Cancer, 2016, 69(1):S105.
Panka et al., "Effects of HDM2 antagonism on sunitinib resistance, p53 activation, C244|SDF-1 induction, and tumor infiltration by CD11b+/Gr-1+ myeloid derived suppressor cells", Molecular Cancer, Mar. 5, 2013, 12(17):1-12.
Parameswaran et al., "Combination of drug therapy in acute lymphoblastic leukemia with a CXCR4 antagonist", Leukemia, Aug. 2011, 25(8):1314-1323.
Peled et al., "The chemokine SDF-1 activates the integrins LFA-1, VLA-4, and VLA-5 on immature human CD34(+) cells: role in transendothelial/stromal migration and engraftment of NOD/SCID mice", Blood, Jun. 1, 2000, 95(11):3289-3296.
Pfizer, "A Study Of Avelumab In Combination With Other Cancer Immunotherapies In Advanced Malignancies (JAVELIN Medley)", ClinicalTrials.gov Identifier: NCT02554812, Retrieved from: https://clinicaltrials.gov/ct2/show/study/NCT02554812, Sep. 18, 2015, pp. 1-13.
Pfizer, "Avelumab In Combination Regimens That Include An Immune Agonist, Epigenetic Modulator, CD20 Antagonist and/or Conventional Chemotherapy in Patients With Relapsed or Refractory Diffuse Large B-cell Lymphoma (R/R DLBCL) (Javelin DLBCL)", ClinicalTrials.gov Identifier: NCT02951156, Retrieved from: https://clinicaltrials.gov/ct2/show/study/NCT02951156, Nov. 1, 2016, pp. 1-11.
Pike et al., "Nutrition: An Integrated Approach", Third Edition, John Wiley and Sons, 1984:538-539.
Plexxikon, "A Combination Clinical Study of PLX3397 and Pembrolizumab To Treat Advanced Melanoma and Other Solid Tumors", ClinicalTrials.gov Identifier: NCT02452424, Retrieved from: https://clinicaltrials.gov/ct2/show/study/NCT02452424, May 22, 2015, pp. 1-9.
Ponath, "Chemokine receptor antagonists: novel therapeutics for inflammation and AIDS", Expert Opinion on Investigational Drugs, 1998, 7(1):1-18.
Portella et al., "Preclinical Development of a Novel Class of CXCR4 Antagonist Impairing Solid Tumors Growth and Metastases", PLoS One, Sep. 2013, 8(9)e74548:1-9.
Providence Health & Services, "Anti-OX40 Antibody (MEDI6469) in Patients With Metastatic Colorectal Cancer", ClinicalTrials.gov Identifier: NCT02559024, Retrieved from: https://clinicaltrials.gov/ct2/show/study/NCT02559024, Sep. 24, 2015, pp. 1-6.
Providence Health & Services, "Anti-OX40 Antibody in Head and Neck Cancer Patients", ClinicalTrials.gov Identifier: NCT02274155, Retrieved from: https://clinicaltrials.gov/ct2/show/study/NCT02274155, Oct. 24, 2014, pp. 1-6.
Providence Health & Services, "Anti-OX40, Cyclophosphamide (CTX) and Radiation in Patients With Progressive Metastatic Prostate Cancer", ClinicalTrials.gov Identifier: NCT01303705, Retrieved from: https://clinicaltrials.gov/ct2/show/study/NCT01303705, Feb. 25, 2011, pp. 1-10.
Providence Health & Services, "Stereotactic Body Radiation and Monoclonal Antibody to OX40 (MEDI6469) in Breast Cancer Patients With Metastatic Lesions (OX40 Breast)", ClinicalTrials.gov Identifier: NCT01862900, Retrieved from: https://clinicaltrials.gov/ct2/show/study/NCT01862900, May 27, 2017, pp. 1-7.
PsiOxus Therapeutics Ltd, "Phase I / Dose Expansion Study of Enadenotucirev in Ovarian Cancer Patients (OCTAVE)", ClinicalTrials.gov Identifier: NCT02028117, Retrieved from: https://clinicaltrials.gov/ct2/show/study/NCT02028117, Jan. 6, 2014, pp. 1-8.
PsiOxus Therapeutics Ltd, "Phase I Study of Enadenotucirev and PD-1 Inhibitor in Subjects With Metastatic or Advanced Epithelial Tumors (SPICE)", ClinicalTrials.gov Identifier: NCT02636036, Retrieved from: https://clinicaltrials.gov/ct2/show/study/NCT02636036, Dec. 21, 2015, pp. 1-9.
PubChem Open Chemistry Database, Compound Summary for CID No. 10890081, Oct. 26, 2006, 14 pages.
PubChem Open Chemistry Database, Compound Summary for CID No. 12087079, Feb. 7, 2007, 14 pages.
PubChem Open Chemistry Database, Compound Summary for CID No. 19046926, created Dec. 4, 2007, 11 pages.
PubChem Open Chemistry Database, Compound Summary for CID No. 70962830, created Mar. 21, 2013, 12 pages.
PubChem Substance Record for SID No. 219642471, Oct. 21, 2014, 3 pages.
Raman et al., "Immunotherapy in Metastatic Renal Cell Carcinoma: A Comprehensive Review", BioMed Research International, 2015, 2015(367354):1-8.
Rana et al., "Role of CCR5 in infection of primary macrophages and lymphocytes by macrophage-tropic strains of human immunodeficiency virus: resistance to patient-derived and prototype isolates resulting from the delta ccr5 mutation", Journal of Virology, Apr. 1997, 71(4):3219-3227.
Ratajczak et al., "The pleiotropic effects of the SDF-1-CXCR4 axis in organogenesis, regeneration and tumorigenesis", Leukemia, 2006, 20:1915-1924.
Reagan-Shaw et al., "Dose translation from animal to human studies revisited", The FASEB Journal, Mar. 2007, 22:659-661.

(56) References Cited

OTHER PUBLICATIONS

Reetz et al., “Highly Efficient Lipase-Catalyzed Kinetic Resolution of Chiral Amines”, Chimia, 1994, 48:570.
Regeneron Pharmaceuticals, “An Exploratory Tumor Biopsy-driven Study to Understand the Relationship Between Biomarkers and Clinical Response in Melanoma Patients Receiving REGN2810 (Anti-PD-1)”, ClinicalTrials.gov Identifier: NCT03002376, Retrieved from: https://clinicaltrials.gov/ct2/show/study/NCT03002376, Dec. 23, 2016, pp. 1-6.
Regeneron Pharmaceuticals, “PD-1 in Patients With Advanced Basal Cell Carcinoma Who Experienced Progression of Disease on Hedgehog Pathway Inhibitor Therapy, or Were Intolerant of Prior Hedgehog Pathway Inhibitor Therapy”, ClinicalTrials.gov Identifier: NCT03132636, Retrieved from: https://clinicaltrials.gov/ct2/show/study/NCT03132636, Apr. 28, 2017, pp. 1-6.
Regeneron Pharmaceuticals, “Study of REGN 2810 Compared to Platinum-Based Chemotherapies in Participants With Metastatic Non-Small Cell Lung Cancer (NSCLC)”, ClinicalTrials.gov Identifier: NCT03088540, Retrieved from: https://clinicaltrials.gov/ct2/show/study/NCT03088540, Mar. 23, 2017, pp. 1-9.
Regeneron Pharmaceuticals, “Study of REGN2810 and REGN1979 in Patients With Lymphoma”, ClinicalTrials.gov Identifier: NCT02651662, Retrieved from: https://clinicaltrials.gov/ct2/show/study/NCT02651662, Jan. 11, 2016, pp. 1-7.
Regeneron Pharmaceuticals, “Study of REGN2810 in Patients With Advanced Cutaneous Squamous Cell Carcinoma”, ClinicalTrials.gov Identifier: NCT02760498, Retrieved from: https://clinicaltrials.gov/ct2/show/study/NCT02760498, May 3, 2016, pp. 1-6.
Regeneron Pharmaceuticals, “Study of REGN3767 (Anti-LAG-3) With or Without REGN2810 (Anti-PD1) in Advanced Cancers”, ClinicalTrials.gov Identifier: NCT03005782, Retrieved from: https://clinicaltrials.gov/ct2/show/study/NCT03005782, Dec. 29, 2016, pp. 1-7.
Righi et al., “CXCL12/CXCR4 blockade induces multimodal antitumor effects that prolong survival in an immunocompetent mouse model of ovarian cancer”, Cancer Research, Aug. 15, 2011, 71(16):5522-5534.
Rini et al., “Comparative effectiveness of axitinib versus sorafenib in advanced renal cell carcinoma (AXIS): a randomised phase 3 trial”, Lancet, Dec. 3, 2011, 378:1931-1939.
Robert et al., “Pembrolizumab versus Ipilimumab in Advanced Melanoma”, The New England Journal of Medicine, Jun. 25, 2015, 372(26):2521-2532.
Robert Lowsky, “A Phase 1/11 Study of Intratumorally Injection of SD-101”, ClinicalTrials.gov Identifier: NCT02254772, Retrieved from: https://clinicaltrials.gov/ct2/show/study/NCT02254772, Oct. 2, 2014, pp. 1-9.
Salcedo et al., “Vascular Endothelial Growth Factor and Basic Fibroblast Growth Factor Induce Expression of CXCR4 on Human Endothelial Cells: In Vivo Neovascularization Induced by Stromal-derived Factor-1 alpha”, The American Journal of Pathology, Apr. 1999, 154(4):1125-1135.
Saxena et al., “Efficacy and Mechanism of Action of CXCR4 Inhibition in B16 OVA Melanoma Model”, The Society for Immunotherapy of Cancer Annual Meeting, National Harbour, Maryland, Nov. 8-12, 2017, 1 page.
Saxena et al., “Efficacy and Mechanism of Action of CXCR4 Inhibition in B16-OVA |Melanoma Model”, Journal for Immuno Therapy of Cancer, 2017, Abstract 5(Suppl 2):P356.
Scala et al., “Expression of CXCR4 Predicts Poor Prognosis in Patients with Malignant Melanoma”, Clinical Cancer Research, Mar. 1, 2005, 11:1835-1841.
Scala, “Molecular Pathways: Targeting the CXCR4-CXCL 12 Axis-Untapped Potential in the Tumor Microenvironment”, Clinical Cancer Research, Oct. 1, 2015, 21(19):4278-4285.
Schlabach et al., “Cancer Proliferation Gene Discovery Through Functional Genomics”, Science, Feb. 1, 2008, 319(5863):620-624.
Schols et al., “Bicyclams, a class of potent anti-HIV agents, are targeted at the HIV coreceptor fusin/CXCR-4”, Antiviral Research, 1997, 35:147-156.
Schols et al., “Inhibition of T-tropic HIV strains by selective antagonization of the chemokine receptor CXCR4”, The Journal of Experimental Medicine, Oct. 20, 1997, 186(8):1383-1388.
Schramm et al., “Cytopathicity of human immunodeficiency virus type 2 (HIV-2) in human lymphoid tissue is coreceptor dependent and comparable to that of HIV-1”, Journal of Virology, Oct. 2000, 74(20):9594-9600.
Schuitemaker et al., “Biological phenotype of human immunodeficiency virus type 1 clones at different stages of infection: progression of disease is associated with a shift from monocytotropic to T-cell-tropic virus population”, Journal of Virology, Mar. 1992, 66(3):1354-1360.
Shad et al., “Synthesis and Anti-HIV Activity of a Novel Series of Isoquinoline-Based CXCR4 Antagonists”, Molecules, 2021, 26(6927): 1-19.
Sharma et al., “Primary, Adaptive, and Acquired Resistance to Cancer Immunotherapy”, Cell, Feb. 9, 2017, 168(4):707-723.
Shen et al., “CXCR4-mediated Stat3 activation is essential for CXCL 12-induced cell invasion in bladder cancer”, Tumour Biology, 2013, 34:1839-1845.
Shojaei et al., “Tumor refractoriness to anti-VEGF treatment is mediated by CD11b+Gr1+ myeloid cells”, Nature Biotechnology, Aug. 2007, 25(8):911-920.
Sidney Kimmel Comprehensive Cancer Center at Johns Hopkins, “Anti-LAG-3 Alone & in Combination w/ Nivolumab Treating Patients w/ Recurrent GBM (Anti-CD137 Arm Closed Oct. 16, 18)”, ClinicalTrials.gov Identifier: NCT02658981, Retrieved from: https://clinicaltrials.gov/ct2/show/study/NCT02658981, Jan. 20, 2016, pp. 1-13.
Sidney Kimmel Comprehensive Cancer Center at Johns Hopkins, “Pilot Study With CY, Pembrolizumab, GVAX, and IMC-CS4 (LY3022855) in Patients With Borderline Resectable Adenocarcinoma of the Pancreas”, ClinicalTrials.gov Identifier: NCT03153410, Retrieved from: https://clinicaltrials.gov/ct2/show/study/NCT03153410, May 15, 2017, pp. 1-8.
SillaJen Inc., “Hepatocellular Carcinoma Study Comparing Vaccinia Virus Based Immunotherapy Plus Sorafenib vs Sorafenib Alone (PHOCUS)”, ClinicalTrials.gov Identifier: NCT02562755, Retrieved from: https://clinicaltrials.gov/ct2/show/study/NCT02562755, Sep. 29, 2015, pp. 1-7.
Silva et al., “Profiling Essential Genes in Human Mammary Cells by Multiplex RNAi Screening”, Science, Feb. 1, 2008, 319(5863):617-620.
Simmons et al., “CXCR4 as a Functional Coreceptor for Human Immunodeficiency Virus Type 1 Infection of Primary Macrophages”, Journal of Virology, Oct. 1998, 72(10):8453-8457.
Simmons et al., “Primary, syncytium-inducing human immunodeficiency virus type 1 isolates are dual-tropic and most can use either lestr or CCR5 as coreceptors for virus entry”, Journal of Virology, Dec. 1996, 70(12:8355-8360.
SK Chemicals Co. Ltd., “Study to Evaluate SID 530 Compared to Taxotere”, ClinicalTrials. gov Identifier: NCT00931008, Retrieved from https://clinicaltrials.gov/ct2/show/study/NCT00931008, Jul. 2, 2009, pp. 1-6.
Skerlj et al., “Discovery of Novel Small Molecule Orally Bioavailable C-X-C Chemokine Receptor 4 Antagonists That Are Potent Inhibitors of T-tropic (X4) HIV-1 Replication”, Journal of Medicinal Chemistry, 2010, 53(8):3376-3388.
Stone et al., “Multiple-Dose Escalation Study of the Safety, Pharmacokinetics, and Biologic Activity of Oral AMD070, a Selective CXCR4 Receptor Inhibitor, in Human Subjects”, Antimicrobial Agents and Chemotherapy, Jul. 2007, 51(7):2351-2358.
Sullivan et al., “Pembrolizumab for Treatment of Patients with Advanced or Unresectable Melanoma”, Clinical Cancer Research, Jul. 1, 2015, 21(13):2892-2897.
Syndax Pharmaceuticals, “A Phase 2 Multi-Center Study of Entinostat (SNDX-275) in Patient With Relapsed or Refractory Hodgkin's Lymphoma (ENGAGE-501)”, ClinicalTrials.gov Identifier: NCT00866333, Retrieved from: https://clinicaltrials.gov/ct2/show/study/NCT00866333, Mar. 20, 2009, pp. 1-6.
Targovax Oy, “A Pilot Study of Sequential ONCOS-102, an Engineered Oncolytic Adenovirus Expressing GMCSF, and Pembrolizumab in Patients With Advanced or Unresectable Melanoma Progressing

(56) References Cited

OTHER PUBLICATIONS

After Programmed Cell Death Protein 1 (PD1) Blockade", ClinicalTrials.gov Identifier: NCT03003676, Retrieved from https://clinicaltrials.gov/ct2/show/study/NCT03003676, Dec. 28, 2016, pp. 1-8.
Tarhini et al., "Immune Monitoring of the Circulation and the Tumor Microenvironment in Patients with Regionally Advanced Melanoma Receiving Neoadjuvant Ipilimumab", PLoS One, Feb. 2014, 9(2)e87705:1-9.
Teasdale et al., "Risk Assessment of Genotoxic Impurities in New Chemical Entities: Strategies To Demonstrate Control", Organic Process Research and Development, 2013, 17:221-230.
Tersmette et al., "Differential Syncytium-Inducing Capacity of Human Immunodeficiency Virus Isolates: Frequent Detection of Syncytium-inducing Isolates in Patients with Acquired Immunodeficiency Syndrome (AIDS) and AIDS-Related Complex", Journal of Virology, Jun. 1988, 62(6):2026-2032.
Tesaro, Inc., "A Phase 1 Study of TSR-022, an Anti-TIM-3 Monoclonal Antibody, in Patients With Advanced Solid Tumors (AMBER)", ClinicalTrials.gov Identifier: NCT02817633, Retrieved from https://clinicaltrials.gov/ct2/show/study/NCT02817633, Jun. 29, 2016, pp. 1-8.
Therapeutics, Encyclopedia Britannica Online, Retrieved from: https://www.britannica.com/science/therapeutics, Nov. 6, 2018, 1 page.
Therasse et al., "New Guidelines to Evaluate the Response to Treatment in Solid Tumors", Special Article, Journal of the National Cancer Institute, Feb. 2, 2000, 92(3):205-216.
Tortorici et al., "Influence of mild and moderate hepatic impairment on axitinib pharmacokinetics", Investigational New Drugs, 2011, 29:1370-1380.
Toyozawa et al., "Chemokine Receptor CXCR4 Is a Novel Marker for the Progression Cutaneous Malignant Melanomas", Acta Histochemica Et Cytochemica, 2012, 45(5):293-299.
Trillium Therapeutics Inc., "A Trial of TTI-621 for Patients With Hematologic Malignancies and Selected Solid Tumors", ClinicalTrials.gov Identifier: NCT02663518, Retrieved from: https://clinicaltrials.gov/ct2/show/study/NCT02663518, Jan. 26, 2016, 9 pages.
Trillium Therapeutics Inc., "Trial of Intratumoral Injections of TTI-621 in Subjects With Relapsed and Refractory Solid Tumors and Mycosis Fungoides", ClinicalTrials.gov Identifier: NCT02890368, Retrieved from https://clinicaltrials.gov/ct2/show/study/NCT02890368, Sep. 7, 2016, pp. 1-9.
Tu et al., "Curcumin induces the differentiation of myeloid-derived suppressor cells and inhibits their interaction with cancer cells and related tumor growth", Cancer prevention research (Philadelphia, Pa.), Feb. 2012, 5(2):205-215.
Tumeh et al., "PD-1 blockade induces responses by inhibiting adaptive immune resistance", Nature, Nov. 27, 2014, 515(7528):568-571.
U.S. Appl. No. 18/828,839, Brands et al., filed Sep. 9, 2024.
U.S. Appl. No. 18/850,818, Taveras et al., filed Sep. 25, 2024.
U.S. Appl. No. 18/873,655, Nguyen et al., filed Dec. 10, 2024.
U.S. Appl. No. 19/096,210, Nguyen et al., filed Dec. 10, 2024.
U.S. Appl. No. 19/096,210, of Kelley et al., filed Mar. 31, 2025.
University of Southern California, "Axitinib With or Without Anti-OX40 Antibody PF-04518600 in Treating Patients With Metastatic Kidney Cancer", ClinicalTrials.gov Identifier: NCT03092856, Retrieved from: https://clinicaltrials.gov/ct2/show/study/NCT03092856, Mar. 28, 2017, pp. 1-11.
University of Texas Southwestern Medical Center, "Phase 2 Study of IDH305 in Low Grade Gliomas", ClinicalTrials.gov Identifier: NCT02987010, Retrieved from: https://clinicaltrials.gov/ct2/show/study/NCT02987010, Dec. 8, 2016, pp. 1-7.
Vaishampay an et al., "A phase 1/2 study evaluating the efficacy and safety of the oral CXCR4 inhibitor X4P-001 in combination with axitinib in patients with advanced renal cell carcinoma", Journal of Clinical Oncology, 2018;36(15 suppl):1 page.
Vanharanta et al., "Epigenetic expansion of VHL-HIF signal output drives multiorgan metastasis in renal cancer", Nature Medicine, Jan. 2013, 19(1):50-56.
VentiRx Pharmaceuticals Inc., "A Phase Ib Study of Neoadjuvant of Cetuximab Plus Motolimod and Cetuximab Plus Motolimod Plus Nivolumab", ClinicalTrials.gov Identifier: NCT02124850, Retrieved from https://clinicaltrials.gov/ct2/show/study/NCT02124850, Apr. 28, 2014, pp. 1-6.
Ward et al., "Genetic and molecular diagnosis of severe congenital neutropenia", Current Opinion in Hematology, Jan. 2009, 16(1):9-13.
Wong et al., "Comparison of the potential multiple binding modes of bicyclam, monocylam, and noncyclam small-molecule CXC chemokine receptor 4 inhibitors", Molecular Pharmacology, 2008, 74(6):1485-1495.
World Medical Association, "WMA Declaration of Helsinki—Ethical Principles for Medical Research Involving Human Subjects", 2013, Retrieved from: http://www.wma.net/en/30publications/10policies/b3/, 4 pages.
X4 Pharmaceuticals, "Addition of X4P-001 to Nivolumab Treatment in Participants With Renal Cell Carcinoma", ClinicalTrails.gov Identifier: NCT02923531, https://clinicaltrials.gov/study/NCT02923531?tab=history, First submitted Feb. 8, 2017, Latest version submitted Jul. 24, 2019, 5 pages.
X4 Pharmaceuticals, "Trial of X4P-001 in Patients With Advanced Renal Cell Carcinoma", ClinicalTrials.gov Identifier: NCT02667886, Retrieved from https://clinicaltrials.gov/study/NCT02667886?term=NCT02667886&rank=1, Jan. 29, 2016, pp. 1-10.
X4 Pharmaceuticals, "X4 Pharmaceuticals announces new data for lead candidate X4P-001 in renal cell carcinoma at EORTC-NCI-AACR Molecular Targets and Cancer Therapeutics Symposium", Retrieved from https://investors.x4pharma.com/news-releases/news-release-details/x4-pharmaceuticals-announces-new-data-lead-candidate-x4p-001, Nov. 30, 2016, 2 pages.
X4 Pharmaceuticals, "X4P-001 and Pembrolizumab in Patents With Advanced Melanoma (X4P-001-MELA)", ClinicalTrails.gov Identifier: NCT02823405, Retrieved from https://clinicaltrials.gov/ct2/show/NCT02823405, Jul. 6, 2016, pp. 1-7.
ZagZag et al., "Stromal Cell-Derived Factor-1 alpha and CXCR4 Expression in Hemangioblastoma and Clear Cell-Renal Cell Carcinoma: von Hippel-Lindau Loss-of-Function Induces Expression of a Ligand and Its Receptor", Cancer Research, Jul. 15, 2005, 65(14):6178-6188.
Zea et al., "Arginase-Producing Myeloid Suppressor Cells in Renal Cell Carcinoma Patients: A Mechanism of Tumor Evasion", Cancer Research, Apr. 15, 2005, 65(8):3044-3048.
Zhang et al., "Chemokine Coreceptor Usage by Diverse Primary Isolates of Human Immunodeficiency Virus Type 1", Journal of Virology, Nov. 1998, 72(11):9307-9312.
Zhang et al., "Preferential Involvement of CX Chemokine Receptor 4 and CX Chemokine Ligand 12 in T-Cell Migration Toward Melanoma Cells", Cancer Biology & Therapy, Oct. 2006, 5(10):1034-1312.
Zhang et al., "Will Multiple Coreceptors Need To Be Targeted by Inhibitors of Human C338|Immunodeficiency Virus Type 1 Entry?", Journal of Virology, Apr. 1999, 73(4):3443-3448.
Zhao et al., "TNF signaling drives myeloid-derived suppressor cell accumulation", The Journal of Clinical Investigation, Nov. 2012, 122(11):4094-4104.
Zlotnik et al., "Chemokines: A New Classification System and Their Role in Immunity", Immunity, Feb. 2000, 12:121-127.
Zou et al., "PD-L1 (B7-H1) and PD-1 pathway blockade for cancer therapy: Mechanisms, response biomarkers, and combinations", Science Translational Medicine, Mar. 2, 2016, 8(328):328rv4, pp. 1-34.
Zuelzer, "Myelokathexis - A New Form of Chronic Granulocytopenia - Report of a Case", The New England Journal of Medicine, Apr. 2, 1964, 270(14):699-704.
Kissane et al. (2013) "Counterion effects in the preparation of aldehyde-bisulfite adducts", Tetrahedron Letters, 54:6587-6591.
Pandit et al. (2009) "Expedient Reductive Amination of Aldehyde Bisulfite Adducts", Synthesis, 23:4032-4036.
Ashcroft, et al., "Asymmetric Synthesis of an MMP-3 Inhibitor Incorporating a 2-Alkyl Succinate Motif," Organic Process Research & Development, 7(3):362-368 (2003).

SYNTHESIS OF MAVORIXAFOR AND INTERMEDIATES THEREOF

CROSS-REFERENCE TO RELATED APPLICATIONS

This application is a National Phase Application of International Patent Application No. PCT/US2022/046094 filed on Oct. 7, 2022, which claims the benefit of U.S. Provisional Patent Application No. 63/262,225, filed Oct. 7, 2021, the entirety of each of which is hereby incorporated by reference.

FIELD OF THE INVENTION

The present invention relates to methods for synthesizing mavorixafor, and to intermediates thereto.

BACKGROUND OF THE INVENTION

C-X-C chemokine receptor type 4 (CXCR4), also known as fusin or cluster of differentiation 184 (CD 184), is a seven transmembrane G-protein coupled receptor (GPCR) belonging to Class I GPCR or rhodopsin-like GPCR family. Under normal physiological conditions, CXCR4 carries out multiple roles and is principally expressed in the hematopoietic and immune systems. CXCR4 was initially discovered as one of the co-receptors involved in human immunodeficiency virus (HIV) cell entry. Subsequent studies showed that it is expressed in many tissues, including brain, thymus, lymphatic tissues, spleen, stomach, and small intestine, and also specific cell types such as hematopoietic stem cells (HSC), mature lymphocytes, and fibroblasts. CXCL12, previously designated SDF-1a, is the only known ligand for CXCR4. CXCR4 mediates migration of stem cells during embryonic development as well as in response to injury and inflammation. Multiple roles have been demonstrated for CXCR4 in human diseases such as cellular proliferative disorders, Alzheimer's disease, HIV, rheumatoid arthritis, pulmonary fibrosis, and others. For example, expression of CXCR4 and CXCL12 have been noted in several tumor types. CXCL12 is expressed by cancer-associated fibroblast (CAFs) and is often present at high levels in the tumor microenvironment (TME). In clinical studies of a wide range of tumor types, including breast, ovarian, renal, lung, and melanoma, expression of CXCR4/CXCL12 has been associated with a poor prognosis and with an increased risk of metastasis to lymph nodes, lung, liver, and brain, which are sites of CXCL12 expression. CXCR4 is frequently expressed on melanoma cells, particularly the CD133+ population that is considered to represent melanoma stem cells; in vitro experiments and murine models have demonstrated that CXCL12 is chemotactic for such cells.

Furthermore, there is now evidence implicating the CXCL12/CXCR4 axis in contributing to the loss or lack of tumor responsiveness to angiogenesis inhibitors (also referred to as "angiogenic escape"). In animal cancer models, interference with CXCR4 function has been demonstrated to alter the TME and sensitize the tumor to immune attack by multiple mechanisms such as elimination of tumor re-vascularization and increasing the ratio of CD8+ T cells to Treg cells. These effects result in significantly decreased tumor burden and increased overall survival in xenograft, syngeneic, and transgenic cancer models. See Vanharanta et al. (2013) Nat Med 19: 50-56; Gale and McColl (1999) BioEssays 21: 17-28; Highfill et al. (2014) Sci Transl Med 6: ra67; Facciabene et al. (2011) Nature 475: 226-230.

These data underscore the significant unmet need for CXCR4 inhibitors to treat the many diseases and conditions mediated by aberrant or undesired expression of the receptor, for example in cellular proliferative disorders.

DETAILED DESCRIPTION OF THE INVENTION

Mavorixafor, and pharmaceutically acceptable compositions thereof, are effective as CXC receptor type 4 (CXCR4) inhibitors, and are useful for treating a variety of diseases, disorders, or conditions associated with CXCR4, such as hyperproliferative conditions including various cancers. The methods and intermediates of the present invention are useful for preparing mavorixafor, which is described in, e.g., U.S. patent application Ser. No. 16/215,963 (U.S. Pat. No. 10,548,889), in the name of Brands, the entirety of which is incorporated herein by reference. The present invention relates to certain novel intermediates to the synthesis of mavorixafor that are easier to isolate, purify, and/or handle, and/or are more stable in comparison to corresponding intermediates in the existing methods. Furthermore, such intermediates enable methods of synthesis of mavorixafor that feature improved efficiency, reproducibility, purity, scalability, and manufacturability. In certain embodiments, the present compounds are generally prepared by assembly of three fragments F-1, F-2, and F-3, according to Scheme I set forth below:

Scheme I

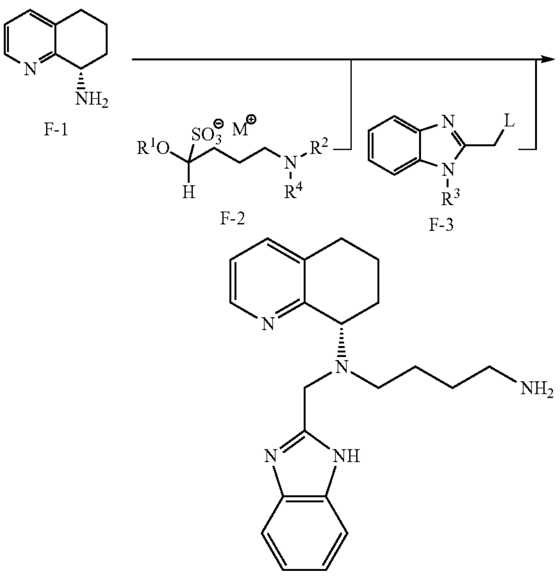

F-1 F-2 F-3

Mavorixafor

In Scheme I above, $R^1$ is H, a suitable hydroxyl protecting group, or, taken with the oxygen atom to which it is bound, a leaving group; $R^2$ and $R^4$ independently are H, or a suitable amino protecting group; $R^3$ is H, or a suitable benzimidazole protecting group; L is a suitable leaving group; and M is a metal selected from alkali metals.

1. Fragment F-1

Fragment F-1 may be prepared using methods known in the art, for example as described in U.S. patent application Ser. No. 16/215,963 (U.S. Pat. No. 10,548,889); U.S. Pat. No. 7,354,934; and Crawford et al., *Organic Process*

*Research & Development,* 2008, 12, 823-830; the entire contents of each of which are incorporated herein by reference.

2. Fragment F-2

According to one embodiment, the present invention provides a compound F-2:

F-2

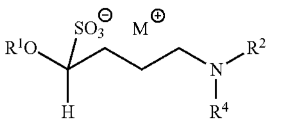

wherein:

$R^1$ is H, a suitable hydroxyl protecting group, or, taken with the oxygen atom to which it is bound, a leaving group;

$R^2$ and $R^4$ independently are H, or a suitable amino protecting group; and

M is a metal selected from alkali metals.

Leaving groups are well known in the art and include those described in detail in *Leaving group*, Gold Book, IUPAC. 2009, ISBN 978-0-9678550-9-7, the entirety of which is incorporated herein by reference.

Suitable hydroxyl and amino protecting groups are well known in the art and include those described in detail in *Protecting Groups in Organic Synthesis*, T. W. Greene and P. G. M. Wuts, $3^{rd}$ edition, John Wiley & Sons, 1999, the entirety of which is incorporated herein by reference.

In certain embodiments, $R^1$, taken with the oxygen atom to which it is bound, is selected from esters, ethers, silyl ethers, alkyl ethers, arylalkyl ethers, and alkoxyalkyl ethers. Examples of such esters include formates, acetates, carbonates, and sulfonates. Specific examples include formate, benzoyl formate, chloroacetate, trifluoroacetate, methoxyacetate, triphenylmethoxyacetate, p-chlorophenoxyacetate, 3-phenylpropionate, 4-oxopentanoate, 4,4-(ethylenedithio) pentanoate, pivaloate (trimethylacetyl), crotonate, 4-methoxy-crotonate, benzoate, p-benzylbenzoate, 2,4,6-trimethylbenzoate, tosylate, mesylate, triflate, or carbonates such as methyl, 9-fluorenylmethyl, ethyl, 2,2,2-trichloro ethyl, 2-(trimethylsilyl)ethyl, 2-(phenylsulfonyl)ethyl, vinyl, allyl, and p-nitrobenzyl. Examples of such silyl ethers include trimethylsilyl, triethylsilyl, t-butyldimethylsilyl, t-butyldiphenylsilyl, triisopropylsilyl, and other trialkylsilyl ethers. Alkyl ethers include methyl, benzyl, p-methoxybenzyl, 3,4-dimethoxybenzyl, trityl, t-butyl, allyl, and allyloxycarbonyl ethers or derivatives. Alkoxyalkyl ethers include acetals such as methoxymethyl, methylthiomethyl, (2-methoxyethoxy)methyl, benzyloxymethyl, beta-(trimethylsilyl)ethoxymethyl, and tetrahydropyranyl ethers. Examples of arylalkyl ethers include benzyl, p-methoxybenzyl (MPM), 3,4-dimethoxybenzyl, O-nitrobenzyl, p-nitrobenzyl, p-halobenzyl, 2,6-dichlorobenzyl, p-cyanobenzyl, 2- and 4-picolyl.

According to one embodiment, $R^1$ is H.

In certain embodiments, $R^2$, taken with the nitrogen atom to which it is bound, is selected from, but is not limited to, aralkylamines, carbamates, allyl amines, amides, and the like, e.g., t-butyloxycarbonyl (Boc), ethyloxycarbonyl, methyloxycarbonyl, trichloroethyloxycarbonyl, allyloxycarbonyl (Alloc), benzyloxycarbonyl (CBZ), allyl, benzyl (Bn), fluorenylmethylcarbonyl (Fmoc), acetyl, chloroacetyl, dichloroacetyl, trichloroacetyl, phenylacetyl, trifluoroacetyl, benzoyl, pivaloyl and the like.

According to one embodiment, $R^2$ is Boc.

In certain embodiments, $R^4$, taken with the nitrogen atom to which it is bound, is selected from, but is not limited to, aralkylamines, carbamates, allyl amines, amides, and the like, e.g., t-butyloxycarbonyl (Boc), ethyloxycarbonyl, methyloxycarbonyl, trichloroethyloxycarbonyl, allyloxycarbonyl (Alloc), benzyloxycarbonyl (CBZ), allyl, benzyl (Bn), fluorenylmethylcarbonyl (Fmoc), acetyl, chloroacetyl, dichloroacetyl, trichloroacetyl, phenylacetyl, trifluoroacetyl, benzoyl, pivaloyl and the like.

According to one embodiment, $R^4$ is Boc.

According to another embodiment, both $R^2$ and $R^4$ are Boc.

According to one embodiment, M is Na.

According to one embodiment, M is K.

In certain embodiments, the present invention provides a compound of the formula F-2a:

F-2a

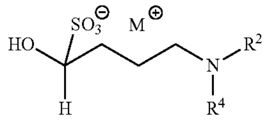

wherein $R^2$, $R^4$ and M are as defined herein, both singly and in combination.

In certain embodiments, the present invention provides a compound of the formula F-2b:

F-2b

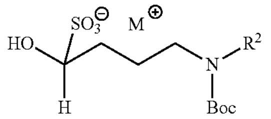

wherein $R^2$ and M are as defined herein, both singly and in combination

In certain embodiments, the present invention provides a compound of the formula F-2c:

F-2c

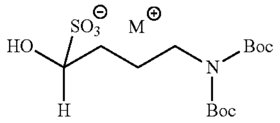

wherein M is as defined herein.

In certain embodiments, the present invention provides a compound of the formula F-2d:

F-2d

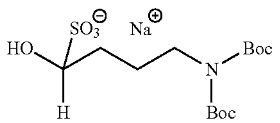

Compound F-2d can be efficiently synthesized with bisulfite salts and the corresponding aldehyde, compound B-1 as depicted in Example 1 below.

Compounds of formula F-2, such as F-2d, are stable solids that are easy to isolate, purify, and store. The corresponding aldehyde, compound B-1, is difficult to purify and store. Using compounds of formula F-2 also gives better yields in the subsequent synthetic steps compared to using B-1. In certain embodiments, the compounds of formula F-2 are prepared according to Scheme II set forth below:

by DMAP. In yet another embodiment, the protection is performed without a catalyst. In certain embodiments, the protection is performed at 20 to 60° C. In one embodiment, the protection is performed at 35 to 45° C. In one embodiment, protection is performed at 40° C. In certain embodiments, the protection is performed by stirring the reaction mixture for 0 to 2 hours. In one embodiment, protection is Scheme II

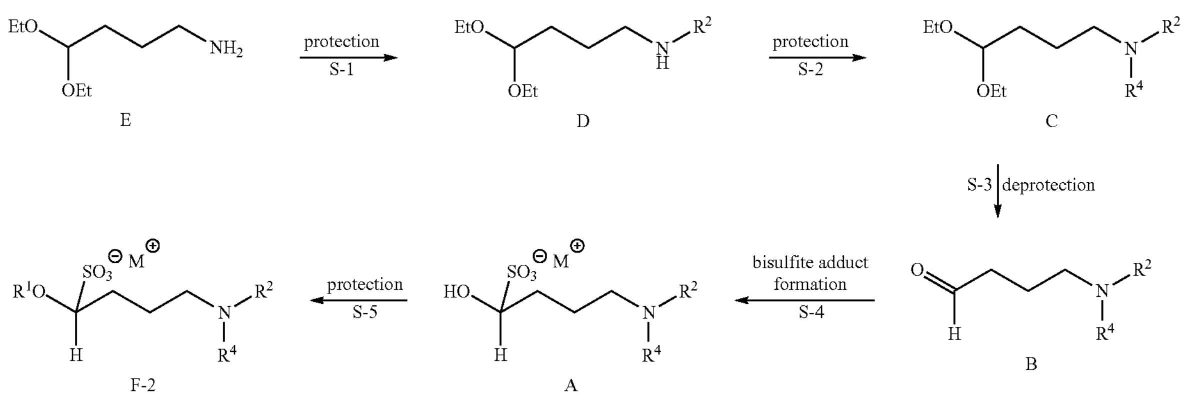

In Scheme II above, $R^1$, $R^2$, $R^4$ and M are as defined above for compound F-2.

In one aspect, the present invention provides methods for preparing compounds of formulae D, C, B, A, and F-2 according to the steps depicted in Scheme II, above. In the compounds of the present formulae, $R^1$, $R^2$, $R^4$ and M are as defined above for compound F-2.

At step S-1, the amino group of compound E is protected with a suitable protecting group. Suitable protecting groups for amino groups are well known to one of ordinary skill in the art and are as defined above for compound F-2. In certain embodiments, the protecting group is Boc, Cbz, ethyloxycarbonyl, methyloxycarbonyl, trichloroethyloxycarbonyl, allyloxycarbonyl (Alloc), allyl, benzyl (Bn), fluorenylmethylcarbonyl (Fmoc), acetyl, chloroacetyl, dichloroacetyl, trichloroacetyl, phenylacetyl, trifluoroacetyl, benzoyl, or pivaloyl. In one embodiment, the protecting group is Boc. Methods for protecting amino groups are well known to one of ordinary skill in the art and typically include a reaction between a compound bearing an amino group and a suitable reagent of formula $PG^1LG^1$, wherein $PG^1$ is a protecting group and $LG^1$ is a suitable leaving group. Exemplary reactions include those described in detail in *Protecting Groups in Organic Synthesis*, T. W. Greene and P. G. M. Wuts, 3$^{rd}$ edition, John Wiley & Sons, 1999, the entirety of which is incorporated herein by reference. In certain embodiments, compound E is protected by reacting it with a reagent selected from Boc-Cl, Cbz-Cl and $(Boc)_2O$. In one embodiment, compound E is protected by reacting it with $(Boc)_2O$. In certain embodiments, the protection is performed in a solvent selected from $CH_2Cl_2$, THF, DMF and MeCN. In one embodiment, the protection is performed in MeCN. In certain embodiments, the protection is performed by using 1 to 1.5 molar equivalents of $(Boc)_2O$. In one embodiment, the protection is performed by using 1 to 1.2 molar equivalents of $(Boc)_2O$. In one embodiment, the protection is performed by using 1.2 molar equivalents of $(Boc)_2O$. In certain embodiments, the protection is performed in the presence of a catalyst selected from DMAP and pyridine. In one embodiment, the protection is catalyzed performed by stirring the reaction mixture for 0 to 1 hour. In another embodiment, protection is performed by stirring the reaction mixture for 0 to 30 minutes. In another embodiment, protection is performed by stirring the reaction mixture for 0 minutes. According to one embodiment, the reaction is performed as described in U.S. patent application Ser. No. 16/215,963 (U.S. Pat. No. 10,548,889). In one embodiment, the reaction is performed as described in the Step 1A in Example 1 below. In yet another embodiment, the compound D is a non-isolated intermediate.

At step S-2, the —NH— group of compound D is protected with a suitable protecting group. Suitable protecting groups for —NH— groups are well known to one of ordinary skill in the art and are as defined above for compound F-2. In certain embodiments, the protecting group is Boc, Cbz, ethyloxycarbonyl, methyloxycarbonyl, trichloroethyloxycarbonyl, allyloxycarbonyl (Alloc), allyl, benzyl (Bn), fluorenylmethylcarbonyl (Fmoc), acetyl, chloroacetyl, dichloroacetyl, trichloroacetyl, phenylacetyl, trifluoroacetyl, benzoyl, or pivaloyl. In one embodiment, the protecting group is Boc. Methods for protecting amino groups are well known to one of ordinary skill in the art and typically include a reaction between a compound bearing an amino group and a suitable reagent of formula $PG^1LG^1$, wherein $PG^1$ is a protecting group and $LG^1$ is a suitable leaving group. Exemplary reactions include those described in detail in *Protecting Groups in Organic Synthesis*, T. W. Greene and P. G. M. Wuts, 3$^{rd}$ edition, John Wiley & Sons, 1999, the entirety of which is incorporated herein by reference. In certain embodiments, compound D is protected by reacting it with a reagent selected from Boc-Cl, Cbz-Cl and $(Boc)_2O$. In one embodiment, compound D is protected by reacting it with $(Boc)_2O$. In certain embodiments, the protection is performed in a solvent selected from $CH_2Cl_2$, THF, DMF and MeCN. In one embodiment, the protection is performed in MeCN. In certain embodiments, the protection is performed by using 1 to 1.5 molar equivalents of $(Boc)_2O$. In one embodiment, the protection is performed by using 1 to 1.2 molar equivalents of $(Boc)_2O$. In one embodiment, the protection is performed by using 1.2 molar equivalents of $(Boc)_2O$. In certain embodiments, the protection is performed in the presence of a catalyst selected from DMAP and pyridine. In one embodiment, the protection is catalyzed by DMAP. In yet another embodiment, the protection is performed without a catalyst. In certain embodiments, the protection is performed at 20 to 60° C. In one embodiment, the protection is performed at 35 to 45° C. In one embodiment, protection is performed at 40° C. In certain embodiments, the protection is performed by stirring the reaction mixture for 0 to 2 hours. In one embodiment, protection is performed by stirring the reaction mixture for 0 to 1 hour. In another embodiment, protection is performed by stirring the reaction mixture for 0 to 30 minutes. In another embodiment, protection is performed by stirring the reaction mixture for 0 minutes. According to one embodiment, the reaction is performed as described in U.S. patent application Ser. No. 16/215,963 (U.S. Pat. No. 10,548,889). In one embodiment, the reaction is performed as described in the Step 1B in Example 1 below. In another embodiment, the compound C is a non-isolated intermediate. In yet another embodiment, both steps S-1 and S-2 are performed in a single reaction vessel.

At step S-3, the acetal group of compound C is deprotected. Methods for deprotecting acetal groups are well known to one of ordinary skill in the art and typically include a reaction between a compound bearing an acetal group and a suitable acid. Exemplary reactions include those described in detail in *Protecting Groups in Organic Synthesis*, T. W. Greene and P. G. M. Wuts, 3$^{rd}$ edition, John Wiley & Sons, 1999, the entirety of which is incorporated herein by reference. In certain embodiments, compound C is deprotected by reacting it with an acid selected from glacial acetic acid, pTSA, HCl and $H_2SO_4$. In one embodiment compound C is deprotected by reacting it with glacial acetic acid. In one embodiment, the deprotection is performed wherein glacial acetic acid is used as solvent. In certain embodiments, the deprotection is performed in presence of NaCl. In certain embodiments, the deprotection id performed at 20 to 60° C. In one embodiment, the deprotection is performed at 25 to 45° C. In one embodiment, deprotection is performed at 30° C. In certain embodiments, the deprotection is performed by stirring the reaction mixture for 0 to 5 hours. In one embodiment, deprotection is performed by stirring the reaction mixture for 1 to 4 hours. In another embodiment, deprotection is performed by stirring the reaction mixture for 2 to 3 hours. In another embodiment, deprotection is performed by stirring the reaction mixture for 3 hours. In certain embodiments, the product after deprotection is treated with decolorizing activated charcoal in heptane at 25 to 55° C. for 1 to 3 hours. In an embodiment, the product after deprotection is treated with decolorizing activated charcoal in heptane at 35 to 45° C. for 1 to 2 hours. In an embodiment, the product after deprotection is treated with decolorizing activated charcoal in heptane at 40° C. for 1 hour. According to one embodiment, the reaction is performed as described in U.S. patent application Ser. No. 16/215,963 (U.S. Pat. No. 10,548,889). In one embodiment, the reaction is performed as described in the Step 1C in Example 1 below. In yet another embodiment, the compound B is a non-isolated intermediate.

At step S-4, the aldehyde group of compound B is converted to a bisulfite adduct. Aldehyde-bisulfite adducts are well known to one of the ordinary skill in the art and include those described in detail in Kissane et al, *Tetrahedron Letters,* 54 (2013), 6587-6591, the entirety of which is incorporated herein by reference. In certain embodiments, M is Na or K. In other embodiments, M is Na. Methods for converting aldehyde groups to bisulfite adducts are well known to one of ordinary skill in the art and typically include a reaction between a compound bearing an aldehyde group and metabisulfite salt of an alkali metal. Exemplary reactions include those described in detail in Kissane et al, *Tetrahedron Letters,* 54 (2013), 6587-6591, the entirety of which is incorporated herein by reference. In certain embodiments, compound B is converted to a bisulfite adduct by reacting it with a compound of formula $M_2S_2O_5$, wherein M is an alkali metal. In one embodiment, compound B is converted to a bisulfite adduct by reacting it with a compound of formula $M_2S_2O_5$, wherein M is selected from Na and K. In another embodiment, compound B is converted to a bisulfite adduct by reacting it with a compound of formula $M_2S_2O_5$, wherein M is Na. In another embodiment, compound B is converted to a bisulfite adduct by reacting it with a compound of formula $M_2S_2O_5$, wherein M is K. In one embodiment, the reaction is performed by reacting compound B in heptane with $M_2S_2O_5$ in purified water. In certain embodiments, the reaction is performed at 20 to 60° C. In one embodiment, the reaction is performed at 35 to 45° C. In one embodiment, reaction is performed at 40° C. In certain embodiments, the reaction is performed, wherein 0.5 to 0.8 molar equivalents of $M_2S_2O_5$ are added in 4 to 8 equal portions. In an embodiment, the reaction is performed, wherein 0.625 molar equivalents of $M_2S_2O_5$ are added in 5 equal portions. In certain embodiments, the reaction is performed by stirring the reaction mixture for 25 to 60 hours. In one embodiment, reaction is performed by stirring the reaction mixture for 30 to 45 hours. In another embodiment, deprotection is performed by stirring the reaction mixture for 36 hours. In certain embodiments, the product A is precipitated by cooling the reaction mixture to 5 to 35° C. over 2 to 6 hours. In an embodiment, the product A is precipitated by cooling the reaction mixture to 15 to 25° C. over 3 to 4 hours. In an embodiment, the product A is precipitated by cooling the reaction mixture to 20° C. over about 3 hours. In certain embodiments, the precipitated product A is purified by washing it with pre-mixed 1:1 mixture of THE and n-heptane at 5 to 35° C. In one embodiment, the precipitated product A is purified by washing it with pre-mixed 1:1 mixture of THE and n-heptane at 15 to 25° C. In one embodiment, the precipitated product A is purified by washing it with pre-mixed 1:1 mixture of THE and n-heptane at 20° C. In certain embodiments, the precipitated product A is purified by washing it with n-heptane at 5 to 35° C., for example, one, two, three, four or five times. In one embodiment, the precipitated product A is purified by washing it with n-heptane at 15 to 25° C., for example, one, two, or three times. In one embodiment, the precipitated product A is purified by washing it with n-heptane at 20° C., for example, one, two, or three times. In certain embodiments, the precipitated product A is purified by washing it with MeCN. In certain embodiments, the solid product A is dried under a flow of nitrogen, for example, warm nitrogen. In some embodiments, product A is dried under nitrogen at 20 to 60° C. for an appropriate period of time, such as about 5 to 25 hours. In one embodiment, product A is dried under nitrogen at 35 to 40° C. for an appropriate period of time, such as about 10 to 14 hours. In one embodiment, the solid product A is dried under a flow of nitrogen at 38° C., for example, for about 12 hours. In one embodiment, the reaction is performed as described in the Step 1D in Example 1 below.

Product A may be used as obtained from step S-4, or the hydroxyl group is optionally protected. At step S-5, the hydroxyl group of compound A is protected with a suitable hydroxyl protecting group. Suitable protecting groups for hydroxyl groups are well known to one of ordinary skill in the art and are as defined above for compound F-2. Methods for protecting hydroxyl-groups are well known to one of ordinary skill in the art and typically include a reaction between a compound bearing a hydroxyl group and a suitable reagent of formula $PG^3LG^3$, wherein $PG^3$ is a protecting group and $LG^3$ is a suitable leaving group. Exemplary reactions include those described in detail in *Protecting Groups in Organic Synthesis*, T. W. Greene and P. G. M. Wuts, 3rd edition, John Wiley & Sons, 1999, the entirety of which is incorporated herein by reference.

3. Fragment F-3

According to one embodiment, the compounds of formula F-3 are prepared according to Scheme III set forth below:

Scheme III

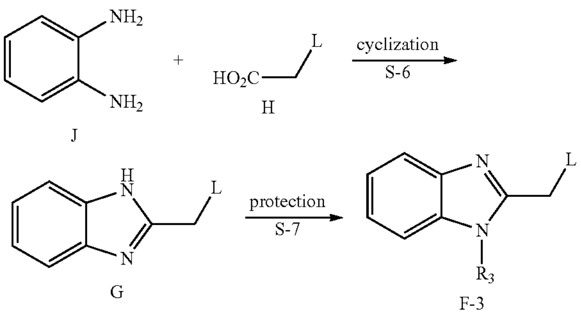

J H G F-3

In one aspect, the present invention provides methods for preparing compounds of formulae G and F-3 according to the steps depicted in Scheme III, above. In the compounds of the formulae H, G and F-3, $R^3$ is a suitable benzimidazole protecting group; and L is a suitable leaving group.

Suitable benzimidazole protecting groups are well known in the art and include those described in detail in *Protecting Groups in Organic Synthesis*, T. W. Greene and P. G. M. Wuts, 3rd edition, John Wiley & Sons, 1999, the entirety of which is incorporated herein by reference. In certain embodiments, $R^3$, taken with the nitrogen atom to which it is bound, is selected from, but are not limited to, aralkylamines, carbamates, allyl amines, amides, and the like, e.g., t-butyloxycarbonyl (Boc), ethyloxycarbonyl, methyloxycarbonyl, trichloroethyloxycarbonyl, allyloxycarbonyl (Alloc), benzyloxycarbonyl (CBZ), allyl, benzyl (Bn), fluorenylmethylcarbonyl (Fmoc), acetyl, chloroacetyl, dichloroacetyl, trichloroacetyl, phenylacetyl, trifluoroacetyl, benzoyl, pivaloyl and the like. According to one embodiment, $R^3$ is Boc.

As defined above, L is a suitable leaving group. Suitable leaving groups are well known in the art, e.g., see, *Advanced Organic Chemistry*, J. March, 5th Edition, John Wiley and Sons, 2000. Such leaving groups include, but are not limited to, halogen, alkoxy, sulphonyloxy, optionally substituted alkylsulphonyloxy, optionally substituted alkenylsulfonyloxy, optionally substituted arylsulfonyloxy, and diazonium moieties.

Additional examples of suitable leaving groups include chloro, iodo, bromo, fluoro, methanesulfonyloxy (mesyloxy), p-toluenesulfonyloxy (tosyloxy), trifluoromethanesulfonyloxy (triflyloxy), nitro-phenylsulfonyloxy (nosyloxy), and bromo-phenylsulfonyloxy (brosyloxy). In certain embodiments, L is halogen. In other embodiments, L is an optionally substituted alkylsulphonyloxy, optionally substituted alkenylsulfonyloxy, or optionally substituted arylsulfonyloxy. According to one embodiment, L is a halogen. According to yet another embodiment, L is chloro.

According to one embodiment, compound F-3 in Scheme III is of the formula F-3a:

F-3a

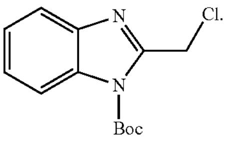

At step S-6, a cyclization reaction is carried out between compound J and a compound of formula H. Acid-catalyzed cyclization reactions between o-arylenediamines and carboxylic acids, or derivatives thereof, are well known to one of ordinary skill in the art, e.g., see, E. C. Wagner and W. H. Millett, *Benzimidazole, Organic Syntheses*, (1943), Collective Volume 2, page 65. In certain embodiments, cyclization reaction between compound J and a compound of formula H is catalyzed by an acid selected from formic acid, HCl, HBr, $H_2SO_4$ and $H_3PO_4$. According to one embodiment, the cyclization reaction is catalyzed by HCl. In certain embodiments, the cyclization reaction is performed in a solvent selected from water, DMF and MeCN. In one embodiment, the solvent is water. In certain embodiments, the cyclization reaction is performed by using 1 to 3 molar equivalents of chloroacetic acid. In one embodiment, the cyclization reaction is performed by using 1 to 1.7 molar equivalents of chloroacetic acid. In one embodiment, the cyclization reaction is performed by using about 1.5 molar equivalents of chloroacetic acid. In certain embodiments, the cyclization reaction is performed at about 40 to 120° C. In one embodiment, the cyclization reaction is performed at about 70 to 90° C. In one embodiment, cyclization reaction is performed at about 80° C. In certain embodiments, the cyclization reaction is performed by allowing compound J and compound H to contact each other for about 5 to 35 hours. In one embodiment, cyclization reaction is performed by allowing compound J and compound H to contact each other for about 15 to 25 hours. In another embodiment, the cyclization reaction is performed by allowing compound J and compound H to contact each other for about 20 hours. In certain embodiments, the product G is precipitated by cooling the reaction mixture to about 0 to 25° C. over about 0 to 4 hours and adding potassium phosphate solution to adjust the pH of the reaction mixture to 5 to 9. In one embodiment, the product G is precipitated by cooling the reaction mixture to about 5 to 15° C. over about 1 to 2 hours and adding potassium phosphate solution to adjust the pH of the reaction mixture to 6.8 to 7.2. In an embodiment, the product G is precipitated by cooling the reaction mixture to 10° C. for about 1 hour and adding potassium phosphate solution to adjust the pH of the reaction mixture to about 7. In certain embodiments, the precipitated product G is purified by washing it with water. The washing is optionally performed at a reduced temperature, for example, at 0 to 25° C. The washing is optionally repeated, for example, 1 to 7 times. In certain embodiments, the precipitated product G is purified by washing it with water at about 5 to 15° C. a total of 2 to 5 times. In one embodiment, the precipitated product G is purified by washing it with water at about 10° C. a total of 3 times. In certain embodiments, the precipitated product G is purified by washing it with MeCN at 0 to 30° C., 2 to 10 times. In one embodiment, the precipitated product G is purified by washing it with MeCN at 5 to 15° C., 5 to 8 times. In one embodiment, the precipitated product G is purified by washing it with MeCN at about 10° C., for a total of 6 times. In certain embodiments, the solid product G is dried under a flow of nitrogen, which is optionally performed at a reduced temperature, for example, at 5 to 35° C. In one embodiment, the solid product G is dried under a flow of nitrogen at 15 to 25° C. In some embodiments, the product G is dried until its water content is ≤25% w/w by Karl-Fisher analysis. In one embodiment, the product G is dried until its water content is ≤15% w/w by Karl-Fisher analysis. In one embodiment, the solid product G is dried under a flow of nitrogen at about 20° C., for example, until its water content is ≤15% w/w by Karl-Fisher analysis. In certain embodiments, the solid product G is dried under a flow of nitrogen at about 10 to 50° C., for example, until its water content is ≤5% w/w by Karl-Fisher analysis. In one embodiment, the solid product G is dried under a flow of nitrogen at about 25 to 35° C., for example, until its water content is ≤5% w/w by Karl-Fisher analysis. In one embodiment, the solid product G is dried under a flow of nitrogen at about 30° C., until its water content is ≤5% w/w by Karl-Fisher analysis. In certain embodiments, the solid product G is dried under a flow of nitrogen at about 30 to 70° C., until its water content is ≤1% w/w by Karl-Fisher analysis. In one embodiment, the solid product G is dried under a flow of nitrogen at about 45 to 55° C., until its water content is ≤1% w/w by Karl-Fisher analysis. In one embodiment, the solid product G is dried under a flow of nitrogen at about 50° C., until water content is ≤1% w/w by Karl-Fisher analysis. In one embodiment, the reaction is performed as described in the Step 2A in Example 2 below.

At step S-7, the —NH— group of compound G is protected with a suitable benzimidazole protecting group. Suitable benzimidazole protecting groups are well known to one of ordinary skill in the art and are as defined above for compound F-3. Methods for protecting the —NH— group of benzimidazoles are well known to one of ordinary skill in the art and typically include a reaction between a compound bearing a benzimidazole moiety with an —NH— group and a suitable reagent of formula $PG^4LG^4$, wherein $PG^4$ is a protecting group and $LG^4$ is a suitable leaving group. Exemplary reactions include those described in detail in *Protecting Groups in Organic Synthesis*, T. W. Greene and P. G. M. Wuts, 3$^{rd}$ edition, John Wiley & Sons, 1999, the entirety of which is incorporated herein by reference. In certain embodiments, compound G is protected by reacting it with a reagent selected from Boc-Cl, Cbz-Cl and $(Boc)_2O$. In one embodiment, compound G is protected by reacting it with $(Boc)_2O$. In certain embodiments, the protection is performed in a solvent selected from $CH_2Cl_2$, THF, DMF, and MeCN. In one embodiment, the protection is performed in DMF. In certain embodiments, the protection is performed by using 1 to 2 molar equivalents of $(Boc)_2O$. In one embodiment, the protection is performed by using 1 to 1.6 molar equivalents of $(Boc)_2O$. In one embodiment, the protection is performed by using 1.4 molar equivalents of $(Boc)_2O$. In certain embodiments, the protection is performed in the presence of a catalyst selected from DMAP and pyridine. In one embodiment, the protection is catalyzed by DMAP. In yet another embodiment, the protection is performed without a catalyst. In certain embodiments, the protection is performed in the presence of a base selected from DIPEA and TEA. In one embodiment, the protection is performed in the presence of DIPEA. In certain embodiments, the protection is performed at about 20 to 60° C. In one embodiment, the protection is performed at about 35 to 45° C. In one embodiment, protection is performed at about 40° C. In certain embodiments, the protection is performed by stirring the reaction mixture for about 5 to 30 hours or until complete. In one embodiment, protection is performed by stirring the reaction mixture for about 10 to 20 hours. In another embodiment, protection is performed by stirring the reaction mixture for about 16 hours. In certain embodiments, after protection the reaction mixture is treated with decolorizing activated charcoal at about 20 to 60° C. for at least 40 minutes. In one embodiment, after protection the reaction mixture is treated with decolorizing activated charcoal at about 35 to 45° C. for at least 60 minutes. In an embodiment, after protection the reaction mixture is treated with decolorizing activated charcoal at about 40° C. for about 60 to 90 minutes. In some embodiments, the product F-3 is purified by direct crystallization from the reaction mixture by addition of water at about 20 to 60° C. followed by cooling the reaction mixture to effect crystallization. In one embodiment, the product F-3 is purified by direct crystallization from the reaction mixture by addition of water at about 35 to 45° C. followed by cooling the reaction mixture to effect crystallization. In some embodiments, the reaction mixture is cooled to about 34 to 36° C. over about 30 to 120 minutes. In certain embodiments, the product F-3 is purified by direct crystallization from the reaction mixture by addition of water at about 25 to 60° C. followed by cooling the reaction mixture to about 10 to 45° C. over about 40 to 80 minutes. In one embodiment, the product F-3 is purified by direct crystallization from the reaction mixture by addition of water at about 40° C. followed by cooling the reaction mixture to about 35° C. over about 60 minutes. In some embodiments, crystallization of product F-3 is facilitated by addition of F-3 as seed material. In some embodiments, the seed material is added at about 25 to 45° C., followed by cooling the reaction mixture to about 20 to 45° C. over about 5 to 75 minutes. In some embodiments, the seed material is added at about 34 to 36° C., followed by cooling the reaction mixture to about 28 to 32° C. over about 20 to 60 minutes. In one embodiment, crystallization of product F-3 is facilitated by addition of F-3 as seed material at about 35° C., followed by cooling the reaction mixture to about 30° C. over about 40 minutes. In some embodiments, addition of F-3 as seed material is repeated, followed by stirring the reaction mixture at about 20 to 40° C. for about 0 to 3 hours. In some embodiments, addition of F-3 as seed material is repeated, followed by stirring the reaction mixture at about 28 to 32° C. for about 1 to 2 hours. In one embodiment, addition of F-3 as seed material is repeated, followed by stirring the reaction mixture at about 30° C. for about 1.5 hours. In some embodiments, crystallization is initiated by further cooling the reaction mixture to about 5 to 35° C. over about 1 to 6 hours. In some embodiments, crystallization is initiated by further cooling the reaction mixture to about 15 to 25° C. over about 3 to 4 hours. In one embodiment, crystallization is initiated by further cooling the reaction mixture to about 20° C. over about 3 hours. In some embodiments, crystallization is initiated by further addition of water at about 5 to 35° C., followed by stirring the reaction mixture for at least 1 hours. In some embodiments, crystallization is initiated by further addition of water at about 15 to 25° C., followed by stirring the reaction mixture for at least 3 hours. In one embodiment, crystallization is initiated by further addition of water at about 20° C. followed by stirring the reaction mixture for about 3 hours. In some embodiments, crystallization is initiated by cooling the reaction mixture to about −5 to 15° C. over a period of about 1 to 4 hours, followed by stirring at −5 to 15° C. for at least 1 hours. In some embodiments, crystallization is initiated by cooling the reaction mixture to about 0 to 5° C. over a period of about 2.5 hours, followed by stirring at 0 to 5° C. for at least 2.5 hours. In one embodiment, crystallization is initiated by cooling the reaction mixture to about 2° C. over about 2.5 hours, followed by stirring at about 2° C. for about 2.5 hours. In certain embodiments, the crystallized product F-3 is purified by washing it with pre-mixed DMF and water as an about 1:1 to 1:3 mixture, optionally at a reduced temperature of about −5 to 15° C. In some embodiments, the crystallized product F-3 is purified by washing it with pre-mixed DMF and water as an about 1:2 mixture, optionally at a reduced temperature of about 0 to 5° C. In one embodiment, the crystallized product F-3 is purified by washing it with pre-mixed DMF and water as an about 1:2 mixture, optionally at a reduced temperature of about 2° C. In certain embodiments, the crystallized product F-3 is purified by washing it with purified water at about 0 to 10° C. In some embodiments, the crystallized product F-3 is purified by washing it with purified water at about 0 to 5° C. In one embodiment, the crystallized product F-3 is purified by washing it with purified water at about 2° C. In certain embodiments, the crystallized product F-3 is dried under vacuum at ≤50° C., for example, until water content is ≤0.2% w/w by Karl-Fisher analysis and DMF content is ≤0.4% w/w. In some embodiments, the crystallized product F-3 is dried under vacuum at ≤30° C., for example, until water content is ≤0.2% w/w by Karl-Fisher analysis and DMF content is ≤0.4% w/w. In one embodiment, the crystallized product F-3 is dried under vacuum at 28° C., until water content is ≤0.2% w/w by Karl-Fisher analysis and DMF content is ≤0.4% w/w. According to one embodiment, the reaction is performed as described in U.S. patent application Ser. No. 16/215,963 (U.S. Pat. No. 10,548,889). In one embodiment, the reaction is performed as described in the Step 2B in Example 2 below.

4. Assembly of F-1, F-2, and F-3 to Prepare Mavorixafor

Preparation of mavorixafor by assembly of fragments F-1, F-2a and F-3 is accomplished as set forth in Scheme IV below.

Scheme IV

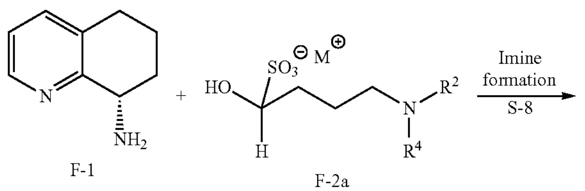

F-1

F-2a

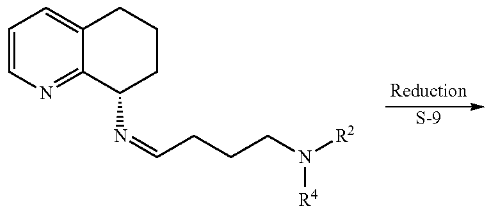

Q

-continued

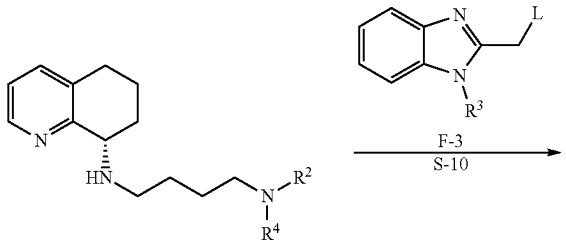

P

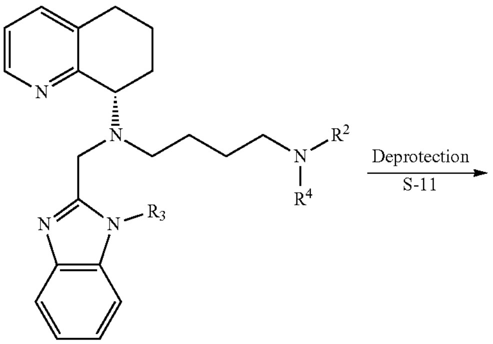

O

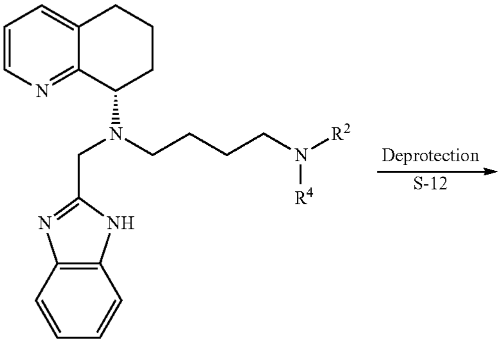

N

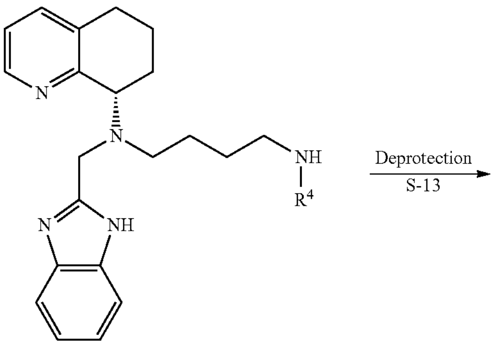

M

-continued

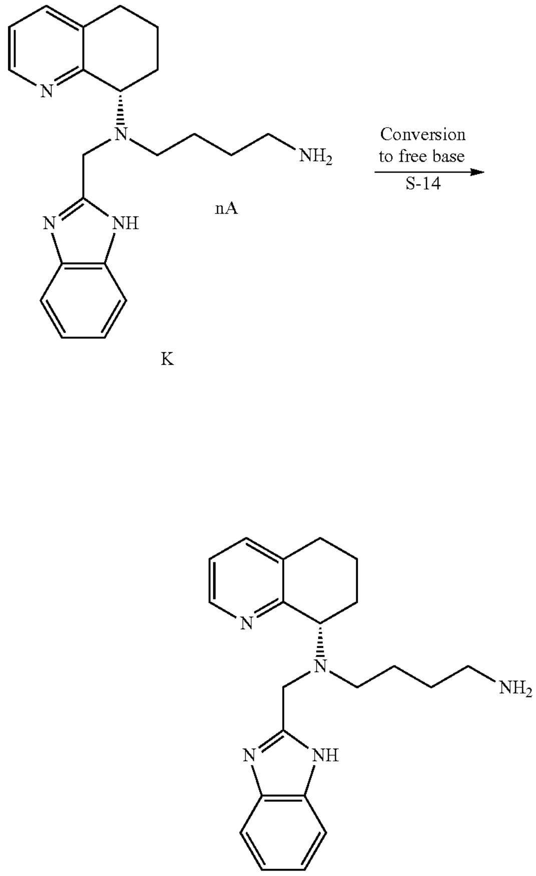

nA

K

Mavorixafor

In one aspect, the present invention provides methods for preparing compounds of formulae Q, P, O, N, M, K and mavorixafor according to the steps depicted in Scheme IV. In the compounds of present formulae, $R^2$ and $R^4$ are as defined above for compounds of formula F-2; $R^3$ and L are as defined above for compounds of formula F-3; A is selected from an acid such as TFA, HCl, HBr, $H_2SO_4$, $H_3PO_4$ and the like; and n is 1, 2 or 3.

In a certain embodiment, the compound O is a compound of the formula O-1:

O-1

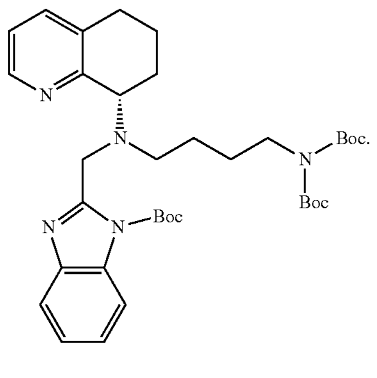

In an embodiment, the present invention provides a compound of the formula K-1:

K-1

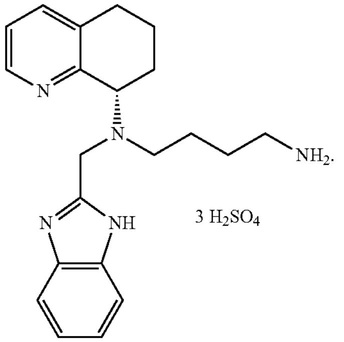

3 $H_2SO_4$

Compound K-1 can be synthesized by simultaneous deprotection of three Boc groups of compound O-1, by reacting O-1 with sulfuric acid, as depicted in Example 3 below. Attempts to crystallize mavorixafor with several other counter-ions have not been successful, or have resulted in products that were highly hygroscopic. Compound K-1 is a stable solid, that is easy to isolate, purify and store. Using K-1 gives better yields in the subsequent synthetic step compared to using other salt forms. At step S-8, a condensation reaction is carried out between the amino group of compound F-1 and the bisulfite adduct of the aldehyde group of a compound of formula F-2a to prepare an imine of formula Q. In some embodiments, compound F-1 is an acid addition salt thereof, such as the hydrochloride. According to one embodiment, $R^2$ is Boc. According to one embodiment, $R^4$ is Boc. According to another embodiment, $R^2$ and $R^4$ are both Boc. Imine formation via condensation between an amine and a bisulfite adduct of an aldehyde is well known to one of ordinary skill in the art; see, e.g., Expedient reductive amination of aldehyde bisulfite adducts, Neelakandha S. Mani et al, *Synthesis,* 2009, volume 23, page 4032, which is hereby incorporated by reference in its entirety. According to certain embodiments, compound F-1 is reacted with compound F-2a under appropriate condition. For example, in some embodiments, F-1 is reacted with F-2a in a mixture of THE and n-heptane in the presence of an aqueous phosphate solution, such as aqueous potassium phosphate. In some embodiments, the reaction is carried out at a reduced temperature, such as about −15 to 15° C. In some embodiments, the reaction is carried out at a reduced temperature, such as about −5 to 5° C. In one embodiment, compound F-1 is reacted with compound F-2a in a mixture of THF and n-heptane in presence of aqueous potassium phosphate at 0° C. According to certain embodiments, compound F-2a is added to the reaction mixture in 1 to 10 portions spaced by 1 to 60 minutes. In some embodiments, compound F-2a is added to the reaction mixture in 2 to 6 portions spaced by ≥10 minutes. In one embodiment, compound F-2a is added to the reaction mixture in four portions spaced by 10 minutes. According to certain embodiments, the reaction mixture is stirred for 0 to 10 hours. According to some embodiments, the reaction mixture is stirred for ≥1 hour. In one embodiment, the reaction mixture is stirred for 1.5 hours. According to one embodiment, the organic phase of the reaction mixture is directly used for step S-9. According to another embodiment, the compound Q is a non-isolated intermediate. In one embodiment, the reaction is performed as described in the Step 3A in Example 3 below.

At step S-9, the imine moiety of a compound of formula Q is reduced to prepare an amine of the formula P. According to one embodiment, $R^2$ is Boc. According to one embodiment, $R^4$ is Boc. According to another embodiment $R^2$ and $R^4$ are both Boc. Methods of reducing imines to prepare amines are well known to one of ordinary skill in the art; see, e.g., Expedient reductive amination of aldehyde bisulfite adducts, Neelakandha S. Mani et al, *Synthesis,* 2009, volume 23, page 4032-4036. In certain embodiments, imine Q is reacted with an appropriate reducing agent such as sodium borohydride in an appropriate solvent, such as a water-THF mixture. The reaction is optionally performed at a reduced temperature such as about −25 to 20° C. In some embodiments, imine Q is reacted with sodium borohydride in a water-THF mixture at −10 to 0° C. In one embodiment, imine Q is reacted with sodium borohydride in a water-THF mixture at −5° C. In one embodiment, imine Q is reacted with sodium borohydride in the presence of zinc chloride. In certain embodiments, the reaction mixture is stirred for 0 to 5 hours. In some embodiments, the reaction mixture is stirred for ≥1 hour. In one embodiment, the reaction mixture is stirred for 1.5 hours. In certain embodiments, amine P is isolated as an HCl salt by precipitation. In some embodiments, the isolation is performed by cooling a mixture of HCl salt of compound P and tert-butyl methyl ether, for example to about −25 to 20° C. In some embodiments, amine P is isolated as an HCl salt by precipitation by cooling a mixture of HCl salt of compound P and tert-butyl methyl ether to about −10 to 0° C. In one embodiment, amine P is isolated as an HCl salt by precipitation by cooling a mixture of HCl salt of compound P and tert-butyl methyl ether to −5° C. In certain embodiments, an HCl salt of compound P is dried under a flow of nitrogen at 10 to 50° C. In some embodiments, an HCl salt of compound P is dried under a flow of nitrogen at ≥25° C. In one embodiment, HCl salt of compound P is dried under a flow of nitrogen at 23° C. According to one embodiment the reaction is performed as described in U.S. patent application Ser. No. 16/215,963 (U.S. Pat. No. 10,548,889). In one embodiment, the reaction is performed as described in the Step 3B in Example 3 below.

At step S-10, a compound of formula P is reacted with a compound of formula F-3, to prepare a compound of formula O. According to one embodiment, $R^3$ is Boc. According to another embodiment, $R^2$ is Boc. According to one embodiment, $R^4$ is Boc. According to another embodiment $R^2$ and $R^4$ are both Boc. According to yet another embodiment L is chloro. According to yet another embodiment $R^2$ and $R^3$ are both Boc. According to yet another embodiment $R^2$, $R^3$ and $R^4$ are Boc. Methods for N-alkylation of amines are well known to one of ordinary skill in the art and typically include a reaction between an amine and a compound of formula $AG^1LG^5$, wherein $AG^1$ is an alkyl group and $LG^5$ is a suitable leaving group. Exemplary reactions include those described in detail in *Advanced Organic Chemistry: Reactions, Mechanisms, and Structure* (*3rd ed.*), Jerry March, New York: Wiley, ISBN 0-471-85472-7, the entirety of which is incorporated herein by reference. In certain embodiments, a compound of formula P is reacted with a compound of formula F-3, in the presence of potassium phosphate. In certain embodiments, a compound of formula P is reacted with a compound of formula F-3, in a mixture of toluene and purified water. In certain embodiments, a compound of formula P is reacted with a compound of formula F-3, in the presence of an iodide source such as sodium iodide, potassium iodide, or tetrabutylammonium iodide. In certain embodiments, the reaction is performed at an elevated temperature, such as about 20 to 75° C. In some embodiments, the reaction is performed at an elevated temperature, such as about 35 to 45° C. In one embodiment, the reaction is performed at 40° C. In certain embodiments, the reaction is performed by stirring the reaction mixture for 5 to 70 hours. In some embodiments, the reaction is performed by stirring the reaction mixture for ≥30 hours. In one embodiment, the reaction is performed by stirring the reaction mixture for about 30 hours. In certain embodiments, the reaction mixture is treated with 2-mercaptoacetic acid at 15 to 90° C. In some embodiments, the reaction mixture is treated with 2-mercaptoacetic acid at 45 to 55° C. In one embodiment, the reaction mixture is treated with 2-mercaptoacetic acid at 50° C. According to one embodiment, the organic phase of the reaction mixture is directly used for step S-11. According to a certain embodiment, compound O is a non-isolated intermediate. According to one embodiment, the reaction is performed as described in U.S. patent application Ser. No. 16/215,963 (U.S. Pat. No. 10,548,889). In one embodiment, the reaction is performed as described in the Step 3C in Example 3 below.

At step S-11, a compound of formula O is deprotected to remove protecting group $R^3$ to prepare a compound of formula N. Deprotection methods of benzimidazole protecting groups are well known in the art and include those described in detail in *Protecting Groups in Organic Synthesis*, T. W. Greene and P. G. M. Wuts, 3rd edition, John Wiley & Sons, 1999, the entirety of which is incorporated herein by reference.

At step S-12, a compound of formula N is deprotected to remove protecting group $R^2$ to prepare compound M. Deprotection methods of amine protecting groups are well known in the art and include those described in detail in *Protecting Groups in Organic Synthesis*, T. W. Greene and P. G. M. Wuts, 3rd edition, John Wiley & Sons, 1999, the entirety of which is incorporated herein by reference.

At step S-13, compound M is deprotected to remove protecting group $R^4$ to prepare compound K. Deprotection methods of amine protecting groups are well known in the art and include those described in detail in *Protecting Groups in Organic Synthesis*, T. W. Greene and P. G. M. Wuts, 3rd edition, John Wiley & Sons, 1999, the entirety of which is incorporated herein by reference.

In a certain embodiment, compound O is the compound of formula O-1; and the three Boc groups are removed in a single step to prepare a compound of formula K. In one embodiment, the three Boc groups of compound O-1 are removed in a single step to by reacting compound O-1 with $H_2SO_4$ to prepare a compound of formula K-1. Deprotection methods for removing multiple Boc groups in a single step are well known in the art and typically include reacting a compound bearing two or more Boc groups with an acid selected from TFA, HCl, HBr, $H_2SO_4$, and $H_3PO_4$. Exemplary methods include those described in detail in *Protecting Groups in Organic Synthesis*, T. W. Greene and P. G. M. Wuts, 3rd edition, John Wiley & Sons, 1999, the entirety of which is incorporated herein by reference. In certain embodiments, compound O-1 is reacted with $H_2SO_4$ in n-butanol at 20 to 90° C. In some embodiments, compound O-1 is reacted with $H_2SO_4$ in n-butanol at 50 to 60° C. In one embodiment, compound O-1 is reacted with $H_2SO_4$ in n-butanol at 55° C. In one embodiment, organic phase from Step S-10 containing compound O-1 is directly reacted with $H_2SO_4$ in n-butanol. In certain embodiments, compound O-1 is reacted with $H_2SO_4$ in n-butanol by stirring the reaction mixture for 0 to 10 hours. In some embodiments, compound O-1 is reacted with $H_2SO_4$ in n-butanol by stirring the reaction mixture for ≥1 hour. In one embodiment, compound O-1 is reacted with $H_2SO_4$ in n-butanol by stirring the reaction mixture for 1.5 hours. In certain embodiments, compound O-1 is reacted with $H_2SO_4$ in n-butanol by stirring the reaction mixture for additional 0 to 10 hours. In some embodiments, compound O-1 is reacted with $H_2SO_4$ in n-butanol by stirring the reaction mixture for additional 4 to 5 hours. In one embodiment, compound O-1 is reacted with $H_2SO_4$ in n-butanol by stirring the reaction mixture for additional 4.5 hours. In certain embodiments, product K-1 is precipitated directly from the reaction mixture by cooling the reaction mixture, for example, by cooling to about 0 to 40° C. over 1 to 30 hours. In some embodiments, product K-1 is precipitated directly from the reaction mixture by cooling the reaction mixture, for example, by cooling to about 15 to 25° C. over ≥10 hours. In one embodiment, product K-1 is precipitated directly from the reaction mixture by cooling the reaction mixture, for example, to about 20° C. over about 10 hours. In certain embodiments, product K-1 is isolated by filtration under nitrogen at a reduced temperature, for example at about 5 to 45° C. In some embodiments, product K-1 is isolated by filtration under nitrogen at a reduced temperature, for example at about 15 to 25° C. In one embodiment, product K-1 is isolated by filtration under nitrogen at about 20° C. In certain embodiments, precipitated product K-1 is washed with an appropriate non-polar solvent or mixture of non-polar solvents, such as benzene, toluene, xylenes, hexanes, pentane, heptane, n-hexanol, n-heptanol, and/or n-butanol. In some embodiments, the mixture of non-polar solvents is a mixture of about 1:10 to 10:1 volume/volume mixture of toluene and n-butanol. In some embodiments, the mixture of non-polar solvents is a mixture of about 4:1 volume/volume mixture of toluene and n-butanol. In some embodiments, precipitated product K-1 is washed with premixed 4:1 volume/volume mixture of toluene and n-butanol at about 5 to 50° C. In one embodiment, precipitated product K-1 is washed with premixed 4:1 volume/volume mixture of toluene and n-butanol at about 20° C. In certain embodiments, precipitated product K-1 is washed with toluene at about 5 to 55° C. In some embodiments, precipitated product K-1 is washed with toluene at about 15 to 25° C. In one embodiment, precipitated product K-1 is washed with toluene at about 20° C. In certain embodiments, after the washing step, product K-1 is dried under vacuum at 5 to 75° C. In some embodiments, after the washing step, product K-1 is dried under vacuum at ≤35° C. In one embodiment, after the washing step, product K-1 is dried under vacuum at about 30° C. In one embodiment, the reaction is performed as described in the Step 3D in Example 3 below.

At step S-14, a compound of formula K is converted to mavorixafor by reacting compound K with a base. Methods of converting acid salts of amines to corresponding free amines are well known in the art and typically include reacting an acid salt of an amine with a suitable base. In certain embodiments, compound K is reacted with a base selected from LiOH, NaOH, KOH, $Ca(OH)_2$, $Li_2CO_3$, $Na_2CO_3$, $K_2CO_3$, $CaCO_3$, $LiHCO_3$, $NaHCO_3$, $KHCO_3$, or $Ca(HCO_3)_2$. According to one embodiment, compound K is reacted with NaOH. According to one embodiment, compound K is reacted with aqueous NaOH. In certain embodiments, compound K-1 is reacted with aqueous NaOH in a biphasic solvent mixture of water, toluene and n-butanol. According to one embodiment, the aqueous NaOH solution is about 1 to 7 M. According to one embodiment, the aqueous NaOH solution is 3.0 M. According to some embodiments, as an optional step, after reaction of compound K with the base (such as NaOH), nitrogen-purged 0.1 to 2 M sulfuric acid is added to the resulting biphasic reaction mixture to adjust the pH of the aqueous layer to about 7 to 12, if the aqueous layer is not already at the pH of about 7 to 12. In one embodiment, as an optional step, after reaction of compound K with the base (such as NaOH), nitrogen-purged 0.3 M sulfuric acid is added to the resulting biphasic reaction mixture to adjust the pH of the aqueous layer to about 9.8 to 10.5, if the aqueous layer is not already at the pH of about 9.8 to 10.5. According to another embodiment, after reaction of compound K with the base (such as NaOH), the pH of the aqueous layer of the resulting biphasic reaction mixture is adjusted to about 8 to 12, if the aqueous layer is not already at the pH of about 8 to 12. According to yet another embodiment, after reaction of compound K with the base (such as NaOH), the pH of the aqueous layer of the resulting biphasic reaction mixture is adjusted to about 10.0, if the aqueous layer is not already at the pH of about 10. In certain embodiments, the reaction of compound K with the suitable base, after adjusting the pH of the aqueous layer to about 9.8 to 10.5, is performed at about 5 to 55° C. In some embodiments, the reaction of compound K with the suitable base, after adjusting the pH of the aqueous layer to about 9.8 to 10.5, is performed at about 25 to 35° C. According to one embodiment, the reaction is performed at about 30° C. In certain embodiments, after adjusting the pH of the aqueous layer to about 9.8 to 10.5, the reaction mixture is stirred for about 5 to 100 minutes. In some embodiments, the reaction mixture is stirred for about 30 to 60 minutes. In one embodiment, the reaction mixture is stirred for 45 minutes. In certain embodiments, the organic layer is of the reaction mixture is separated and n-butanol is removed by azeotrope by added toluene and vacuum distillation at 5 to 65° C. In some embodiments, the vacuum distillation is done at 35 to 45° C. According to one embodiment, the vacuum distillation is done at 40° C. According to another embodiment, azeotrope by added toluene is repeated 1 to 5 additional times. According to yet another embodiment, azeotrope by added toluene is repeated one additional time. In certain embodiments, the product, mavorixafor, is precipitated by concentrating the reaction mixture by vacuum distillation at about 5 to 65° C. According to one embodiment, mavorixafor is precipitated by concentrating the reaction mixture by vacuum distillation at about 35 to 45° C. According to another embodiment, mavorixafor is precipitated by concentrating the reaction mixture by vacuum distillation at about 30° C.

In certain embodiments, the precipitated mavorixafor is redissolved by heating the reaction mixture to about 30 to 90° C. This temperature is referred to as dissolution temperature. According to one embodiment, the dissolution temperature is about 60 to 66° C. According to another embodiment, the dissolution temperature is about 63° C. In some embodiments, the temperature of the solution of mavorixafor is adjusted to 0.5 to 5° C.±0.5° C. below the dissolution temperature. In some embodiments, the temperature of the solution of mavorixafor is adjusted to 2.5° C.±0.5° C. below the dissolution temperature. This temperature is referred to as seed temperature. In certain embodiments, the reaction mixture is seeded by addition of a slurry of mavorixafor in toluene at the seed temperature ±10° C. In some embodiments, the reaction mixture is seeded by addition of a slurry of mavorixafor in toluene at the seed temperature ±2° C. In certain embodiments, the reaction mixture is stirred at seed temperature ±5° C. for 0.5 to 5 hours. In some embodiments, the reaction mixture is stirred at seed temperature ±2° C. for ≥1 hour. In one embodiment, the reaction mixture is stirred at seed temperature ±2° C. for 1 hour. In certain embodiments, the reaction mixture is cooled to about 20 to 60° C. over about 0.5 to 10 hours. In some embodiments, the reaction mixture is cooled to about 38 to 42° C. over about 2.5 hours, or ≥2.5 hours. According to one embodiment, the reaction mixture is cooled to about 40° C. over about 2.5 hours. In certain embodiments, the reaction mixture is stirred at about 38 to 42° C. for about 1 hour, or ≥1 hour. According to one embodiment, the reaction mixture is stirred at about 40° C. for about 1 hour. In certain embodiments, the reaction mixture is further cooled to about 10 to 50° C. over about 0.5 to 10 hours. In some embodiments, the reaction mixture is further cooled to about 28 to 32° C. over about 2 hours, or ≥2 hours. According to one embodiment, the reaction mixture is further cooled to about 30° C. over about 2 hours. In certain embodiments, the reaction mixture is stirred at about 10 to 50° C. for about 0 to 10 hours. In some embodiments, the reaction mixture is stirred at about 28 to 32° C. for about 1 hour, or ≥1 hour. According to one embodiment, the reaction mixture is stirred at about 30° C. for about 1 hour. In certain embodiments, the reaction mixture is further cooled to about 10 to 40° C. over 10 to 100 minutes. In some embodiments, the reaction mixture is further cooled to about 23 to 27° C. over 50 minutes, or ≥50 minutes. According to one embodiment, the reaction mixture is cooled to about 25° C. over about 50 minutes. In certain embodiments, the reaction mixture is stirred at about 10 to 50° C. for about 0.5 to 10 hours. In some embodiments, the reaction mixture is stirred at about 23 to 27° C. for about 2 hours, or ≥2 hours. According to one embodiment, the reaction mixture is stirred at about 25° C. for about 2 hours. In certain embodiments, the reaction mixture is further cooled to about −10 to 15° C. over about 0.5 to 10 hours. In some embodiments, the reaction mixture is further cooled to about 0 to 5° C. over about 4 hours, or ≥4 hours. According to one embodiment, the reaction mixture is cooled to about 2° C. over about 4 hours. In certain embodiments, the reaction mixture is stirred at −5 to 25° C. for 5 to 25 hours. In some embodiments, the reaction mixture is stirred at 0 to 5° C. for ≥8 hours. According to one embodiment, the reaction mixture is stirred at about 2° C. for about 12 hours. In certain embodiments, product mavorixafor is isolated by filtration at about −10 to 25° C. In some embodiments, product mavorixafor is isolated by filtration at about 0 to 5° C. In one embodiment, product mavorixafor is isolated by filtration at about 2° C. In certain embodiments, solid product mavorixafor is washed with nitrogen purged toluene about −5 to 25° C. In some embodiments, solid product mavorixafor is washed with nitrogen purged toluene about 0 to 5° C. In one embodiment, solid product mavorixafor is washed with nitrogen purged toluene at about 2° C. In certain embodiments, product mavorixafor is dried under vacuum and a flow of nitrogen for about 0.5 to 10 hours. In some embodiments, product mavorixafor is dried under vacuum and a flow of nitrogen for about 1 hour, or ≥1 hour. In one embodiment, product mavorixafor is dried under vacuum and a flow of nitrogen for about 1.5 hours. In certain embodiments, product mavorixafor is dried under vacuum and a flow of nitrogen at about 10 to 75° C. In some embodiments, product mavorixafor is dried under vacuum and a flow of nitrogen at ≤45° C. In one embodiment, product mavorixafor is dried under vacuum and a flow of nitrogen at about 40° C. According to one embodiment the reaction is performed as described in U.S. patent application Ser. No. 16/215,963 (U.S. Pat. No. 10,548,889). In one embodiment, the reaction is performed as described in the Step 3E in Example 3 below.

In one aspect, the present invention provides a method for preparing mavorixafor:

Mavorixafor

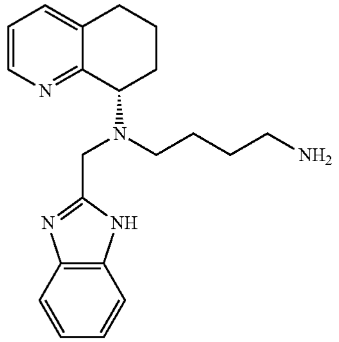

comprising the steps of:

(a) providing a compound of formula B:

B

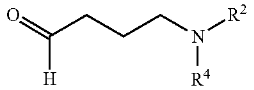

wherein:

$R^2$ and $R^4$ independently are a suitable amino protecting group;

(b) sulfonating the compound of formula B to form a compound of formula F-2a:

F-2a

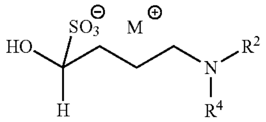

wherein:

M is a metal selected from alkali metals;

(c) condensing the compound of formula F-2a with compound F-1:

F-1

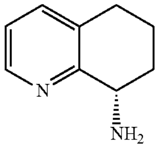

or a salt thereof, to form a compound of formula Q:

Q

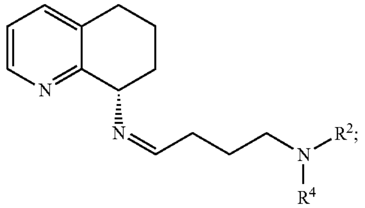

(d) reducing the compound of formula Q to form a compound of formula P:

P

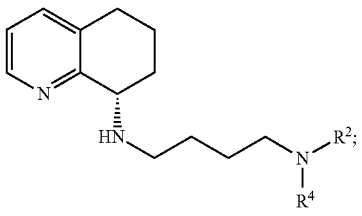

(e) reacting the compound of formula P with a compound of formula F-3:

F-3

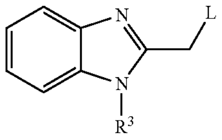

wherein:

$R^3$ is a suitable benzimidazole protecting group; and

L is a suitable leaving group;

to form a compound of formula O:

O

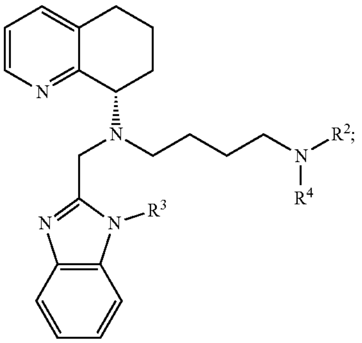

(f) deprotecting the compound of formula O to form a compound of formula N:

N

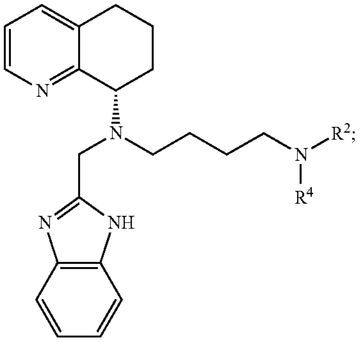

(g) deprotecting the compound of formula N to form a compound of formula M:

M

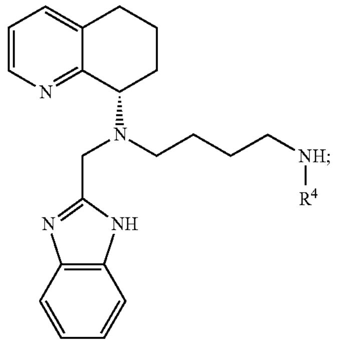

(h) deprotecting the compound of formula M to form a compound of formula K:

K

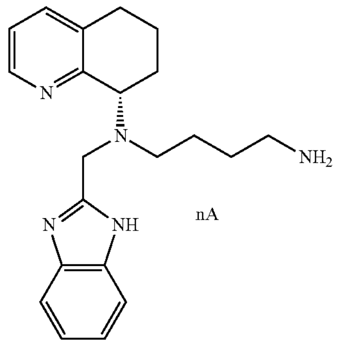

wherein:

A is an acid; and n is 1, 2 or 3;

and (i) converting the compound of formula K to form mavorixafor.

In certain embodiments, the $R^2$ group of formulae B, F-2a, Q, P, O and N is Boc. In one embodiment, $R^4$ group of formulae B, F-2a, Q, P, O, N and M is Boc. In another embodiment, $R^2$ and $R^4$ groups of formulae B, F-2a, Q, P, O, N and M are Boc. In certain embodiments, M of formulae F-2a is sodium or potassium. In certain embodiments, $R^3$ group of formulae F-3 and O is Boc. In certain embodiments, L group of formula F-3 is chloro. In certain embodiments, each occurrence of $R^2$, $R^3$ and $R^4$ is Boc. In certain embodiments, A in formula K is TFA, HCl, HBr, $H_3PO_4$ or $H_2SO_4$; and n is 1, 2 or 3. According to one embodiment, A in formula K is $H_2SO_4$; and n is 3. In certain embodiments, at step (c) the compound of formula Q is a non-isolated intermediate. In certain embodiments, at step (e) the compound of formula O is a non-isolated intermediate. In certain embodiments, the sulfonation at step (b) is achieved by reacting the compound of formula B with $MS_2O_5$, wherein M is an alkali metal. According to one embodiment, the alkali metal is sodium or potassium. In certain embodiments, the condensation of the compound of formula F-2a and the compound of formula F-1 at step (c) is catalyzed by a suitable condensation catalyst. According to one embodiment, the suitable condensation catalyst is $K_3PO_4$. In certain embodiments, the reduction at step (d) is achieved by reacting the compound of formula Q with a reducing agent selected from the group comprising $NaBH_4$, $NaCNBH_3$ and $BH_3$. According to one embodiment, the reducing agent is $NaBH_4$. In certain embodiments, the reaction at step (e) is achieved by reacting the compound of formula P with a compound of formula F-3a:

F-3a

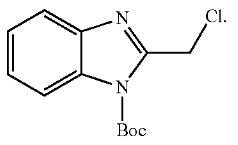

In certain embodiments, $R^2$, $R^3$ and $R^4$ are Boc; the deprotection at steps (f), (g) and (h) is achieved simultaneously to generate the compound of formula K, by reacting the compound of formula O with an acid selected from TFA, HCl, HBr, $H_3PO_4$, and $H_2SO_4$. According to one embodiment, the acid is $H_2SO_4$. According to another embodiment, A in the formula K is $H_2SO_4$; and n is 3. In certain embodiments, the reaction at step (i) is achieved by reacting the compound of formula K with a suitable base. According to one embodiment, the suitable base is NaOH.

In one aspect, the present invention provides a method for preparing a compound of formula K:

K

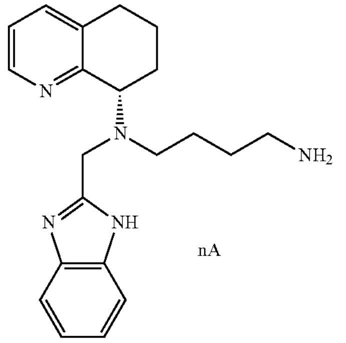

wherein:

A is an acid; and n is 1, 2 or 3;

comprising the steps of:

(a) providing a compound of formula B:

B

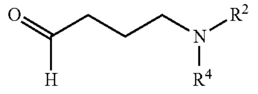

wherein:

$R^2$ and $R^4$ independently are each independently a suitable amino protecting group;

(b) sulfonating the compound of formula B to form a compound of formula F-2a:

F-2a

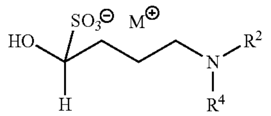

wherein:

M is a metal selected from alkali metals;

(c) condensing the compound of formula F-2a with compound F-1:

F-1

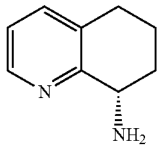

or a salt thereof, to form a compound of formula Q:

Q

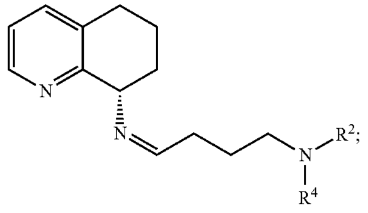

(d) reducing the compound of formula Q to form a compound of formula P:

P

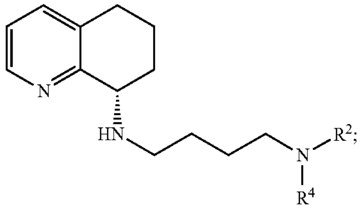

(e) reacting the compound of formula P with a compound of formula F-3:

F-3

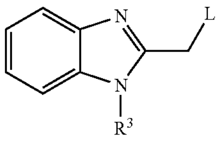

wherein:

$R^3$ is a suitable benzimidazole protecting group; and

L is a suitable leaving group;

to form a compound of formula O:

O

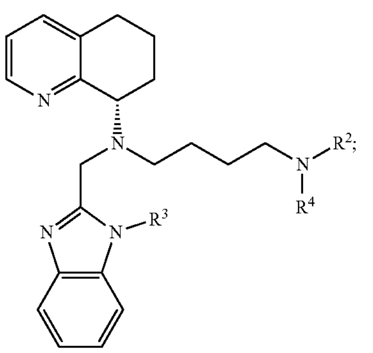

(f) deprotecting the compound of formula O to form a compound of formula N:

N

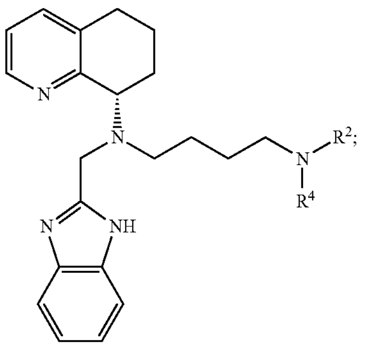

(g) deprotecting the compound of formula N to form a compound of formula M:

M

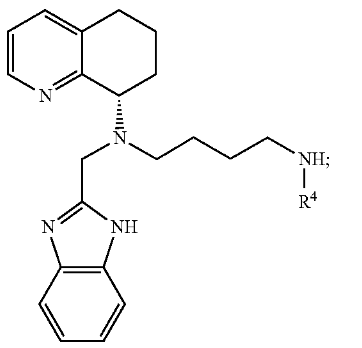

(h) deprotecting the compound of formula M to form the compound of formula K.

In certain embodiments, $R^2$ group of formulae B, F-2a, Q, P, O and N is Boc. In one embodiment, $R^4$ group of formulae B, F-2a, Q, P, O, N and M is Boc. In another embodiment, $R^2$ and $R^4$ groups of formulae B, F-2a, Q, P, O, N and M are Boc. In certain embodiments, M of formulae F-2a is sodium or potassium. In certain embodiments, $R^3$ group of formulae F-3 and O is Boc. In certain embodiments, L group of formula F-3 is chloro. In certain embodiments, each occurrence of $R^2$ and $R^3$ is Boc. In certain embodiments, A in formula K is TFA, HCl, HBr, $H_3PO_4$ or $H_2SO_4$; and n is 1, 2, or 3. In certain embodiments, A in formula K is $H_2SO_4$; and n is 3. In certain embodiments, at step (c) the compound of formula Q is a non-isolated intermediate. In certain embodiments, at step (e) the compound of formula O is a non-isolated intermediate. In certain embodiments, the sulfonation at step (b) is achieved by reacting the compound of formula B with $MS_2O_5$, wherein M is an alkali metal. According to one embodiment, the alkali metal is sodium or potassium. In certain embodiments, the condensation of the compound of formula F-2a and the compound of formula F-1 at step (c) is catalyzed by a suitable condensation catalyst. According to one embodiment, the suitable condensation catalyst is $K_3PO_4$. In certain embodiments, the reduction at step (d) is achieved by reacting the compound of formula Q with a reducing agent selected from the $NaBH_4$, $NaCNBH_3$, and $BH_3$. According to one embodiment, the reducing agent is $NaBH_4$. In certain embodiments, the reaction at step (e) is achieved by reacting the compound of formula P with a compound of formula F-3a.

F-3a

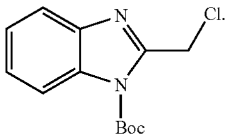

In certain embodiments, $R^2$, $R^3$ and $R^4$ are Boc; the deprotection at steps (f), (g) and (h) is achieved simultaneously to generate the compound of formula K, by reacting the compound of formula O with an acid selected from TFA, HCl, HBr, $H_3PO_4$, and $H_2SO_4$. According to one embodiment, the acid is $H_2SO_4$. According to another embodiment, A in the formula K is $H_2SO_4$; and n is 3.

In one aspect, the present invention provides a method for preparing a compound of formula P:

P

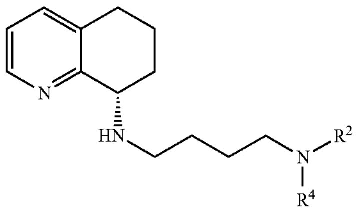

wherein:

$R^2$ and $R^4$ independently are a suitable amino protecting group;

comprising the steps of:

(a) providing a compound of formula B:

B

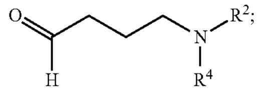

(b) sulfonating the compound of formula B to form a compound of formula F-2a:

F-2a

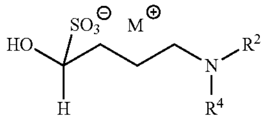

wherein:

M is a metal selected from alkali metals;

(c) condensing the compound of formula F-2a with compound F-1:

F-1

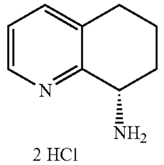

2 HCl or a salt thereof;

to form a compound of formula Q:

Q

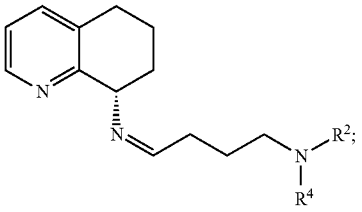

and (d) reducing the compound of formula Q to form the compound of formula P.

In certain embodiments, $R^2$ in formulae B, F-2a, Q and P is Boc. In one embodiment, $R^4$ group of formulae B, F-2a, Q and P is Boc. In another embodiment, $R^2$ and $R^4$ groups of formulae B, F-2a, Q and P are Boc. In certain embodiments, M in formula F-2a is sodium or potassium. In certain embodiments, at step (c) the compound of formula Q is a non-isolated intermediate. In certain embodiments, the sulfonation at step (b) is achieved by reacting the compound of formula B with $MS_2O_5$, wherein M is an alkali metal. According to one embodiment, the alkali metal is sodium or potassium. In certain embodiments, the condensation of the compound of formula F-2a and the compound of formula F-1 at step (c) is catalyzed by a suitable condensation catalyst. According to one embodiment, the suitable condensation catalyst is $K_3PO_4$. In certain embodiments, the reduction at step (d) is achieved by reacting the compound of formula Q with a reducing agent selected from $NaBH_4$, $NaCNBH_3$, and $BH_3$. According to one embodiment, the reducing agent is $NaBH_4$.

In one aspect, the present invention provides a method for preparing a compound of formula F-2a:

F-2a

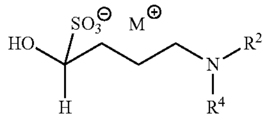

wherein:

$R^2$ and $R^4$ independently are a suitable amino protecting group; and

M is a metal selected from alkali metals;

comprising the steps of:

(a) providing a compound of formula B:

B

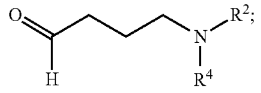

and (b) sulfonating the compound of formula B to form the compound of formula F-2a.

In certain embodiments, $R^2$ in formula B and F-2a is Boc. In one embodiment, $R^4$ group of formula B is Boc. In another embodiment, $R^2$ and $R^4$ groups of formula B are Boc. In certain embodiments, M in formula F-2a is sodium or potassium.

In one aspect, the present invention provides a compound of formula F-2:

F-2

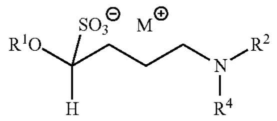

wherein:

$R^1$ is hydrogen, —C(O)R', —C(O)OR', —C(O)NR'R", —$S(O)_m$R', —$Si(R')_3$ or an optionally substituted group selected from $C_1$-$C_6$ alkyl, $C_1$-$C_6$ haloalkyl, $C_3$-$C_6$ cycloalkyl, $C_1$-$C_6$ alkoxy-$C_1$-$C_6$ alkyl, phenyl, aryl, or heteroaryl;

$R^2$ and $R^4$ are independently are hydrogen, —C(O)R', —C(O)OR', —C(O)NR'R", —$S(O)_m$R', —$Si(R')_3$ or an optionally substituted group selected from $C_1$-$C_6$ alkyl, $C_1$-$C_6$ haloalkyl, $C_3$-$C_6$ cycloalkyl, $C_1$-$C_6$ alkoxy-$C_1$-$C_6$ alkyl, phenyl, aryl, or heteroaryl;

R' and R" independently are hydrogen or an optionally substituted group selected from $C_{1-6}$ aliphatic, a 3-8 membered saturated or partially unsaturated monocyclic carbocyclic ring, phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur; and M is a metal selected from alkali metals.

In certain embodiments, $R^1$ is hydrogen. In certain embodiments, M is sodium or potassium. In certain embodiments, $R^2$ is hydrogen, Boc or Cbz. In certain embodiments, $R^4$ is hydrogen, Boc or Cbz. According to one embodiment, $R^2$ is Boc and M is sodium. According to one embodiment, $R^4$ is Boc and M is sodium. According to another embodiment, $R^2$ and $R^4$ are Boc and M is sodium.

In one aspect, the present invention provides a compound of formula K:

K

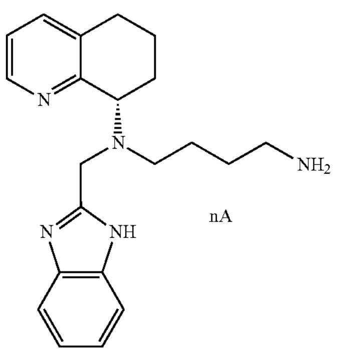

wherein:

A is TFA, HCl, HBr, $H_3PO_4$, or $H_2SO_4$; and n is 1, 2 or 3.

According to certain embodiments, n is 3. According to certain embodiments, A is $H_2SO_4$.

Compounds and Definitions

Compounds of the present invention include those described generally herein, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry," Thomas Sorrell, University Science Books, Sausalito: 1999, and "March's Advanced Organic Chemistry," 5$^{th}$ Ed., Ed.: Smith, M. B. and March, J., John Wiley & Sons, New York: 2001, the entire contents of which are hereby incorporated by reference.

The term "aliphatic" or "aliphatic group," as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle," "cycloaliphatic" or "cycloalkyl"), that has a single point of attachment to the rest of the molecule. Unless otherwise specified, aliphatic groups contain 1-6 aliphatic carbon atoms. In some embodiments, aliphatic groups contain 1-5 aliphatic carbon atoms. In other embodiments, aliphatic groups contain 1-4 aliphatic carbon atoms. In still other embodiments, aliphatic groups contain 1-3 aliphatic carbon atoms, and in yet other embodiments, aliphatic groups contain 1-2 aliphatic carbon atoms. In some embodiments, "cycloaliphatic" (or "carbocycle" or "cycloalkyl") refers to a monocyclic $C_3$-$C_6$ hydrocarbon that is completely saturated or that contains one or more units of unsaturation, but which is not aromatic, that has a single point of attachment to the rest of the molecule. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

As used herein, the term "bicyclic ring" or "bicyclic ring system" refers to any bicyclic ring system, i.e. carbocyclic or heterocyclic, saturated or having one or more units of unsaturation, having one or more atoms in common between the two rings of the ring system. Thus, the term includes any permissible ring fusion, such as ortho-fused or spirocyclic. As used herein, the term "heterobicyclic" is a subset of "bicyclic" that requires that one or more heteroatoms are present in one or both rings of the bicycle. Such heteroatoms may be present at ring junctions and are optionally substituted, and may be selected from nitrogen (including N-oxides), oxygen, sulfur (including oxidized forms such as sulfones and sulfonates), phosphorus (including oxidized forms such as phosphates), boron, etc. In some embodiments, a bicyclic group has 7-12 ring members and 0-4 heteroatoms independently selected from nitrogen, oxygen, or sulfur. As used herein, the term "bridged bicyclic" refers to any bicyclic ring system, i.e. carbocyclic or heterocyclic, saturated or partially unsaturated, having at least one bridge. As defined by IUPAC, a "bridge" is an unbranched chain of atoms or an atom or a valence bond connecting two bridgeheads, where a "bridgehead" is any skeletal atom of the ring system which is bonded to three or more skeletal atoms (excluding hydrogen). In some embodiments, a bridged bicyclic group has 7-12 ring members and 0-4 heteroatoms independently selected from nitrogen, oxygen, or sulfur. Such bridged bicyclic groups are well known in the art and include those groups set forth below where each group is attached to the rest of the molecule at any substitutable carbon or nitrogen atom. Unless otherwise specified, a bridged bicyclic group is optionally substituted with one or more substituents as set forth for aliphatic groups. Additionally or alternatively, any substitutable nitrogen of a bridged bicyclic group is optionally substituted. Exemplary bicyclic rings include:

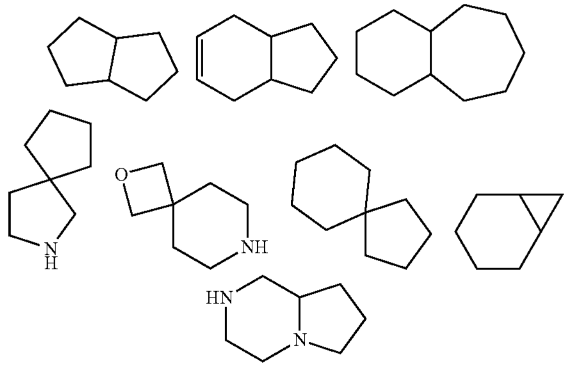

Exemplary bridged bicyclics include:

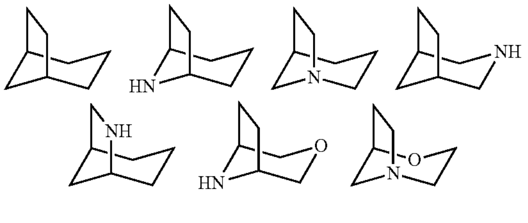

-continued

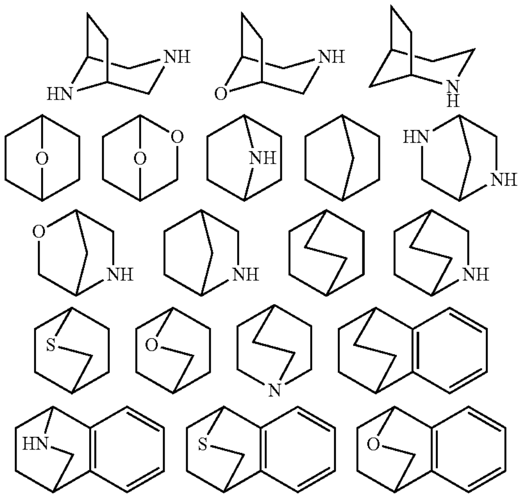

The term "lower alkyl" refers to a $C_{1-4}$ straight or branched alkyl group. Exemplary lower alkyl groups are methyl, ethyl, propyl, isopropyl, butyl, isobutyl, and tert-butyl.

The term "lower haloalkyl" refers to a $C_{1-4}$ straight or branched alkyl group that is substituted with one or more halogen atoms.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or $NR^+$ (as in N-substituted pyrrolidinyl)).

The term "unsaturated", as used herein, means that a moiety has one or more units of unsaturation.

As used herein, the term "bivalent $C_{1-8}$ (or $C_{1-6}$) saturated or unsaturated, straight or branched, hydrocarbon chain", refers to bivalent alkylene, alkenylene, and alkynylene chains that are straight or branched as defined herein.

The term "alkylene" refers to a bivalent alkyl group. An "alkylene chain" is a polymethylene group, i.e., $-(CH_2)_n-$, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

The term "alkenylene" refers to a bivalent alkenyl group. A substituted alkenylene chain is a polymethylene group containing at least one double bond in which one or more hydrogen atoms are replaced with a substituent. Suitable substituents include those described below for a substituted aliphatic group.

As used herein, the term "cyclopropylenyl" refers to a bivalent cyclopropyl group of the following structure:

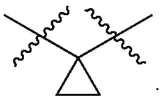 [SMILES: *C1(*)CC1]

The term "halogen" means F, Cl, Br, or I.

The term "aryl" used alone or as part of a larger moiety as in "aralkyl," "aralkoxy," or "aryloxyalkyl," refers to monocyclic or bicyclic ring systems having a total of five to fourteen ring members, wherein at least one ring in the system is aromatic and wherein each ring in the system contains 3 to 7 ring members. The term "aryl" may be used interchangeably with the term "aryl ring." In certain embodiments of the present invention, "aryl" refers to an aromatic ring system which includes, but not limited to, phenyl, biphenyl, naphthyl, anthracyl and the like, which may bear one or more substituents. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like.

The terms "heteroaryl" and "heteroar-," used alone or as part of a larger moiety, e.g., "heteroaralkyl," or "heteroaralkoxy," refer to groups having 5 to 10 ring atoms, preferably 5, 6, or 9 ring atoms; having 6, 10, or 14 $\pi$ electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono- or bicyclic. The term "heteroaryl" may be used interchangeably with the terms "heteroaryl ring," "heteroaryl group," or "heteroaromatic," any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle," "heterocyclyl," "heterocyclic radical," and "heterocyclic ring" are used interchangeably and refer to a stable 5- to 7-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or $^+NR$ (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl, pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle," "heterocyclyl," "heterocyclyl ring," "heterocyclic group," "heterocyclic moiety," and "heterocyclic radical," are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl. A heterocyclyl group may be mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Each optional substituent on a substitutable carbon is a monovalent substituent independently selected from halogen; $—(CH_2)_{0-4}R^\circ$; $—(CH_2)_{0-4}OR^\circ$; $—O(CH_2)_{0-4}R^\circ$, $—O—(CH_2)_{0-4}C(O)OR^\circ$; $—(CH_2)_{0-4}CH(OR^\circ)_2$; $—(CH_2)_{0-4}SR^\circ$; $—(CH_2)_{0-4}Ph$, which may be substituted with $R^\circ$; $—(CH_2)_{0-4}O(CH_2)_{0-1}Ph$ which may be substituted with $R^\circ$; $—CH{=}CHPh$, which may be substituted with $R^\circ$; $—(CH_2)_{0-4}O(CH_2)_{0-1}$-pyridyl which may be substituted with $R^\circ$; $—NO_2$; —CN; $—N_3$; $—(CH_2)_{0-4}N(R^\circ)_2$; $—(CH_2)_{0-4}N(R^\circ)C(O)R^\circ$; $—N(R^\circ)C(S)R^\circ$; $—(CH_2)_{0-4}N(R^\circ)C(O)NR^\circ_2$; $—N(R^\circ)C(S)NR^\circ_2$; $—(CH_2)_{0-4}N(R^\circ)C(O)OR^\circ$; $—N(R^\circ)N(R^\circ)C(O)R^\circ$; $—N(R^\circ)N(R^\circ)C(O)NR^\circ_2$; $—N(R^\circ)N(R^\circ)C(O)OR^\circ$; $—(CH_2)_{0-4}C(O)R^\circ$; $—C(S)R^\circ$; $—(CH_2)_{0-4}C(O)OR^\circ$; $—(CH_2)_{0-4}C(O)SR^\circ$; $—(CH_2)_{0-4}C(O)OSiR^\circ_3$; $—(CH_2)_{0-4}OC(O)R^\circ$; $—OC(O)(CH_2)_{0-4}SR—$, $SC(S)SR^\circ$; $—(CH_2)_{0-4}SC(O)R^\circ$; $—(CH_2)_{0-4}C(O)NR^\circ_2$; $—C(S)NR^\circ_2$; $—C(S)SR^\circ$; $—SC(S)SR^\circ$, $—(CH_2)_{0-4}OC(O)NR^\circ_2$; $—C(O)N(OR^\circ)R^\circ$; $—C(O)C(O)R^\circ$; $—C(O)CH_2C(O)R^\circ$; $—C(NOR^\circ)R^\circ$; $—(CH_2)_{0-4}SSR^\circ$; $—(CH_2)_{0-4}S(O)_2R^\circ$; $—(CH_2)_{0-4}S(O)_2OR^\circ$; $—(CH_2)_{0-4}OS(O)_2R^\circ$; $—S(O)_2NR^\circ_2$; —S(O)(NR□)R□; $—S(O)_2N{=}C$(NR□2)$_2$; $—(CH_2)_{0-4}S(O)R^\circ$; $—N(R^\circ)S(O)_2NR^\circ_2$; $—N(R^\circ)S(O)_2R^\circ$; $—N(OR^\circ)R^\circ$; $—C(NH)NR^\circ_2$; $—P(O)_2R^\circ$; $—P(O)R^\circ_2$; $—OP(O)R^\circ_2$; $—OP(O)(OR^\circ)_2$; $SiR^\circ_3$; $—(C_{1-4}$ straight or branched alkylene)$O—N(R^\circ)_2$; or $—(C_{1-4}$ straight or branched alkylene)$C(O)O—N(R^\circ)_2$.

Each $R^\circ$ is independently hydrogen, $C_{1-6}$ aliphatic, $—CH_2Ph$, $—O(CH_2)_{0-1}Ph$, $—CH_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of $R^\circ$, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted by a divalent substituent on a saturated carbon atom of $R^\circ$ selected from =O and =S; or each $R^\circ$ is optionally substituted with a monovalent substituent independently selected from halogen, $—(CH_2)_{0-2}R^\bullet$, -(halo$R^\bullet$), $—(CH_2)_{0-2}OH$, $—(CH_2)_{0-2}OR^\bullet$, $—(CH_2)_{0-2}CH(OR^\bullet)_2$; —O(halo$R^\bullet$), —CN, $—N_3$, $—(CH_2)_{0-2}C(O)R^\bullet$, $—(CH_2)_{0-2}C(O)OH$, $—(CH_2)_{0-2}C(O)OR^\bullet$, $—(CH_2)_{0-2}SR^\bullet$, $—(CH_2)_{0-2}SH$, $—(CH_2)_{0-2}NH_2$, $—(CH_2)_{0-2}NHR^\bullet$, $—(CH_2)_{0-2}NR'_2$, $—NO_2$, $—SiR^\bullet_3$, $—OSiR^\bullet_3$, $—C(O)SR^\bullet$, $—(C_{1-4}$ straight or branched alkylene)$C(O)OR^\bullet$, or $—SSR^\bullet$.

Each $R^\bullet$ is independently selected from $C_{1-4}$ aliphatic, $—CH_2Ph$, $—O(CH_2)_{0-1}Ph$, or a 5-6-membered saturated, partially unsaturated, or aryl ring having 0-4 heteroatoms independently selected from nitrogen, oxygen, or sulfur, and wherein each $R^\bullet$ is unsubstituted or where preceded by halo is substituted only with one or more halogens; or wherein an optional substituent on a saturated carbon is a divalent substituent independently selected from =O, =S, $=NNR^*_2$, $=NNHC(O)R^*$, $=NNHC(O)OR^*$, $=NNHS(O)_2R^*$, $=NR^*$, $=NOR^*$, $—O(C(R^*_2))_{2-3}O—$, or $—S(C(R^*_2))_{2-3}S—$, or a divalent substituent bound to vicinal substitutable carbons of an "optionally substituted" group is $—O(CR^*_2)_{2-3}O—$, wherein each independent occurrence of $R^*$ is selected from hydrogen, $C_{1-6}$ aliphatic or an unsubstituted 5-6-membered saturated, partially unsaturated, or aryl ring having 0-4 heteroatoms independently selected from nitrogen, oxygen, or sulfur.

When $R^*$ is $C_{1-6}$ aliphatic, $R^*$ is optionally substituted with halogen, $—R^\bullet$, -(halo$R^\bullet$), —OH, $—OR^\bullet$, —O(halo$R^\bullet$), —CN, —C(O)OH, $—C(O)OR^\bullet$, $—NH_2$, $—NHR^\bullet$, $—NR'_2$, or $—NO_2$, wherein each R' is independently selected from $C_{1-4}$ aliphatic, $—CH_2Ph$, $—O(CH_2)_{0-1}Ph$, or a 5-6-membered saturated, partially unsaturated, or aryl ring having 0-4 heteroatoms independently selected from nitrogen, oxygen, or sulfur, and wherein each $R^\bullet$ is unsubstituted or where preceded by halo is substituted only with one or more halogens.

An optional substituent on a substitutable nitrogen is independently $—R^\dagger$, $—NR^\dagger_2$, $—C(O)R^\dagger$, $—C(O)OR^\dagger$, $—C(O)C(O)R^\dagger$, $—C(O)CH_2C(O)R^\dagger$, $—S(O)_2R^\dagger$, $—S(O)_2NR^\dagger_2$, $—C(S)NR^\dagger_2$, $—C(NH)NR^\dagger_2$, or $—N(R^\dagger)S(O)_2R^\dagger$; wherein each $R^\dagger$ is independently hydrogen, $C_{1-6}$ aliphatic, unsubstituted —OPh, or an unsubstituted 5-6-membered saturated, partially unsaturated, or aryl ring having 0-4 heteroatoms independently selected from nitrogen, oxygen, or sulfur, or, two independent occurrences of $R^\dagger$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur; wherein when $R^\dagger$ is $C_{1-6}$ aliphatic, $R^\dagger$ is optionally substituted with halogen, $—R^\bullet$, -(halo$R^\bullet$), —OH, $—OR^\bullet$, —O(halo$R^\bullet$), —CN, —C(O)OH, —C(O)OR', $—NH_2$, $—NHR^\bullet$, $—NR^\bullet_2$, or $—NO_2$, wherein each $R^\bullet$ is independently selected from $C_{1-4}$ aliphatic, $—CH_2Ph$, $—O(CH_2)_{0-1}Ph$, or a 5-6-membered saturated, partially unsaturated, or aryl ring having 0-4 heteroatoms independently selected from nitrogen, oxygen, or sulfur, and wherein each $R^\bullet$ is unsubstituted or where preceded by halo is substituted only with one or more halogens.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

Salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}C$- or $^{14}C$-enriched carbon are within the scope of this invention. Such compounds are useful, for example, as analytical tools, as probes in biological assays, or as therapeutic agents in accordance with the present invention. In certain embodiments, a warhead moiety, $R^1$, of a provided compound comprises one or more deuterium atoms.

As used herein, the term "inhibitor" is defined as a compound that binds to and/or inhibits CXCR4 with measurable affinity. In certain embodiments, an inhibitor has an $IC_{50}$ and/or binding constant of less than about 100 μM, less than about 50 μM, less than about 1 μM, less than about 500 nM, less than about 100 nM, less than about 10 nM, or less than about 1 nM.

The terms "measurable affinity" and "measurably inhibit," as used herein, means a measurable change in CXCR4 activity between a sample comprising a compound of the present invention, or composition thereof, and CXCR4, and an equivalent sample comprising CXCR4, in the absence of said compound, or composition thereof.

EXEMPLIFICATION

Example 1: Synthesis of Sulfonate Adduct F-2d

Scheme V

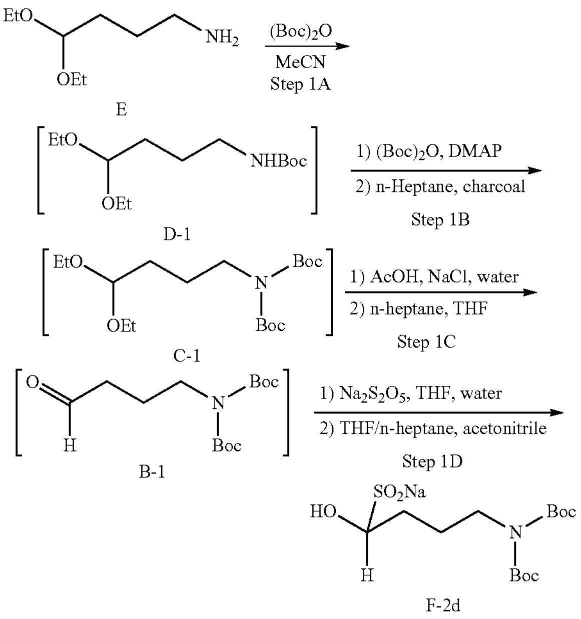

Step 1A: Preparation of D-1

Charge diethyl-4-aminobutyl acetal (E) (1.00 wt, 1.00 eq) to vessel A. Charge acetonitrile (10.0 vol, 7.8 wt) and adjust temperature to 20° C. Heat the mixture to 40° C. Concentrate the reaction mixture to 6.0 vol under reduced pressure at 35 to 45° C.

Charge acetonitrile (5.0 vol, 3.9 wt) at 35 to 45° C. Concentrate the reaction mixture to 6.0 vol under reduced pressure 35 to 45° C. This step is repeated once as described below.

Charge acetonitrile (5.0 vol, 3.9 wt) at 35 to 45° C. Concentrate the reaction mixture to 6.0 vol under reduced pressure at 35 to 45° C. Cool to 20° C.

Charge di-tert-butyl dicarbonate (1.1 eq, 1.5 wt) to a drum, followed by acetonitrile (0.4 vol, 0.3 wt) and agitate until fully dissolved. Concentrate the reaction mixture to 6.0 vol under reduced pressure at 35 to 45° C.

Charge this di-tert-butyl dicarbonate solution in acetonitrile to vessel A maintaining 20° C. Charge acetonitrile (1.5 vol, 1.1 wt) to the solution as a line rinse and stir at 20° C. for 30 to 60 min.

Charge 4-dimethylaminopyridine (0.076 wt, 0.10 eq) to the vessel A at 20° C. Heat the solution to 40° C. Concentrate the reaction mixture to 5.0 vol under reduced pressure. Charge acetonitrile (5.0 vol, 3.9 wt) to the solution. Concentrate the reaction mixture to 5.0 vol under reduced pressure.

Take the resulting solution of D-1 into next reaction without isolation.

Step 1B: Preparation of C-1

Charge acetonitrile (2.0 vol, 1.6 wt) at 35 to 45° C. to vessel A containing solution of D-1 from Step 1A.

Charge di-tert-butyl dicarbonate (1.4 eq, 1.9 wt) to a drum, followed by acetonitrile (10.0 vol, 7.8 wt) and agitate until fully dissolved. Charge this di-tert-butyl dicarbonate solution to vessel A, 2 to 6 h while distilling under vacuum at 35 to 45° C. maintaining the volume of the reaction at 7.0 vol. Charge acetonitrile (3.0 vol, 2.4 wt) over 20 to 40 min. as a line rinse while distilling under vacuum at 35 to 45° C., maintaining the volume of the reaction at 7.0 vol.

Charge di-tert-butyl dicarbonate, (0.14 eq, 0.19 wt) to a drum, followed by acetonitrile (1.0 vol, 0.74 wt) and agitate until fully dissolved. Charge this di-tert-butyl dicarbonate solution to vessel A over 20 to 40 min. Charge acetonitrile (0.3 vol, 0.24 wt) over 10 to 20 min as a line rinse while distilling under vacuum at 35 to 45° C., maintaining the volume of the reaction at 7.0 vol.

Concentrate the reaction mixture to 5.0 vol distilling under vacuum at 35 to 45° C.

Charge n-heptane, (7.5 vol, 5.1 wt) to the reaction mixture, and concentrate the reaction mixture to 5.0 vol under reduced pressure at 40° C. This step is repeated once as described below.

Charge n-heptane, (7.5 vol, 5.1 wt) to the reaction mixture, and concentrate the reaction mixture to 5.0 vol under reduced pressure at 40° C.

Charge decolorizing, activated charcoal (0.2 wt) to the solution and stir for 1 to 2 h at 40° C. Filter the reaction mixture at 40° C. Charge n-heptane, (2.0 vol, 1.4 wt) to the reactor vessel and stir for 5 to 15 min. at 20° C. before charging to the filter as a line rinse. Combine the filtrate and wash, and as required adjust to 20° C.

Take the resulting solution of C-1 into next reaction without isolation.

Step 1C: Preparation of B-1

Charge 15% v/v acetic acid (2.0 vol) caution gas evolution, to vessel A containing solution of C-1 from Step 1B, maintaining the temperature at 20° C. and stir for 10 min. at 20° C. Allow the phases to separate for 15 min. at 20° C. Discharge the aqueous phase to waste, retaining the organic phase in vessel A. This step is repeated once as described below.

Charge 15% v/v acetic acid (2.0 vol) maintaining 20° C. and stir for 10 min. at 20° C. Allow the phases to separate for 15 min. at 20° C. Discharge the aqueous phase to waste, retaining the organic phase in vessel A.

Adjust the reaction to 30° C. Charge 4% w/w sodium chloride solution (2.1 vol) to the vessel maintaining the temperature at 30° C. Charge glacial acetic acid (4.1 vol, 4.3 wt) to the vessel maintaining 30° C. Stir the reaction mixture for 2 h maintaining the temperature at 30° C.

Charge purified water, (6.0 vol) at 30° C. Stir the contents for 5 to 10 min. at 30° C., and separate the phases, retaining the upper organic phase in vessel A. Charge the lower aqueous phase to vessel B.

Charge purified water (4.0 vol) at 30° C. and stir for 5 to 10 min. maintaining the temperature at 30° C. Separate the phases at 30° C., retaining the upper organic phase in vessel A. Charge the lower aqueous phase to vessel B.

Adjust the temperature to 30° C. of vessel B containing combined aqueous phases. Charge n-heptane, (2.0 vol, 1.4 wt) to vessel B and stir for 5 to 10 min. maintaining the temperature at 30° C. Separate the phases at 30° C., over 15 min. Charge the upper organic phase to vessel A and recharge the lower aqueous phase to vessel B. This step is repeated two additional times as described below.

Charge n-heptane, (2.0 vol, 1.4 wt) to vessel B and stir for 5 to 10 min. maintaining the temperature at 30° C. Separate the phases at 30° C., over 15 min. Charge the upper organic phase to vessel A and recharge the lower aqueous phase to vessel B.

Charge n-heptane, (2.0 vol, 1.4 wt) to vessel B and stir for 5 to 10 min. maintaining the temperature at 30° C. Separate the phases at 30° C., over 15 min., discharge the lower aqueous phase to waste and charge the upper organic layer to vessel A.

Concentrate the combined organic phases in vessel A to 3.0 vol at 10 to 20° C. under reduced pressure. Offload the solution to new HDPE drum(s) and line rinse with n-heptane (0.5 vol, 0.4 wt) at 20° C. Homogenize the drum and store as "B-1 solution in n-heptane," and take into next reaction without isolation.

Step 1D: Preparation of F-2d

Calculate a new 1.00 wt based on the above assay.

Charge "B-1 solution in n-heptane" from Step 1C (1.00 wt, 1.00 eq, corrected for w/w assay, ca. 3.0 vol), into an appropriate vessel. Charge THF (3.0 vol, 2.7 wt). Heat the reaction mixture to 40° C.

Charge purified water, (0.02 vol, 0.02 wt) followed by sodium metabisulfite, (0.125 eq, 0.08 wt) as a solid via the charge hole at 40° C. Stir the resulting mixture for 30 to 35 min. at 40° C. This step was repeated four additional times to add the reagent in five portions total, as detailed below.

Charge purified water, (0.02 vol, 0.02 wt) followed by sodium metabisulfite, (0.125 eq, 0.08 wt) as a solid via the charge hole at 40° C. Stir the resulting mixture for 30 to 35 min. at 40° C.

Charge purified water, (0.02 vol, 0.02 wt) followed by sodium metabisulfite, (0.125 eq, 0.08 wt) as a solid via the charge hole at 40° C. Stir the resulting mixture for 30 to 35 min. at 40° C.

Charge purified water, (0.02 vol, 0.02 wt) followed by sodium metabisulfite, (0.125 eq, 0.08 wt) as a solid via the charge hole at 40° C. Stir the resulting mixture for 30 to 35 min. at 40° C.

Charge purified water, (0.02 vol, 0.02 wt) followed by sodium metabisulfite, (0.125 eq, 0.08 wt) as a solid via the charge hole at 40° C. Stir the resulting mixture for 36 h at 40° C.

Cool the reaction mixture to 20° C. over 3 to 4 h at a target constant rate. Filter the reaction mixture at 20° C. on a 1-2 μm cloth.

Wash the solid with a pre-mixed mixture of THF (0.5 vol, 0.5 wt) and n-heptane (0.5 vol, 0.3 wt) maintaining the temperature at 20° C. This step was repeated an additional three times, as detailed below.

Wash the solid with n-heptane, (2.0 vol, 1.4 wt) as a line rinse and apply to the filter-cake at 20° C.

Wash the solid with n-heptane, (2.0 vol, 1.4 wt) as a line rinse and apply to the filter-cake at 20° C.

Wash the solid with acetonitrile, (2.0 vol, 1.6 wt) as a line rinse and apply to the filter-cake at 20° C.

Dry the solid at 38° C. under a flow of nitrogen for 12 h.

Determine residual solvent content. Pass criteria acetonitrile ≤2.0% w/w, n-heptane ≤2.0% w/w and tetrahydrofuran ≤2.0% w/w.

Yield of compound F-2d: 52-69%.

$^{1}H$ NMR (400 MHz, $d_6$-DMSO): δ 5.22 (s, 1H), 3.77 (s, 1H), 3.45 (t, 2H), 1.70 (m, 2H), 1.44 (m, 20H). $^{13}C$ NMR (400 MHz, $d_6$-DMSO): δ 152.6, 83.2, 82.0, 46.5, 29.6, 28.1, 26.0. FTIR (wavenumber, $cm^{-1}$) 3294, 1721, 1738, 1367, 1233, 1180, 1135, 1109, 1045.

Example 2: Synthesis of F-3a

Scheme VI

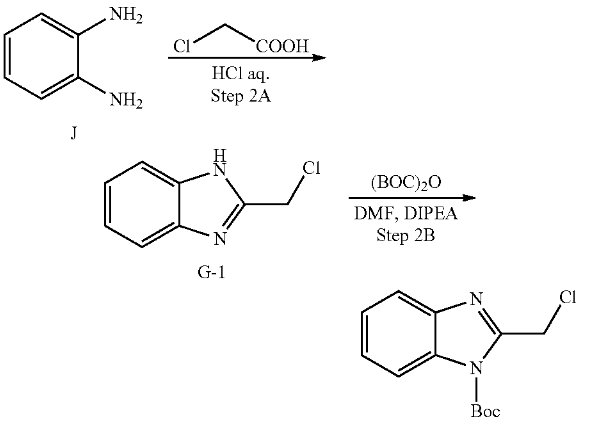

J

G-1

F-3a

Step 2A: Preparation of G-1

Charge J, (1.00 wt, 1.00 eq) to vessel A. Charge purified water, (1.0 vol, 1.0 wt) to vessel A and as necessary adjust the temperature to 20° C. Charge concentrated hydrochloric acid, (4.0 eq, 3.0 vol, 3.6 wt) to vessel A maintaining the temperature at 20° C. Line rinse with purified water, (0.5 vol, 0.5 wt) maintaining the contents of vessel A at 15 to 25° C.

Charge chloroacetic acid, (1.3 wt, 1.5 eq) and purified water, (1.0 vol, 1.0 wt) to vessel B and as necessary, adjust the temperature to 20° C. Stir until fully dissolved, expected 10 to 20 min.

Charge the chloroacetic acid solution to vessel A maintaining the temperature of vessel A at 20° C. Line rinse vessel A with purified water, (0.5 vol, 0.5 wt) at 15 to 25° C. and charge to vessel B at 20° C. Heat the reaction mixture to 80° C. Stir the reaction mixture at 80° C. for 20 h.

Cool the reaction mixture to 10° C. over 1.5 h. Charge 47% w/w potassium phosphate solution (6.0 vol) over 60 min. targeting a constant rate maintaining 10° C. Adjust the pH of the reaction mixture by charging 47% w/w potassium phosphate solution to pH 7.0 maintaining the reaction temperature at 10° C. Expected charge is 2.0 to 3.5 vol 47% w/w potassium phosphate solution.

Stir the slurry for ≥30 min. maintaining 10° C. and recheck the pH, pass criterion pH 7.0. Filter the reaction mixture through 20 μm cloth at 10° C. Wash the filter-cake with purified water, (1.0 vol, 1.0 wt) at 10° C. This step is repeated additional three times as described below.

Slurry wash the filter-cake in the reactor vessel with purified water, (10.0 vol, 10.0 wt) for 45 min. to 90 min. at 10° C. Filter the mixture through 20 μm cloth at 10° C.

Slurry wash the filter-cake in the reactor vessel with purified water, (10.0 vol, 10.0 wt) for 45 min. to 90 min. at 10° C. Filter the mixture through 20 μm cloth at 10° C.

Slurry wash the filter-cake in the reactor vessel with purified water, (10.0 vol, 10.0 wt) for 45 min. to 90 min. at 10° C. Filter the mixture through 20 μm cloth at 10° C.

Wash the filter-cake with purified water, (1.0 vol, 1.0 wt) at 10° C. The filter-cake was washed with purified water additional five times as described below.

Wash the filter-cake with purified water, (1.0 vol, 1.0 wt) at 10° C.

Wash the filter-cake with acetonitrile, (2×1.3 vol, 2×1.0 wt) at 10° C.

Dry the filter-cake on the filter under vacuum and strong nitrogen flow through the filter cake at 20° C. until the water content is ≤15.0% w/w by Karl-Fisher analysis.

Dry the filter-cake on the filter under vacuum and strong nitrogen flow through the filter cake at 30° C. until the water content is 5.0% w/w by Karl-Fisher analysis.

Dry the filter-cake on the filter under vacuum and strong nitrogen flow through the filter cake at 50° C. until the water content is ≤1.0% w/w by Karl-Fisher analysis.

Yield of compound G-1: about 75%.

Step 2B: Preparation of F-3a

Charge di-tert-butyl dicarbonate, (1.85 wt, 1.4 eq) to vessel A followed by N,N-dimethylformamide, (2.6 wt, 2.7 vol) and stir at 20° C. for 20 min. until dissolution achieved. Add N,N-diisopropylethylamine, (0.08 wt, 0.11 vol, 0.1 eq) to contents of vessel A at 20° C. Heat the contents of vessel A to 40° C.

Charge G-1, (1.00 wt) to vessel B followed by N,N-dimethylformamide, (5.2 wt, 5.5 vol) and adjust to 14° C.

Charge the G-1/DMF solution from vessel B to vessel A over 5 h at 40° C., at an approximately constant rate. Line rinse with N,N-dimethylformamide, (0.4 wt, 0.4 vol), maintaining vessel A at 40° C. Stir the resulting reaction mixture at 40° C. for 16 h.

Charge decolorizing charcoal activated, (0.20 wt). Adjust the mixture to 40° C. and stir at 40° C. for 60 to 90 min.

Clarify (filter) the reaction mixture into vessel B at 40° C. Charge N,N-dimethylformamide, (0.9 wt, 1.0 vol) via vessel A and filter at 40° C. Charge purified water, (3.5 vol) to the combined filtrates, over 60 min., maintaining the temperature at 40° C. As required, cool the mixture to 35° C. over 30 to 60 min.

Charge F-3a, (0.02 wt) as seed material at 35° C. Stir at 34° C. for 1.5 h then check for crystallization. Cool slurry to 30° C. over 40 min.

Charge F-3a, (0.02 wt) as seed material at 30° C. Stir at 30° C. for 1.5 h then check for crystallization.

Cool slurry to 20° C. over 3.5 h at a targeted constant rate. Stir at 20° C. for 3 h. Charge purified water, (1.0 vol), maintaining the temperature at 20° C. over 60 min.

Stir at 20° C. for 3 h.

Cool slurry to 2° C. over 2.5 h. Stir at 2° C. for 2.5 h. Filter through 20 μm cloth and pull dry until no further filtrate passes. Wash the solid with pre-mixed N,N-dimethylformamide/purified water, (2.0 vol, 1:2 v:v) at 2° C. Wash the solid with purified water, (2×3.0 vol) at 2° C. Dry under vacuum at 28° C. until KF ≤0.2% w/w, and N,N-dimethylformamide ≤0.4% w/w.

Yield of compound F-3a: 62-70%.

Example 3: Synthesis of Mavorixafor

Scheme VI

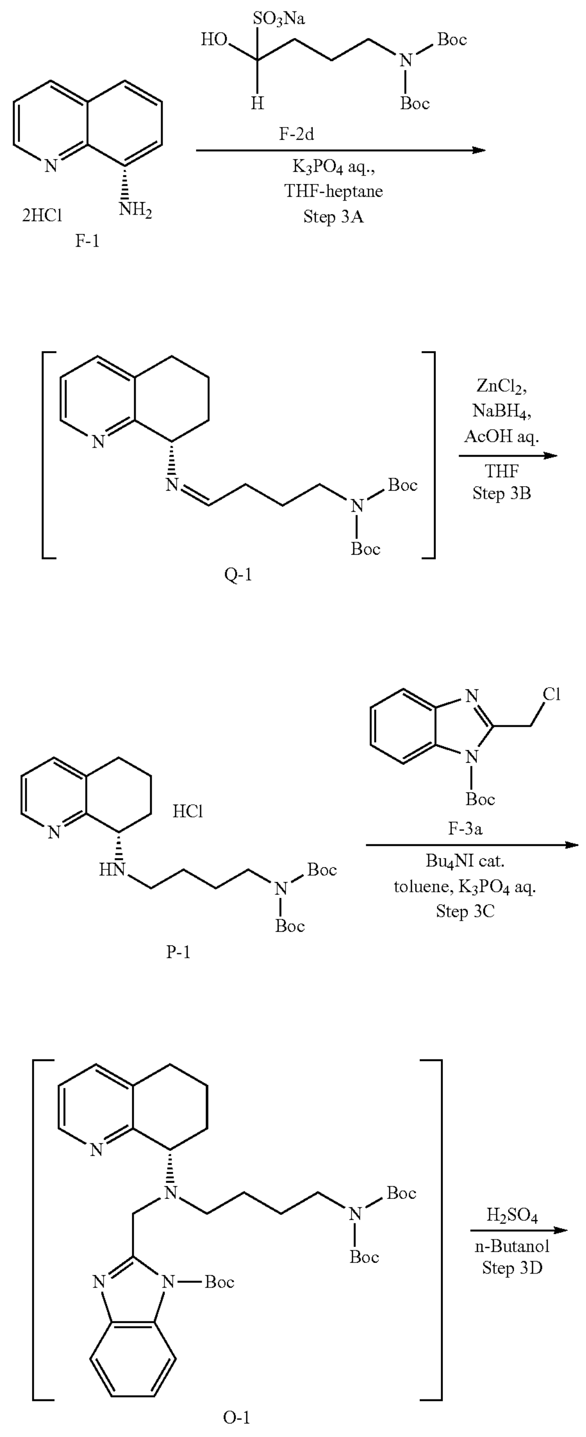

-continued

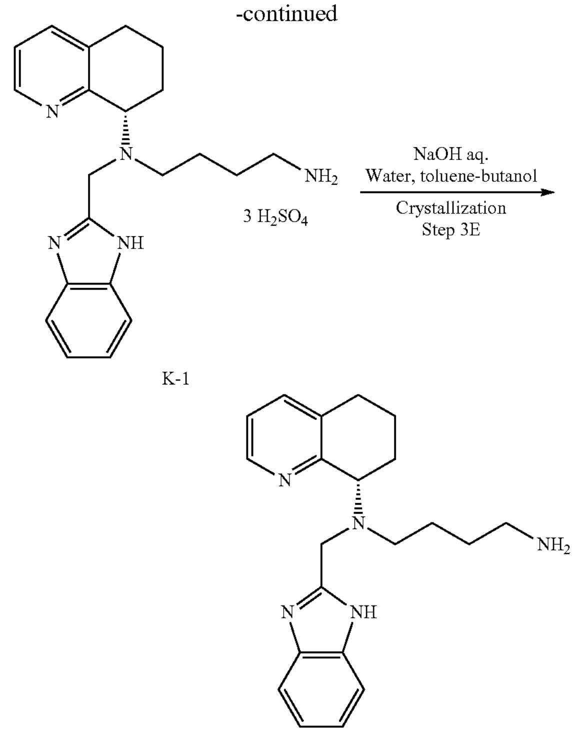

Mavorixafor Drug Substance

Step 3A: Preparation of Imine Q-1

To vessel A charge purified water, (8.7 vol, 8.7 wt) followed by potassium phosphate, (5.52 eq, 5.3 wt) portion-wise and cool to 15° C. Charge tetrahydrofuran, (4.3 vol, 3.8 wt) and n-heptane, (2.2 vol, 1.5 wt) to vessel A and cool the biphasic mixture to 0° C. Charge F-1, (1.00 eq, 1.00 wt) to the vessel in 2 portions maintaining 0° C.

Charge F-2d, (1.10 eq, 1.95 wt) to the vessel in 4 portions maintaining 0° C., ensuring portions are spaced by 10 min. Stir the resulting biphasic mixture for 1.5 h at 0° C. Allow the layers to separate for 45 min. at 0° C. before separating the layers. Retain the upper organic phase within vessel A.

Take the resulting solution of Q-1 into next reaction without isolation.

Step 3B: Preparation of Amine P-1

To vessel B, charge tetrahydrofuran, (6.0 vol, 5.3 wt) and adjust to 15° C. Charge zinc chloride, (1.5 eq, 0.92 wt) to vessel B in 4 portions, maintaining 10 to 30° C. Adjust the reaction mixture in vessel B to 15° C. Stir the mixture at 15° C. for 1 h. Charge sodium borohydride, (1.0 eq, 0.17 wt) to vessel B in 2 portions maintaining 15° C. Cool the reaction mixture in vessel B to 15° C. Stir the mixture for 1 h maintaining 15° C. Cool the reaction mixture in vessel B to −5° C.

Cool the retained organic solution of Q-1 in vessel A, from Step 3A, to −5° C.

Charge the organic solution in vessel A into vessel B over 1 to 2 h maintaining −5° C. Charge tetrahydrofuran, (1.0 vol, 0.9 wt) to vessel A as a line rinse and adjust to −5° C. Transfer the contents of vessel A to vessel B maintaining −5° C.

Stir the resulting reaction mixture in vessel B for 1.5 h maintaining −5° C.

Charge purified water, (4.5 vol, 4.5 wt) and glacial acetic acid, (1.0 eq, 0.27 wt, 0.26 vol) to the cleaned vessel A and cool to 0° C. Charge the contents of vessel B to vessel A over 1 to 2 h maintaining 0° C. Charge tetrahydrofuran, (1.0 vol, 0.9 wt) to vessel B as a vessel rinse, cool to 0° C. and transfer to vessel A maintaining 0° C.

Warm the resulting mixture in vessel A to 30° C. Stir the resulting mixture in vessel A at 30° C. for 1 h. Allow the layers to settle for 15 min. at 30° C. before separating the layers. Retain the upper organic phase.

Cool the retained organic phase to 15° C. Charge to the vessel 25% w/w ammonia solution (3.0 vol) at 10 to 30° C. Cool the reaction mixture to 20° C. Charge to the vessel 25% w/w ammonium chloride solution (3.0 vol) at 20° C. and stir for 1 h. Separate the layers for 15 min. at 20° C., retain the upper organic phase. Wash the retained organic phase with 10% w/w sodium chloride solution (3.0 vol) at 20° C. for 10 min. Allow the layers to settle for 10 min. at 20° C. before separating and retaining the upper organic phase within the vessel.

Charge tert-butyl methyl ether, (0.5 vol, 0.4 wt) to the organic phase. Cool the mixture to 5° C. Adjust the pH of the reaction mixture to pH 5 with hydrochloric acid aqueous solution (expected ca. 9.0 vol) over 1 h at a targeted constant rate at 5° C. Stir the mixture at 5° C. for 45 min. Measure the pH of the aqueous phase to confirm the value is pH 5.

Charge sodium chloride, (2.1 wt) to the reaction mixture at 5° C. and stir the mixture until everything is dissolved. Adjust the temperature of the reaction mixture to 20° C. Separate the layers at 20° C. and retain the organic phase within the vessel. Charge tetrahydrofuran, (1.5 vol, 1.3 wt) maintaining 20° C.

Charge to the vessel 24% w/w sodium chloride solution (7.5 vol) at 20° C. and stir for 10 min. Separate the layers at 20° C. and retain the organic phase in the vessel. This step is repeated additional one more time as described below.

Charge to the vessel 24% w/w sodium chloride solution (7.5 vol) at 20° C. and stir for 10 min. Separate the layers at 20° C. and retain the organic phase in the vessel.

Heat the retained organic phase to 35° C. and concentrate the mixture to 6.0 vol under reduced pressure maintaining 35° C.

Charge tetrahydrofuran, (15.0 vol, 13.2 wt) maintaining 35° C. Concentrate the mixture to 6.0 vol under reduced pressure maintaining 35° C.

Charge tetrahydrofuran, (15.0 vol, 13.2 wt) maintaining 35° C. Concentrate the mixture to 11.0 vol under reduced pressure maintaining 35° C.

Cool the mixture to −5° C. Charge tert-butyl methyl ether, (10.0 vol, 7.4 wt) over 1 h maintaining −5° C. Stir the mixture at −5° C. for 1.5 h. Filter the solid on 1 to 2 μm filter cloth at −5° C. Wash the solid with pre-mixed tetrahydrofuran, (1.9 vol, 1.7 wt) and tert-butyl methyl ether, (3.1 vol, 1.9 wt) at −5° C. as a displacement wash.

Wash the solid with tert-butyl methyl ether, (5.0 vol, 3.7 wt) at −5° C.

Dry the solid on the filter under a flow of nitrogen at 23° C.

Yield of compound P-1: 76-87%.

Step 3C: Preparation of Compound O-1

Charge purified water, (2.0 vol, 2.0 wt) followed by potassium phosphate, (3.3 eq, 1.54 wt), carefully portion-wise, maintaining ≤15° C., to vessel A. Charge toluene, (4.5 vol, 3.9 wt) to the vessel maintaining ≤15° C. As necessary, adjust the temperature to 10° C.

Charge P-1, (1.00 eq, 1.00 wt) to the vessel in two portions maintaining 10° C. Stir the reaction mixture at 10° C. for 15 min.

Charge F-3a, (1.1 eq, 0.64 wt) in 4 equal portions ensuring portions are spaced by 10 min. at 10° C.

Charge tetrabutylammonium iodide (TBAI) (0.20 eq, 0.16 wt). Heat the reaction mixture to 40° C. Stir the reaction mixture at 40° C. for 30 h.

Charge pre-mixed 2-mercaptoacetic acid, (0.40 eq, 0.08 wt, 0.06 vol), and toluene, (0.5 vol, 0.4 wt) over 20 min. to Vessel A at 40° C. Line rinse with toluene, (0.5 vol, 0.4 wt) at 40° C. Adjust the temperature of the reaction mixture to 50° C. Stir the mixture at 50° C. for 2.5 h.

Adjust the temperature of Vessel A to 20° C. Charge purified water, (3.0 vol, 3.0 wt) maintaining 20° C. Stir the reaction mixture at 20° C. for 15 min. and transfer to a new, clean HDPE container. Line/vessel rinse with toluene, (0.5 vol, 0.4 wt) at 20° C. Clarify (filter) the reaction mixture via a 1 μm filter at 20° C. into clean Vessel A. Wash the vessel and the filter with toluene, (0.5 vol, 0.4 wt) at 20° C. Allow the layers to separate for 15 min. at 20° C., retaining the upper organic layer (organic layer 1).

Wash the aqueous layer with toluene, (2.5 vol, 2.2 wt) at 20° C. for 15 min. Allow the layers to separate for 15 min. at 20° C. Retain the upper organic layer (organic layer 2).

Combine the organic layer 1 and organic layer 2 and adjust the temperature to 20° C. Wash the combined organic layers with 10% w/w sodium chloride solution (5.0 vol) at 20° C. for 15 min. Allow the layers to settle for 15 min. at 20° C. Retain the upper organic layer.

Take the resulting solution of O-1 into next reaction without isolation.

Step 3D: Preparation of Compound K-1

Charge n-butanol, (2.4 wt, 3.0 vol) to vessel B and adjust to 5° C. Charge concentrated sulfuric acid, (1.1 wt, 5.0 eq, 0.6 vol) slowly to Vessel B maintaining ≤15° C. Line rinse with toluene, (0.4 wt, 0.5 vol) maintaining ≤15° C. Adjust the temperature of Vessel B to 25° C.

Heat the n-butanol/sulfuric acid solution in Vessel B to 55° C. Charge the organic layer from Vessel A (from Step 3C) to the butanol/sulfuric acid solution in Vessel B over 60 to 90 min. maintaining 55° C. Charge toluene, (1.3 wt, 1.5 vol) to Vessel A as a line rinse and transfer to Vessel B maintaining 55° C. Stir the contents of Vessel B at 55° C. for 1.5 h.

Stir the mixture in Vessel B for 4.5 h at 55° C. Cool the contents of Vessel B to 20° C. over 10 h. Filter the slurry over 1-2 μm filter cloth under nitrogen at 20° C. Wash the filter cake with pre-mixed toluene, (3.5 wt, 4.0 vol) and n-butanol, (1.0 vol, 0.8 wt) at 20° C. Wash the filter cake with toluene, (4.3 wt, 5.0 vol) at 20° C. Dry the solid at 30° C. under vacuum.

Correct the output weight for assay. Expected 50-55% w/w.

Yield of compound K-1: 89-92%.

Step 3E: Preparation of Mavorixafor Drug Substance

Charge K-1, (1.00 eq, 1.00 wt, corrected for HPLC assay) in vessel A followed by nitrogen-purged purified water, (2.0 wt, 2.0 vol) and if necessary, adjust the temperature to 20° C. Charge nitrogen-purged toluene, (12.0 wt, 14.0 vol) to the solution maintaining 20° C. Charge nitrogen-purged n-butanol, (0.8 wt, 1.0 vol) to the solution maintaining 20° C. Heat the biphasic mixture to 30° C. Charge nitrogen-purged 3.0 M aqueous sodium hydroxide solution (6.2 eq, 5.9 vol) maintaining 30° C. Check the pH (expected 12 to 13). Adjust the pH of the aqueous layer to pH 10.0 with nitrogen-purged 0.3 M sulphuric acid solution (expected up to 2.5 vol) maintaining 30° C. Stir the mixture at 30° C. for 45 min.

Measure the pH to confirm the value is pH 10.0.

Allow the layers to settle at 30° C. for 30 min. and separate the layers retaining the organic phase in the vessel, and discharge the aqueous layer into a separate container (container C).

Charge pre-mixed toluene, (4.1 wt, 4.7 vol) and n-butanol, (0.24 wt, 0.3 vol) to a separate vessel; heat the contents to 30° C. and charge the aqueous layer from container C. As required adjust the temperature to 30° C. and stir for 5 to 10 min. at 30° C. Allow the phases to separate for 10 to 15 min. at 30° C. Discharge the aqueous phase to waste and combine the organic phase to the organic phase in vessel A.

Charge nitrogen-purged purified water, (2.0 wt, 2.0 vol) to the organic layer maintaining the temperature at 30° C. and stir for 5 to 10 min. at 30° C. Allow the phases to separate for 10 to 15 min. at 30° C. Discharge the aqueous phase to waste retaining the organic phase in the vessel. Heat the retained organic solution to 40° C. Concentrate the resulting organic phase to 7.0 vol by vacuum distillation at 40° C.

Charge nitrogen-purged toluene, (13.0 wt, 15.0 vol) to the mixture and concentrate the solution 7.0 vol by vacuum distillation at 40° C. This step is repeated additional one time as described below.

Charge nitrogen-purged toluene, (13.0 wt, 15.0 vol) to the mixture and concentrate the solution 7.0 vol by vacuum distillation at 40° C.

Charge nitrogen-purged toluene, (7.0 wt, 8.0 vol) to the mixture at 40° C., heat to 55° C. and clarify the hot reaction mixture under nitrogen via a 1 μm filter.

Charge clarified nitrogen-purged toluene, (1.7 wt, 2.0 vol) to the mixture as a line and vessel rinse at 40° C. Concentrate the solution to 7.0 vol by vacuum distillation at 40° C. At the end of the distillation the product is expected to have precipitated. Heat the mixture to 63° C.

Adjust the temperature to 60.5° C. This batch will be referred to as the main batch.

Charge seed material, (0.02 wt) to a new clean container. Charge clarified nitrogen-purged toluene, (0.09 wt, 0.10 vol) to this seed material and gently shake.

Seed the main batch with the slurry maintaining the temperature at 60.5±2° C. Stir the reaction at the 60.5±2° C. for 1 h.

Cool to 40° C. for 2.5 h. Stir the reaction at 40° C. for 1 h.

Cool to 30° C. over 2 h. Stir the reaction at 30° C. for 1 h.

Cool to 25° C. 50 min. Stir the reaction at 25° C. over 2 h.

Cool to 2° C. over 4 h. Stir the mixture for 12 h at 2° C.

Filter the mixture at 2° C. over 1 to 2 μm cloth. Wash the filter cake with clarified nitrogen-purged toluene, (2.0 vol, 1.7 wt) at 2° C. Dry the filter cake under vacuum and a flow of nitrogen for 1.5 h.

Dry the solid at 40° C. under vacuum and a flow of nitrogen until drying specification is achieved.

Yield of the final compound mavorixafor: 72%.

When toluene is used as the recrystallization solvent, optionally with a dissolution aid such butanol or methanol, for mavorixafor recrystallization, advantages were found compared to using dichloromethane and isopropyl acetate. We have found that these solvents do not react with the API, and accordingly we believe that this change has caused the significant reduction of impurities A (imine), B (N-formyl) and C (acetamide) that we have observed.

In some embodiments, the mavorixafor composition comprises 7000, 6000, 5000, 4500, 4450, 4000, 3500, 3000, 2500, 2000, 1750, 1700, 1650, 1600, 1550, 1500, 1450, 1400, 1350, 1300, 1250, 1200, 1150, 1100, 1050, 1000, 950, 900, 850, 800, 750, 700, 650, 600, 550, 500, 450, 400, 350, 300, 250, 200, 150, 100, or 50 ppm of toluene or less. In some embodiments, the mavorixafor composition comprises a detectable amount of toluene. In some embodiments, the mavorixafor composition comprises from a detectable amount of toluene to 1350 ppm of toluene. In some embodiments, the mavorixafor composition comprises from a detectable amount of toluene to 4450 ppm of toluene. In some embodiments, the mavorixafor composition comprises from 1750 ppm toluene to 4450 ppm of toluene. In some embodiments, the mavorixafor composition comprises from 1500 ppm toluene to 2500 ppm of toluene. In some embodiments, the mavorixafor composition comprises from a 1800 ppm toluene to 2200 ppm of toluene. In some embodiments, the mavorixafor composition comprises from a 1900 ppm toluene to 2100 ppm of toluene.

In some embodiments, toluene is used as a crystallization solvent for isolation of X4P-001. In certain embodiments, a specification for residual toluene in X4P-001 freebase is such that the mavorixafor composition comprises no more than 4500 ppm. In other embodiments, the mavorixafor composition comprises no more than 4000 ppm, 3500 ppm, 3000 ppm, 2500 ppm, 2000 ppm, 1750 ppm, 1700 ppm, 1650 ppm, 1600 ppm, 1550 ppm, 1500 ppm, 1450 ppm, 1400 ppm or 1350 ppm of toluene. In some embodiments, a permitted daily exposure (PDE) approach is used. The term permitted daily exposure (PDE) is defined as a pharmaceutically acceptable intake of residual solvents in a drug. See, e.g., *Guidance for Industry: Q3C Impurities: Residual Solvents* published by the Department of Health and Human Services, Food and Drug Administration (FDA).

We have found numerous advantages connected with the present process for isolation of mavorixafor drug product of superior purity (comprising mavorixafor free base) using a sulfate salt of formula K, such as the trisulfate salt K-1. K-1, in particular, was an appropriately stable and non-hygroscopic salt for use in forward processing of the initial deprotection product (i.e., crude mavorixafor resulting from removal of the Boc protecting groups in compound O). Our efforts to prepare a useful salt form of mavorixafor met with little success despite screening of multiple counter-ions. It was difficult to prepare a crystalline salt form of mavorixafor; of those salts that did crystallize, many had high hygroscopicity. This is well-known and described in the art. For example, WO 2003/055876 describes the hydrobromide salt of mavorixafor and is hereby incorporated by reference. U.S. Pat. No. 7,723,525, which is hereby incorporated by reference, describes a number of attempts to prepare salt forms of mavorixafor and notes at column 2, lines 4-10, that many suffer from problems associated with hygroscopicity. In particular, simple acid salts of mavorixafor such as hydrobromide and hydrochloride suffered from hygroscopicity. One goal of the invention described in U.S. Pat. No. 7,723,525 is to provide benzoate salts of mavorixafor having less hygroscopicity than the hydrobromide or hydrochloride salts, as well as increased stability (column 3, lines 55-65). U.S. Pat. No. 7,723,525 teaches that a group of benzoate salts such as 4-hydroxybenzoate, 4-aminobenzoate, 4-hydroxybenzenesulfonate, etc. had the desired properties (column 5, lines 3-9). However, the properties of other salts were unpredictable and many suffered from hygroscopicity as noted above. Formation of the mono-sulfate salt is described in Example 1 of U.S. Pat. No. 7,723,525, but its hygroscopicity and stability are not described or suggested. Similarly, although a trisulfate salt is mentioned, no such salt was prepared, nor were its properties determined or predicted.

In view of the unpredictability of screening for salt forms of mavorixafor with favorable properties, it was surprising and unexpected that sulfate forms of mavorixafor of formula K, such as the trisulfate, showed desirable properties and suitability for forward processing to the mavorixafor drug substance for use in ongoing clinical trials. Neither of these two advantages (desirable properties such as stability and suitability for forward processing) could have been predicted in advance.

We claim:

1. A method for preparing mavorixafor:

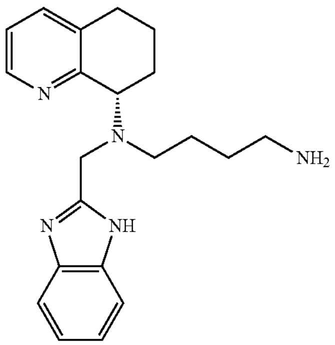

Mavorixafor comprising the steps of:

(a) providing a compound of formula B:

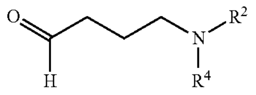

B wherein:

$R^2$ is a suitable amino protecting group; and $R^4$ is a suitable amino protecting group;

(b) sulfonating the compound of formula B to form a compound of formula F-2a:

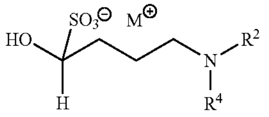

F-2a wherein:

M is a metal selected from alkali metals;

(c) condensing the compound of formula F-2a with compound F-1:

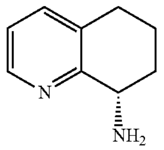

F-1 or a salt thereof, to form a compound of formula Q:

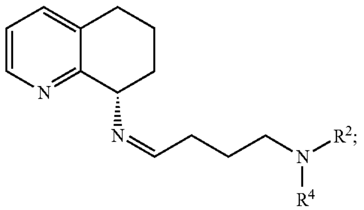

Q (d) reducing the compound of formula Q to form a compound of formula P:

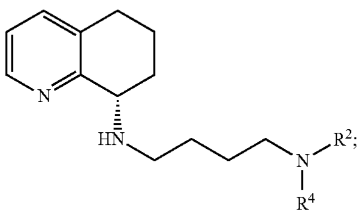

P (e) reacting the compound of formula P with a compound of formula F-3:

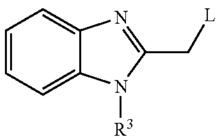

F-3 wherein:

$R^3$ is a suitable benzimidazole protecting group; and

L is a suitable leaving group;

to form a compound of formula O:

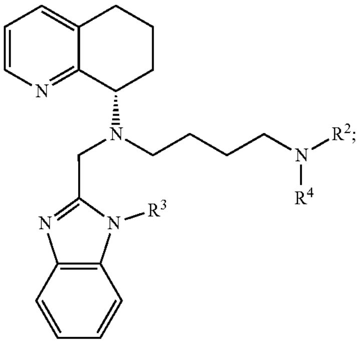

O (f) deprotecting the compound of formula O to form a compound of formula N:

N

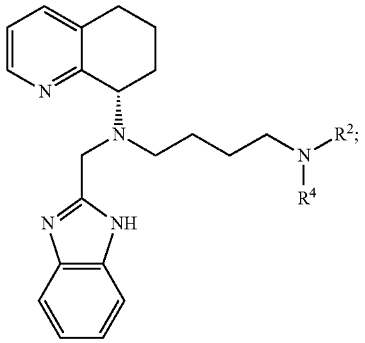

(g) deprotecting the compound of formula N to form a compound of formula M:

M

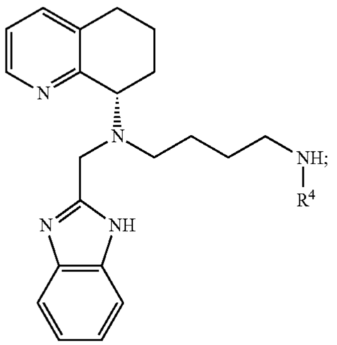

(h) deprotecting the compound of formula M to form a compound of formula K:

K

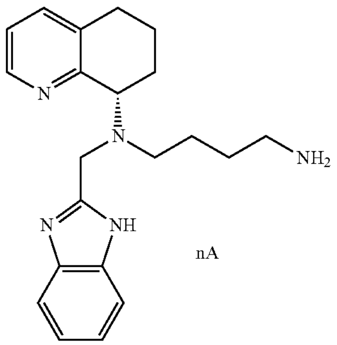

wherein:

A is an acid; and n is 1, 2 or 3;

and (i) converting the compound of formula K to form mavorixafor.

2. The method according to claim 1, wherein the $R^2$ group of formulae B, F-2a, Q, P, O and N is Boc; or wherein the $R^4$ group of formulae B, F-2a, Q, P, O, N and M is Boc; or wherein the $R^2$ and $R^4$ groups of formulae B, F-2a, Q, P, O and N are each Boc.

3. The method according to claim 1, wherein $R^3$ group of formulae F-3 and O is Boc.

4. The method according to claim 1, wherein each occurrence of $R^2$, $R^3$ and $R^4$ is Boc.

5. The method according to claim 1, wherein A in formula K is TFA, HCl, HBr, $H_3PO_4$ or $H_2SO_4$; and n is 1, 2 or 3.

6. The method according to claim 1, wherein the sulfonation at step (b) is achieved by reacting the compound of formula B with $MS_2O_5$, wherein M is an alkali metal selected from sodium and potassium.

7. The method according to claim 1, wherein the reduction at step (d) is achieved by reacting the compound of formula Q with a reducing agent, wherein the reducing agent is $NaBH_4$.

8. The method according to claim 1, wherein the reaction at step (e) is achieved by reacting the compound of formula P with a compound of formula F-3a:

F-3a

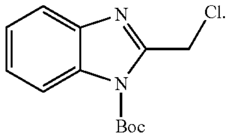

9. The method according to claim 1, wherein the reaction at step (i) is achieved by reacting the compound of formula K with a suitable base, wherein the suitable base is NaOH.

10. A method for preparing a compound of formula K:

K

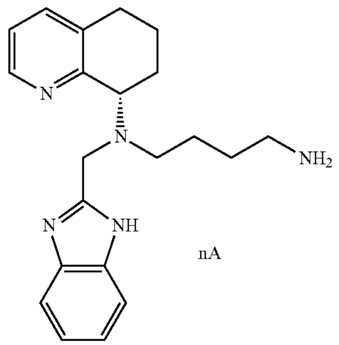

wherein:

A is an acid; and n is 1, 2 or 3;

comprising the steps of:

(a) providing a compound of formula B:

B

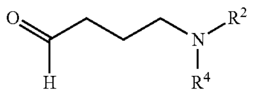

wherein:

$R^2$ is a suitable amino protecting group; and $R^4$ is a suitable amino protecting group;

(b) sulfonating the compound of formula B to form a compound of formula F-2a:

F-2a

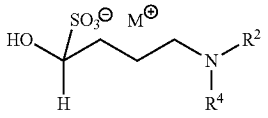

wherein:

M is a metal selected from alkali metals;

(c) condensing the compound of formula F-2a with compound F-1:

F-1

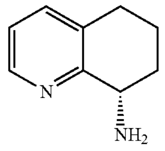

or a salt thereof, to form a compound of formula Q:

Q

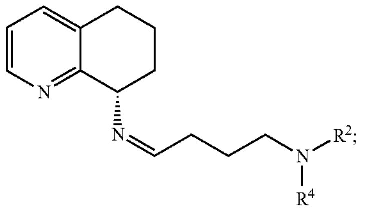

(d) reducing the compound of formula Q to form a compound of formula P:

P

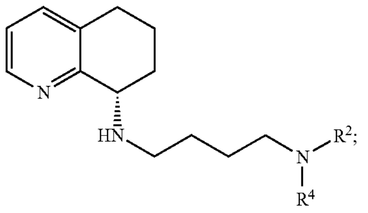

(e) reacting the compound of formula P with a compound of formula F-3:

F-3

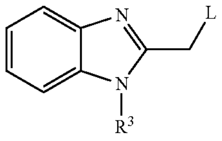

wherein:

$R^3$ is a suitable benzimidazole protecting group; and

L is a suitable leaving group;

to form a compound of formula O:

O

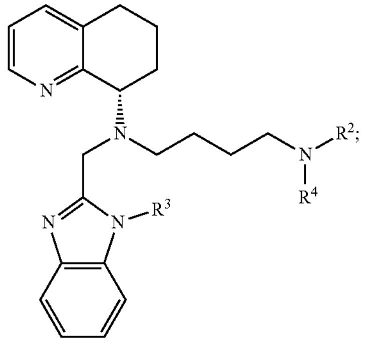

(f) deprotecting the compound of formula O to form a compound of formula N:

N

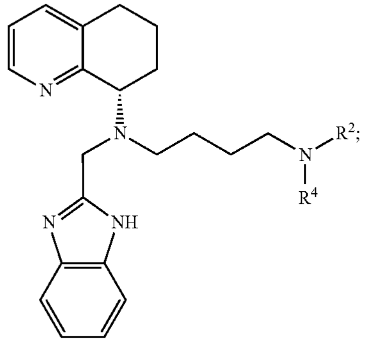

(g) deprotecting the compound of formula N to form a compound of formula M:

M

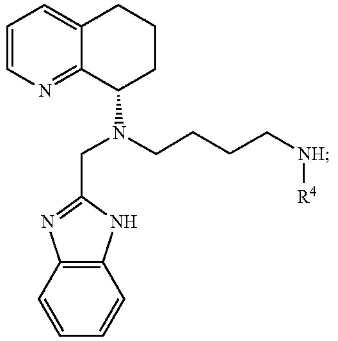

and (h) deprotecting the compound of formula M to form the compound of formula K.

11. The method according to claim 10, wherein the $R^2$ group of formulae B, F-2a, Q, P, 0 and N is Boc; or wherein the $R^4$ group of formulae B, F-2a, Q, P, O, N and M is Boc, or wherein the $R^2$ and $R^4$ groups of formulae B, F-2a, Q, P, O, N and M are each Boc.

* * * * *